(12) United States Patent
Eguiara et al.

(10) Patent No.: US 8,712,696 B2
(45) Date of Patent: Apr. 29, 2014

(54) METHODS OF PROGNOSING A RHEUMATOID ARTHRITIS REMISSION PHENOTYPE

(75) Inventors: Arrate Eguiara, Mondragón (ES); Diego Tejedor Hernández, Mungia (ES); Antonio Martínez Martínez, Laukariz (ES); Laureano Simón Buela, San Sebasián (ES)

(73) Assignee: Progenika Biopharma, S.A., Derio (ES)

( * ) Notice: Subject to any disclaimer, the term of this patent is extended or adjusted under 35 U.S.C. 154(b) by 1107 days.

(21) Appl. No.: 12/309,206

(22) PCT Filed: Jul. 12, 2007

(86) PCT No.: PCT/IB2007/002366
§ 371 (c)(1),
(2), (4) Date: Nov. 2, 2009

(87) PCT Pub. No.: WO2008/010085
PCT Pub. Date: Jan. 24, 2008

(65) Prior Publication Data
US 2010/0087441 A1   Apr. 8, 2010

(30) Foreign Application Priority Data

Jul. 12, 2006 (GB) .................................. 0613844.0

(51) Int. Cl.
*G06F 7/00* (2006.01)
(52) U.S. Cl.
USPC ................. 702/19; 702/20; 703/13; 707/700; 436/501
(58) Field of Classification Search
None
See application file for complete search history.

(56) References Cited

U.S. PATENT DOCUMENTS 6,905,827 B2 * 6/2005 Wohlgemuth et al. ....... 435/6.14
2005/0255504 A1   11/2005 Parl

FOREIGN PATENT DOCUMENTS

| EP | 1731608 | 12/2006 |
|---|---|---|
| WO | WO 01/12848 | 2/2001 |
| WO | WO 01/18240 | 3/2001 |
| WO | WO 2005/086872 * | 1/2005 |
| WO | WO 2005/022118 | 3/2005 |
| WO | WO 2005/086872 | 9/2005 |
| WO | WO 2005/093066 | 10/2005 |
| WO | WO 2006/075254 | 7/2006 |

OTHER PUBLICATIONS

Arnett et al., "The American Rheumatism Association 1987 Revised Criteria for the Classification of Rheumatoid Arthritis," *Arthritis and Rheumatism*, vol. 31, No. 3, pp. 315-324, 1988.

Balsa et al., "Prediction of functional impairment and remission in rheumatoid arthritis patients by biochemical variables and genetic polymorphisms," *Rheumatology*, vol. 49, pp. 458-466, 2010.

Bas et al., "Anti-cyclic citrullinated peptide antibodies, IgM and IgA rheumatoid factors in the diagnosis and prognosis of rheumatoid arthritis," *Rheumatology*, vol. 42, pp. 677-680, 2003.

Berglin et al., "Radiological outcome in rheumatoid arthritis is predicted by presence of antibodies against cyclic citrullinated peptide before and at disease onset, and by IgA-RF at disease onset," *Ann. Rheum. Dis.*, vol. 65, pp. 453-458, 2006.

Buchs et al., "IL-4 VNTR gene polymorphism in chronic polyarthritis. The rare allele is associated with protection against destruction," *Rheumatology*, vol. 39, pp. 1126-1131, 2000.

Combe et al., "Predictive factors of 5-year health assessment questionnaire disability in early rheumatoid arthritis," *J. Rheumatology*, vol. 30, pp. 2344-2349, 2003.

Cutler et al., "High-Throughput Variation Detection and Genotyping Using Microarrays," *Genome Research*, vol. 11, pp. 1913-1925, 2001.

Dervieux et al., "Polyglutamation of Methotrexate With Common Polymorphisms in Reduced Folate Carrier, Aminoimidazole Carboxamide Ribonucleotide Transformylase, and Thymidylate Synthase are Associated With Methotrexate Effects in Rheumatoid Arthritis," *Arthritis and Rheumatism*, vol. 50, No. 9, pp. 2766-2774, 2004.

Dervieux et al., "Pharmacogenetic and metabolite measurements are associated with clinical status in patients with rheumatoid arthritis treated with methotrexate: results of a multicentred cross sectional observational study," *Ann. Rheum. Dis.*, vol. 64, pp. 1180-1185, 2005.

Eberhardt et al., "Associations of HLA-DRB and —DQB genes with two and five year outcome in rheumatoid arthritis," *Ann. Rheum. Dis.*, vol. 55, pp. 34-39, 1996.

Johansson et al., "*PTPN22* polymorphism and anti-cyclic citrullinated peptide antibodies in combination strongly predicts future onset of rheumatoid arthritis and has a specificity of 100% for the disease," *Arthritis Research and Therapy*, vol. 8, R19, 2006.

Khanna et al., "Association of Tumor Necrosis Factor α Polymorphism, But Not the Shared Epitope, With Increased Radiographic Progression in a Seropositive Rheumatoid Arthritis Inception Cohort," *Arthritis and Rheumatism*, vol. 54, No. 4, pp. 1105-1116, 2006.

Mattey et al., "Association of polymorphism in the transforming growth factor β1 gene with disease outcome and mortality in rheumatoid arthritis," *Ann. Rheum. Dis.*, vol. 64, pp. 1190-1194, 2005.

McKendry and Dale, "Adverse Effects of Low Dose Methotrexate Therapy in Rheumatoid Arthritis," *J. Rheumatology*, vol. 20, pp. 1850-1856, 1993.

Prots et al., "Association of the *IL4R* Single-Nucleotide Polymorphism I50V With Rapidly Erosive Rheumatoid Arthritis," *Arthritis and Rheumatism*, vol. 54, No. 5, pp. 1491-1500, 2006.

(Continued)

*Primary Examiner* — Mary Zeman
(74) *Attorney, Agent, or Firm* — Klarquist Sparkman, LLP

(57) ABSTRACT

A method for prognosing a rheumatoid arthritis phenotype using the outcomes of selected single nucleotide polymorphisms (SNPs) and clinical variables. A method for genotyping multiple rheumatoid arthritis associated genetic variations comprising use of a DNA microarray. A microarray for use in the described methods.

20 Claims, 53 Drawing Sheets

(56) References Cited

OTHER PUBLICATIONS

Rodriguez-Lopez et al., "Regulatory polymorphisms in extracellular matrix protease genes and susceptibility to rheumatoid arthritis: a case-control study," *Arthritis Research and Therapy*, vol. 8, R1, 2006.

Rossi et al., "Use of the Sharp and Larsen Scoring Methods in the Assessment of Radiographic Progression in Juvenile Idiopathic Arthritis," *Arthritis and Rheumatism*, vol. 55, No. 5, pp. 717-723, 2006.

Sokka et al., "Functional Disability in Rheumatoid Arthritis Patients Compared With a Community Population in Finland," *Arthritis and Rheumatism*, vol. 48, No. 1, pp. 59-63, 2003.

Tejedor et al., "Reliable Low-Density DNA Array Based on Allele-Specific Probes for Detection of 118 Mutations Causing Familial Hypercholesterolemia," *Clinical Chemistry*, vol. 51, No. 7, pp. 1137-1144, 2005.

Verstappen et al., "Joint surgery in the Utrecht Rheumatoid Arthritis Cohort: the effect of treatment strategy," *Ann. Rheum. Dis.*, vol. 65, pp. 1506-1511, 2006.

Vos et al., "Human Leukocyte Antigen-DQ and DR Polymorphisms Predict Rheumatoid Arthritis Outcome Better Than DR Alone," *Human Immunology*, vol. 62, pp. 1217-1225, 2001.

\* cited by examiner

Figure 1: Table 1A: Genetic variations associated with RA

The Solute Carrier Family 22 A4 (SLC22A4) C1672T polymorphism.

The Runt-related Transcription Factor 1 (RUNX1) C24658G polymorphism

The Peptidylarginine Deiminase type IV (PADI 4) G117A polymorphism

The Peptidylarginine Deiminase type IV (PADI 4) G55S polymorphism.

The Peptidylarginine Deiminase type IV (PADI 4) V82A polymorphism

The Peptidylarginine Deiminase type IV (PADI 4) G112A polymorphism

The Major Histocompatibility Complex class I chain-related gene A (MICA) Hla25 polymorphism The Major Histocompatibility Complex class I chain-related gene A (MICA) Hla28 polymorphism.

The NOTCH4 Hla58 T/G polymorphism

The Vascular Endothelial Growth Factor (VEGF) G1154A polymorphism.

The Vascular Endothelial Growth Factor (VEGF) C634G polymorphism.

The Vascular Endothelial Growth Factor (VEGF)C936T polymorphism.

The Interleukin 18 (IL18) A607C polymorphism.

The Interleukin 18 (IL18) G-137C polymorphism.

The Interleukin 4 receptor (IL-4R) Q551R polymorphism.

The IL-1 receptor antagonist allele 2 (IL1RN*2) T2018C polymorphism.

The IL-1 receptor antagonist allele 2 (IL1RN*2) C2073T polymorphism.

The Programmed Death 1 (PD-1, PDCD1) C872T polymorphism.

FIGURE 1 (Cont.)

The Toll-Like Receptor 4 (TLR4) Asp299Gly polymorphism.

The Vitamin D (1,25- dihydroxyvitamin D3) receptor Apos.VS7+283(b>B) polymorphism.

The T-cell immunoglobulin domain and mucin domain 3 (TIM3) C-547T polymorphism.

The T-cell immunoglobulin domain and mucin domain 3 (TIM3) T4259G polymorphism.

The Urokinase (-A2849G) 3' UTR polymorphism.

The Cytotoxic T-lymphocyte antigen-4 (CTLA4A/G) in exon 1.

The Transporter associated with antigen processing 2 (TAP2) Ala565Thr polymorphism.

The I kappa BL A-62T polymorphism. Poly (ADP-ribose) polymerase 1 (PARP-1) C1362T polymorphism.

The Protein-tyrosine phosphatase T1858C polymorphism.

The Vitamin D Receptor Fok I polymorphism.

The Uteroglobin (UG) G38A polymorphism.

The Matrix Metalloproteinase 3 (MMP3) 6A/6A polymorphism.

The Tumor Protein p53 Arg/Arg and the Pro/Pro genotypes at codon 72.

The Interleukin 10 (IL-10) (–A2849G) polymorphism.

The Tumor necrosis factor-alpha gene promotor (TNF alpha) the –308, the +488, the -857 and the –238 polymorphisms.

The Tumor Necrosis Factor Receptor 2 (TNFR2) T587G polymorphism.

The Tumor Necrosis Factor Receptor 1 (TNFR1) +36 A/A polymorphism.

The Fibrinogen B beta polypeptide (FGB).G-455A polymorphism.

FIGURE 1 (Cont.)

The Glutathione S-transferase M1 transcript variant 1 GSTM1 null genotype polymorphism.

The Glutathione S-transferase T1 (GSTT1) GSTT1-0 genotype polymorphism.

The Multidrug Resistance Protein (MDR-1) (−C3435T) polymorphism.

The Adhesion Molecule 1 (ICAM1) R241G polymorphism.

The Interleukin 1 beta (IL-1B) C3954T polymorphism.

The Chondromodulin II (Chm II) Val58Ile polymorphism.

The Interleukin 6 gene (IL-6) − 622 polymorphism.

The 5-Aminoimidazole-4-carboxamide ribonucleotide formyltransferase / IMP cyclohydrolase (ATIC) 347 GG. Solute Carrier Family 22 member 4 (SLC22A4) G80A polymorphism.

The Methylenetetrahydrofolate Reductase (MTHFR) C677T and A1298C polymorphism.

The Lymphotoxin alpha gene (LTA) 249, 365 and 720 polymorphism.

The Interleukin 10 (IL-10) -1087 G/G allele and the Tumor necrosis factor-alpha (TNF)-308 TNF1/TNF1 allele (These variations are associated with RA in combination, but not alone)

The Transforming Growth Factor beta TGFbeta1 (rare C allele in codon 25) and IL1 receptor antagonist (A2 allele in intron 2) (These variations are associated with RA in combination, but not alone). Codon 10 T869C polymorphism.

The Interleukin-10 gene (IL-10) -1087 AA polymorphism.

The N-Acetyltransferase 2 (arylamine N-acetyltransferase) 282C>T, 590G>A, 341T>C, 481C>T, 803A>G, 857G>A and 191G>A polymorphism.

The Thiopurine methyltransferase (TPMT) G460A and the A719G polymorphisms.

FIGURE 1 (Cont.)

The Fc receptor-like protein 3 (FCRL3) –C196T polymorphism.

The Tapasin gene (TPSN) Arg260Thr polymorphism.

The Poly(ADP-ribose) polymerase 1 (PARP-1) haplotype A (410T-[A](10)-[CA](10-12)-1362C, which includes short PARP-1 CA alleles) and haplotype B (410C-[A](11)-[CA](13-20)-1362T.

The Histocompatibility Antigen Hla 76 and Hla 78 polymorphisms.

The Melatonin Receptor 1B (MTNR1B) polymorphism.

The Major Histocompatibility Complex, class II, Transactivator (MHC2TA) polymorphism (-168A→G).

The BETA-2-Adrenergic Receptor polymorphism.

The Methylenetetrahydrofolate Reductase (MTHFR) A1298C polymorphism.

The Monocyte chemotactic protein 1 (MCP1) polymorphism (-2518)G>A polymorphism.

The FAS LIGAND gene minus 843C/T polymorphism.

The Inflammatory Bowel Disease gene IBD5 locusIGR2060a_1 polymorphism.

The cd16a gene V158F (G/T) polymorphism.

The Interleukin 1 beta (IL1b) minus 511a/c polymorphism.

The Interleukin 4 (IL4) 34c/t polymorphism.

The Caspase 9 C93T polymorphism.

The Intracellular Adhesion Molecule 1 (ICAM1) K469E polymorphism.

The Lectin, Mannose-binding (MBL) gene Gly54Asp polymorphism.

The Interleukin 4 (IL4) gene -590 polymorphism.

FIGURE 1 (Cont.)

The THIOPURINE S-METHYLTRANSFERASE 5 (TPMT5) gene T145C (Leu49Ser) polymorphism.

The THIOPURINE S-METHYLTRANSFERASE 6 (TPMT6) gene A539T polymorphism.

The THIOPURINE S-METHYLTRANSFERASE 7 (TPMT7) gene T681G (His227Gln) polymorphism.

The THIOPURINE S-METHYLTRANSFERASE 8 (TPMT8) gene G644A (Arg215His) polymorphism.

The Histocompatability Antigen HLA b27 polymorphism.

The Solute Carrier Family 19 (folate reductase) SLC19A1 G80A.

FIGURE 1 (Cont.): Table 1B

| #SNP | Gene Symbol | Gene Name | Polymorphism |
|---|---|---|---|
| 1 | SLC22A4 | Solute Carrier Family 22 A4 | C1672T |
| 2 | RUNX1 | Runt-related Transcription Factor 1 | C24658G |
| 3 | PADI 4 | Peptidylarginine Deiminase type IV | G117A |
| 4 | PADI 4 | Peptidylarginine Deiminase type IV | G55S |
| 5 | PADI 4 | Peptidylarginine Deiminase type IV | V82A |
| 6 | PADI 4 | Peptidylarginine Deiminase type IV | G112A |
| 7 | MICA | Major Histocompatibility Complex class I chain-related gene A | Hla25 |
| 8 | MICA | Major Histocompatibility Complex class I chain-related gene A | Hla28 |
| 9 | NOTCH4 | Notch homolog 4 | Hla58 T/G |
| 10 | VEGF | Vascular Endothelial Growth Factor | G1154A |
| 11 | VEGF | Vascular Endothelial Growth Factor | C634G |
| 12 | VEGF | Vascular Endothelial Growth Factor | C936T |
| 13 | IL18 | Interleukin 18 | A607C |
| 14 | IL18 | Interleukin 18 | G-137C |
| 15 | IL-4R | Interleukin 4 receptor | Q551R |
| 16 | IL1RN*2 | IL-1 receptor antagonist allele 2 | T2018C |
| 17 | IL1RN*2 | IL-1 receptor antagonist allele 2 | C2073T |
| 18 | PD-1, PDCD1 | Programmed Death 1 | C872T |
| 19 | TLR4 | Toll-Like Receptor 4 | Asp299Gly |
| 20 | VDR | Vitamin D (1,25- Dihydroxyvitamin D3) Receptor | AposVS7+283b>B |
| 21 | TIM3 | T-Cell Immunoglobulin Domain And Mucin Domain 3 | C-547T |
| 22 | TIM3 | T-Cell Immunoglobulin Domain And Mucin Domain 3 | T4259G |
| 23 | PLAU | Plasminogen Activator, Urokinase | 3' UTR -A2849G |
| 24 | CTLA4 | Cytotoxic T-Lymphocyte Antigen-4 | A/G in exon 1 |
| 25 | TAP2 | Transporter Associated With Antigen Processing 2 | Ala565Thr |
| 26 | NFKBIL1 | Nuclear Factor Of Kappa Light Polypeptide Gene Enhancer In B-Cells Inhibitor-Like 1 | A-62T |
| 27 | PARP-1 | Poly ADP-ribose polymerase 1 | C1362T |
| 28 | PTP | Protein-tyrosine phosphatase | T1858C |
| 29 | VDR | Vitamin D Receptor | Fok I |
| 30 | UG | Uteroglobin | G38A |
| 31 | MMP3 | Matrix Metalloproteinase 3 | 6A/6A |
| 32 | p53 | Tumor Protein | Arg/Arg and the Pro/Pro genotypes at codon 72 |

FIGURE 1 (Cont.)

| # | Gene | Description | Variant |
|---|---|---|---|
| 33 | IL-10 | Interleukin 10 | -A2849G |
| 34 | TNF alpha | Tumor Necrosis Factor-Alpha Gene Promotor | the -308 |
| 35 | TNF alpha | Tumor Necrosis Factor-Alpha Gene Promotor | the +488 |
| 36 | TNF alpha | Tumor Necrosis Factor-Alpha Gene Promotor | the -857 |
| 37 | TNF alpha | Tumor Necrosis Factor-Alpha Gene Promotor | the -238 |
| 38 | TNFR2 | Tumor Necrosis Factor Receptor 2 | T587G |
| 39 | TNFR1 | Tumor Necrosis Factor Receptor 1 | +36 A/A |
| 40 | FGB. | Fibrinogen B beta polypeptide | G-455A |
| 41 | GSTM1 | Glutathione S-transferase M1 transcript variant 1 | null genotype |
| 42 | GSTT1 | Glutathione S-transferase T1 | GSTT1-0 genotype |
| 43 | MDR-1 | Multidrug Resistance Protein | -C3435T |
| 44 | ICAM1 | Adhesion Molecule 1 | R241G |
| 45 | IL-1B | Interleukin 1 beta | C3954T |
| 46 | Chm II | Chondromodulin II | Val58Ile |
| 47 | IL-6 | Interleukin 6 gene | -622 |
| 48 | ATIC | 5-Aminoimidazole- 4 -carboxamide ribonucleotide formyltransferase / IMP cyclohydrolase | 347 GG |
| 49 | SLC22A4 | Solute Carrier Family 22 member 4 | G80A |
| 50 | MTHFR | Methylenetetrahydrofolate Reductase | C677T |
| 51 | LTA | Lymphotoxin alpha gene | 249 |
| 52 | LTA | Lymphotoxin alpha gene | 365 |
| 53 | LTA | Lymphotoxin alpha gene | 720 |
| 54 | IL-10 | Interleukin 10 | -1087 G/G |
| 55 | TNF | Tumor necrosis factor-alpha | -308 TNF1/TNF1 |
| 56 | TGFbeta1 | Transforming Growth Factor | |
| 57 | IL-10 | Interleukin-10 gene | -1087 AA |
| 58 | TPMT | Thiopurine methyltransferase | G460A |
| 59 | TPMT | Thiopurine methyltransferase | A719G |
| 60 | FCRL3 | Fc receptor-like protein 3 | -C196T |
| 61 | TPSN | Tapasin gene | Arg260Thr |
| 62 | NAT2 | N-Acetyltransferase 2 | 341T>C |
| 63 | NAT2 | N-Acetyltransferase 2 | 481C>T |
| 64 | NAT2 | N-Acetyltransferase 2 | 803A>G |
| 65 | NAT2 | N-Acetyltransferase 2 | 857G>A |
| 66 | NAT2 | N-Acetyltransferase 2 | 191G>A |

FIGURE 1 (Cont.)

| # | Gene | Description | Variant |
|---|------|-------------|---------|
| 67 | Hla | Histocompatibility Antigen | 78 |
| 68 | Hla | Histocompatibility Antigen | 76 |
| 69 | MTNR1B | Melatonin Receptor 1B | |
| 70 | MHC2TA | Major Histocompatibility Complex, class II, Transactivator | |
| 71 | ADRB2 | BETA-2-Adrenergic Receptor | A1298C |
| 72 | MTHFR | Methylenetetrahydrofolate Reductase | |
| 73 | MCP1 | Monocyte chemotactic protein 1 | minus 843C/T |
| 74 | FASLG | Fas Ligand | locuslGR2060a_1 |
| 75 | IBD5 | Inflammatory Bowel Disease 5 | V158F G/T |
| 76 | CD16a | Fc fragment of IgG, low affinity IIIa, receptor | minus 511a/c |
| 77 | IL1B | Interleukin 1 beta | 34c/t |
| 78 | IL4 | Interleukin 4 | C93T |
| 79 | CASP9 | Caspase 9 | K469E |
| 80 | ICAM1 | Intercellular Adhesion Molecule 1 | Gly54Asp |
| 81 | MBL | lectin, mannose-binding | -590 |
| 82 | IL4 | Interleukin 4 | |
| 83 | TPMT5 | Thiopurine S-Methyltransferase 5 | T145C Leu49Ser |
| 84 | TPMT6 | Thiopurine S-Methyltransferase 6 | A539T |
| 85 | TPMT7 | Thiopurine S-Methyltransferase 7 | T681G His227Gln |
| 86 | TPMT 8 | Thiopurine S-Methyltransferase 8 | G644A Arg215His |
| 87 | HLA | Histocompatibility Antigen | b27 polimorphism |
| 88 | SLC19A1 | Solute Carrier Family 19 folate reductase | G80A |
| 89 | NAT2 | N-Acetyltransferase 2 | 282 |
| 90 | NAT2 | N-Acetyltransferase 2 | 590 |

Figure 2: Table 2

1.- Solute Carrier Family 22 A4 (SLC22A4) C1672T polymorphism. (probes to detect the polymorphism C1672T of the gene *Solute Carrier Family 22 A4*)

AAAAAAGGGTGAGGATTCCAATCAG

AAAAAAGGGTGAAGATTCCAATCAG

AAAAAGGGTGAGGATTCCAATCA

AAAAAGGGTGAAGATTCCAATCA

2.- Runt-related Transcription Factor 1 (RUNX1) C24658G polymorphism

TAAGAGCTGTCCCTGGGGCAGAT

TAAGAGCTGTCGCTGGGGCAGAT

ATCTGCCCCAGGGACAGCTCTTA

ATCTGCCCCAGCGACAGCTCTTA

3.- Peptidylarginine Deiminase type IV (PADI 4) G117A polymorphism

CAGAAATCTCCCTGTGCGCAGAC

CAGAAATCTCCTTGTGCGCAGAC

GTCTGCGCACAGGGAGATTTCTG

GTCTGCGCACAAGGAGATTTCTG

4.- Peptidylarginine Deiminase type IV (PADI 4) G55S polymorphism.

ATATTGCCCACGGCCCTCCAGCC

ATATTGCCCACAGCCCTCCAGCC

GGCTGGAGGGCCGTGGGCAATAT

GGCTGGAGGGCTGTGGGCAATAT

5.- Peptidylarginine Deiminase type IV (PADI 4) V82A polymorphism

GACGATGAAAGTGGCCAGTGGTA

GACGATGAAAGCGGCCAGTGGTA

TACCACTGGCCACTTTCATCGTC

TACCACTGGCCGCTTTCATCGTC

FIGURE 2 (Cont.)

6.- Peptidylarginine Deiminase type IV (PADI 4) G112A polymorphism

CTACCTCACCGCGGTGGGTAAGT

CTACCTCACCGGGGTGGGTAAGT

ACTTACCCACCGCGGTGAGGTAG

ACTTACCCACCCCGGTGAGGTAG

7.- Major Histocompatibility Complex class I chain-related gene A (MICA) Hla25 polymorphism

AGCGGGAGCAGAGGGACGTTTCC

AGCGGGAGCAGGGGGACGTTTCC

GGAAACGTCCCTCTGCTCCCGCT

GGAAACGTCCCCCTGCTCCCGCT

8.- Major Histocompatibility Complex class I chain-related gene A (MICA) Hla28 polymorphism.

GCCCTGCCTGTGTAGCCCTTTGG

GCCCTGCCTGTTTAGCCCTTTGG

CCAAAGGGCTACACAGGCAGGGC

CCAAAGGGCTAAACAGGCAGGGC

9.- NOTCH4 Hla58 T/G polymorphism.

CACACAGACAAATCAGTTCTTGA

CACACAGACAACTCAGTTCTTGA

TCAAGAACTGATTTGTCTGTGTG

TCAAGAACTGAGTTGTCTGTGTG

10.- Vascular Endothelial Growth Factor (VEGF) G1154A polymorphism.

CCGCGTGTGGAGGGGCTGAGGCT

AGCCTCAGCCCCTCCACACGCGG

CCGCGTGTGGAAGGGCTGAGGCT

AGCCTCAGCCCCTCCACACGCGG

11.- Vascular Endothelial Growth Factor (VEGF) C634G polymorphism.

FIGURE 2 (Cont.)

AGCAGCGAAAGGGACAGGGGCAA

AGCAGCGAAAGCGACAGGGGCAA

TTGCCCCTGTCCCTTTCGCTGCT

TTGCCCCTGTCGCTTTCGCTGCT

12.- Vascular Endothelial Growth Factor (VEGF)C936T polymorphism.

GTGACCCAGCACGGTCCCTCTTG

GTGACCCAGCATGGTCCCTCTTG

CAAGAGGGACCGTGCTGGGTCAC

CAAGAGGGACCATGCTGGGTCAC

13.- Interleukin 18 (IL18) A607C polymorphism.

AAAAATTATTACATAAAATTCTA

AAAAATTATTAAATAAAATTCTA

TAGAATTTTATGTAATAATTTTT

TAGAATTTTATTTAATAATTTTT

14.- Interleukin 18 (IL18) G-137C polymorphism.

ACGGAAGAAAACATTTCATGAAA

ACGGAAGAAAAGATTTCATGAAA

TTTCATGAAATGTTTTCTTCCGT

TTTCATGAAATCTTTTCTTCCGT

15.- Interleukin 4 receptor (IL-4R) Q551R polymorphism.

CAGTGGCTATCGGGAGTTTGTAC

CAGTGGCTATCAGGAGTTTGTAC

GTACAAACTCCCGATAGCCACTG

GTACAAACTCCTGATAGCCACTG

16.- IL-1 receptor antagonist allele 2 (IL1RN*2) T2018C polymorphism.

CCAACTAGTTGCTGGATACTTGCAA

CCAACTAGTTGCCGGATACTTGCAA

FIGURE 2 (Cont.)

CAACTAGTTGCTGGATACTTGCA

CAACTAGTTGCCGGATACTTGCA

17.- IL-1 receptor antagonist allele 2 (IL1RN*2) C2073T polymorphism.

GCCAGGAAAGCCAATGTATGT

GCCAGGAAAGTCAATGTATGT

GCCAGGAAAGCCAATGTATGT

GCCAGGAAAGTCAATGTATGT

18.- Programmed Death 1 (PD-1, PDCD1) C872T polymorphism.

AGGGGCTCAGCCGACGGCCCTCG

AGGGGCTCAGCTGACGGCCCTCG

CGAGGGCCGTCGGCTGAGCCCCT

CGAGGGCCGTCAGCTGAGCCCCT

19. Toll-Like Receptor 4 (TLR4) Asp299Gly polymorphism.

AAGTCAATAATATCATCGAGGTAGT

AAGTCAATAATACCATCGAGGTAGT

AGTCAATAATATCATCGAGGTAG

AGTCAATAATACCATCGAGGTAG

20. Vitamin D (1,25- dihydroxyvitamin D3) receptor Apos.VS7+283(b>B) polymorphism.

GACAGGCCTGCGCATTCCCAATA

GACAGGCCTGCACATTCCCAATA

TATTGGGAATGCGCAGGCCTGTC

TATTGGGAATGTGCAGGCCTGTC

21. T-cell immunoglobulin domain and mucin domain 3 (TIM3) C-547T polymorphism.

CTGGGAGTTGCGATGGTCTGTAA

CTGGGAGTTGCTATGGTCTGTAA

TTACAGACCATCGCAACTCCCAG

FIGURE 2 (Cont.)

TTACAGACCATAGCAACTCCCAG

22. T-cell immunoglobulin domain and mucin domain 3 (TIM3) T4259G polymorphism.

TGCACCGACTCTGCAGAGAGACT

TGCACCGACTCGGCAGAGAGACT

AGTCTCTCTGCAGAGTCGGTGCA

AGTCTCTCTGCCGAGTCGGTGCA

23. Urokinase 3' UTR (-A2849G) polymorphism.

ACCCACCAGGGCGAACGACAATA

ACCCACCAGGGTGAACGACAATA

TATTGTCGTTCGCCCTGGTGGGT

TATTGTCGTTCACCCTGGTGGGT

24. Cytotoxic T-lymphocyte antigen-4 (CTLA4A/G) in exon 1.

TGAACCTGGCTGCCAGGACCTGG

TGAACCTGGCTACCAGGACCTGG

CCAGGTCCTGGCAGCCAGGTTCA

CCAGGTCCTGGTAGCCAGGTTCA

25. Transporter associated with antigen processing 2 (TAP2) Ala565Thr polymorphism.

GGAACAACATTGCTTATGGGCTG

CAGCCCATAAGCAATGTTGTTCC

GGAACAACATTACTTATGGGCTG

CAGCCCATAAGTAATGTTGTTCC

26. I kappa BL A-62T polymorphism.

AGCAGAGACGCAGGTGGAGGACG

AGCAGAGACGCTGGTGGAGGACG

CGTCCTCCACCTGCGTCTCTGCT

CGTCCTCCACCAGCGTCTCTGCT

FIGURE 2 (Cont.)

27. Poly (ADP-ribose) polymerase 1 (PARP-1) C1362T polymorphism.
Poly(ADP-ribose) polymerase 1 (PARP-1) haplotype A (410T-[A](10)-[CA](10-12)-1362C, which includes short PARP-1 CA alleles) and haplotype B (410C-[A](11)-[CA](13-20)-1362T.

AGGCGGGGCCCGCGCTTCCCGG

AGGCGGGGCCTGCGCTTCCCGG

CCGGGAAGCGCGGGCCCCCGCCT

CCGGGAAGCGCAGGCCCCCGCCT

28. Protein-tyrosine phosphatase T1858C polymorphism.

CACTTCCTGTACGGACACCTGAA

CACTTCCTGTATGGACACCTGAA

TTCAGGTGTCCGTACAGGAAGTG

TTCAGGTGTCCATACAGGAAGTG

29. Vitamin D Receptor Fok I polymorphism.

TCTTACAGGGATGGAGGCAATGG

TCTTACAGGGACGGAGGCAATGG

CCATTGCCTCCATCCCTGTAAGA

CCATTGCCTCCGTCCCTGTAAGA

30. Uteroglobin (UG) G38A polymorphism.

GAACCAGAGACGGGCCAGAGCAT

GAACCAGAGACAGGCCAGAGCAT

ATGCTCTGGCCCGTCTCTGGTTC

ATGCTCTGGCCTGTCTCTGGTTC

31. Matrix Metalloproteinase 3 (MMP3) 6A/6A polymorphism.

ACATGGTTTTTCCCCCCATCAA

ACATGGTTTTTCCCCCCATCAAA

TTGATGGGGGGAAAAAACCATGT

TTGATGGGGGGGAAAAAACCATGT

32. Tumor Protein p53 Arg/Arg and the Pro/Pro genotypes at codon 72.

FIGURE 2 (Cont.)

CAGGGGCCACGCGGGGAGCAGCC

CAGGGGCCACGGGGGGAGCAGCC

GGCTGCTCCCCGCGTGGCCCCTG

GGCTGCTCCCCCCGTGGCCCCTG

33. Interleukin 10 (IL-10) (-A2849G) polymorphism.

ACCTTATGATCTGCCCGCCTTGG

ACCTTATGATCCGCCCGCCTTGG

CCAAGGCGGGCAGATCATAAGGT

CCAAGGCGGGCGGATCATAAGGT

34. Tumor necrosis factor-alpha gene promotor (TNF alpha) the -308.

ACCCCGTCCCCATGCCCCT

ACCCCGTCCTCATGCCCCT

ACCCCGTCCCCATGCCCCT

ACCCCGTCCTCATGCCCCT

35. Tumor necrosis factor-alpha gene promotor (TNF alpha) the +488.

GAGAAAAAAACATGGAGAAAGAC

GAGAAAAAAACGTGGAGAAAGAC

AGGTCCTGGCAGCCAGGTT

AGGTCCTGGTAGCCAGGTT

36. Tumor necrosis factor-alpha gene promotor (TNF alpha) the -857

GAACCAGAGACGGGCCAGAGCAT

GAACCAGAGACAGGCCAGAGCAT

ATGCTCTGGCCCGTCTCTGGTTC

ATGCTCTGGCCTGTCTCTGGTTC

37. Tumor necrosis factor-alpha gene promotor (TNF alpha) the -238

CTCCCTGCTCCGATTCCGAGG

CTCCCTGCTCTGATTCCGAGG

FIGURE 2 (Cont.)

TCCCTGCTCCGATTCCGAG

TCCCTGCTCTGATTCCGAG

38. Tumor Necrosis Factor Receptor 2 (TNFR2) T587G polymorphism.

GAATGCAAGCATGGATGCAGTCT

GAATGCAAGCAGGGATGCAGTCT

GACTGCATCCATGCTTGCATT

GACTGCATCCCTGCTTGCATT

39. Tumor Necrosis Factor Receptor 1 (TNFR1) +36 A/A polymorphism.

CTGCTGCTGCCGCTGGTGAGACC

CTGCTGCTGCCACTGGTGAGACC

GGTCTCACCAGCGGCAGCAGCAG

GGTCTCACCAGTGGCAGCAGCAG

40. Fibrinogen B beta polypeptide (FGB).G-455A polymorphism.

TTGATTTTAATGGCCCCTTTTGA

TTGATTTTAATAGCCCCTTTTGA

TCAAAAGGGGCCATTAAAATCAA

TCAAAAGGGGCTATTAAAATCAA

41. Glutathione S-transferase M1 transcript variant 1 GSTM1 null genotype polymorphism.

ACACATTCTTGGCCTTCTGCAGA

ACACATTCTTGACCTTCTGCAGA

TCTGCAGAAGGCCAAGAATGTGT

TCTGCAGAAGGTCAAGAATGTGT

42. Glutathione S-transferase T1 ( GSTT1) GSTT1-0 genotype polymorphism.

TGCCTAGTGGGTTCACCTGCCCA

TGCCTAGTGGGGTCACCTGCCCA

TGGGCAGGTGAACCCACTAGGCA

TGGGCAGGTGACCCCACTAGGCA

FIGURE 2 (Cont.)

43. Multidrug Resistance Protein (MDR-1) (-C3435T) polymorphism.

AGGAAGAGATCGTGAGGGCAG

AGGAAGAGATTGTGAGGGCAG

AGGAAGAGATCGTGAGGGCAG

AGGAAGAGATTGTGAGGGCAG

44. Adhesion Molecule 1 (ICAM1) R241G polymorphism.

TTCCCTGGACGGGCTGTTCCC

TTCCCTGGACAGGCTGTTCCC

GGGAACAGCCCGTCCAGGGAA

GGGAACAGCCTGTCCAGGGAA

45. Interleukin 1 beta (IL-1B) C3954T polymorphism.

ACCTATCTTCTTCGACACATGGGAT

ACCTATCTTCTTTGACACATGGGAT

ATCCCATGTGTCGAAGAAGATAGGT

ATCCCATGTGTCAAAGAAGATAGGT

46. Chondromodulin II (Chm II) Val58Ile polymorphism.

AGGGTGTGGACGTCTTGTGCTCT

AGGGTGTGGACATCTTGTGCTCT

AGAGCACAAGACGTCCACACCCT

AGAGCACAAGATGTCCACACCCT

47. Interleukin 6 gene (IL-6) - 622 polymorphism.

TGGGATTTTCCGATGCTAAAGGA

TGGGATTTTCCCATGCTAAAGGA

TCCTTTAGCATCGGAAAATCCCA

TCCTTTAGCATGGGAAAATCCCA 48. 5 -Aminoimidazole- 4 -carboxamide ribonucleotide formyltransferase / IMP cyclohydrolase (ATIC) 347 GG.

TCCAGGTGTAACTGTTGAGGAGG

FIGURE 2 (Cont.)

TCCAGGTGTAAGTGTTGAGGAGG

CCTCCTCAACAGTTACACCTGGA

CCTCCTCAACACTTACACCTGGA

49. Solute Carrier Family 22 member 4 (SLC22A4) G80A polymorphism.

AAAAAAGGGTGAGGATTCCAATCAG

AAAAAAGGGTGAAGATTCCAATCAG

AAAAAGGGTGAGGATTCCAATCA

AAAAAGGGTGAAGATTCCAATCA

50. Methylenetetrahydrofolate Reductase (MTHFR) C677T polymorphism.

GATGAAATCGGCTCCCGCAGA

GATGAAATCGACTCCCGCAGA

GATGAAATCGGCTCCCGCAGA

GATGAAATCGACTCCCGCAGA

51. Lymphotoxin alpha gene (LTA) 249 polymorphism.

ACAGAGAGGAATCATGGCAGAAA

ACAGAGAGGAACCATGGCAGAAA

TTCTGCCATGATTCCTCTCTG

TTCTGCCATGGTTCCTCTCTG

52. Lymphotoxin alpha gene (LTA) 365 polymorphism.

CGGGGGGTGCTCTCTCCCAGGGC

CGGGGGGTGCTGTCTCCCAGGGC

GCCCTGGGAGAGAGCACCCCCCG

GCCCTGGGAGACAGCACCCCCCG

53. Lymphotoxin alpha gene (LTA) 720 polymorphism.

CAGGTTTGAGGGTGCTGTGGGCA

CAGGTTTGAGGTTGCTGTGGGCA

GGTTTGAGGGTGCTGTGGG

FIGURE 2 (Cont.)

GGTTTGAGGTTGCTGTGGG

54. Interleukin 10 (IL-10) -1087 G/G polymorphism

CTTCTTTGGGAAGGGGAAGTAGG

CTTCTTTGGGAGGGGGAAGTAGG

CCTACTTCCCCTAGGGTTTCTTC

CCTACTTCCCCCAGGGTTTCTTC

55. Tumor necrosis factor-alpha (TNF)-308 TNF1/TNF1 polymorphism

ACCCCGTCCCCATGCCCCT

ACCCCGTCCTCATGCCCCT

ACCCCGTCCCCATGCCCCT

ACCCCGTCCTCATGCCCCT

56. Transforming Growth Factor TGFbetal polymorphism.

GACGCCTGGCCGGCCGGCCGCGG

GACGCCTGGCCCGCCGGCCGCGG

CCGCGGCCGGCCGGCCAGGCGTC

CCGCGGCCGGCGGGCCAGGCGTC

57. Interleukin-10 gene (IL-10) -1087 AA polymorphism.

CTTCTTTGGGAGGGGGAAGTAGG

CTTCTTTGGGAAGGGGAAGTAGG

CCTACTTCCCCCAGGGTTTCTTC

CCTACTTCCCCTAGGGTTTCTTC

58. Thiopurine methyltransferase (TPMT) G460A polymorphism.

TGGGATAGAGGAGCATTAGTTGCCA

TGGGATAGAGGAACATTAGTTGCCA

GGGATAGAGGAGCATTAGTTGCC

GGGATAGAGGAACATTAGTTGCC

59. Thiopurine methyltransferase (TPMT) A719G polymorphism.

FIGURE 2 (Cont.)

TCTGTAAGTAGATATAACTTTTCAA

TCTGTAAGTAGACATAACTTTTCAA

CTGTAAGTAGATATAACTTTTCA

CTGTAAGTAGACATAACTTTTCA

60. Fc receptor-like protein 3 (FCRL3) -C196T polymorphism.

ACGGGAAGTCCTTGATCTGTACA

ACGGGAAGTCCCTGATCTGTACA

TGTACAGATCAAGGACTTCCCGT

TGTACAGATCAGGGACTTCCCGT

61. Tapasin gene (TPSN) Arg260Thr polymorphism.

CTGGCTGCCTAGAGTTCAACCCT

CTGGCTGCCTACAGTTCAACCCT

AGGGTTGAACTCTAGGCAGCCAG

AGGGTTGAACTGTAGGCAGCCAG

62. N-Acetyltransferase 2 (NAT2) 341T>C polymorphism.

GCAGGTGACCATTGACGGCAGGA

TCCTGCCGTCAATGGTCACCTGC

GCAGGTGACCACTGACGGCAGGA

TCCTGCCGTCAGTGGTCACCTGC

63. N-Acetyltransferase 2 (NAT2) 481C>T polymorphism.

GAATCTGGTACCTGGACCAAATC

GATTTGGTCCAGGTACCAGATTC

GAATCTGGTACTTGGACCAAATC

GATTTGGTCCAAGTACCAGATTC

64. N-Acetyltransferase 2 (NAT2) 803A>G polymorphism.

AGAAGTGCTGAAAAATATATTTA

TAAATATATTTTTCAGCACTTCT

FIGURE 2 (Cont.)

AGAAGTGCTGAGAAATATATTTA

TAAATATATTTCTCAGCACTTCT

65. N-Acetyltransferase 2 (NAT2) 857G>A polymorphism.

ACCTGGTGATGGATCCCTTACTA

TAGTAAGGGATCCATCACCAGGT

ACCTGGTGATGAATCCCTTACTA

TAGTAAGGGATTCATCACCAGGT

66. N-Acetyltransferase 2 (NAT2) 191G>A polymorphism.

AAGAAGAAACCGGGGTGGGTGGT

ACCACCCACCCCGGTTTCTTCTT

AAGAAGAAACCAGGGTGGGTGGT

ACCACCCACCCTGGTTTCTTCTT

67. Histocompatibility Antigen Hla 78 polymorphism.

TTCCCCCCAGCGTGGCAGGATCT

TTCCCCCCAGCATGGCAGGATCT

AGATCCTGCCACGCTGGGGGGAA

AGATCCTGCCATGCTGGGGGGAA

68. Histocompatibility Antigen Hla 76 polymorphism.

TCAAGAACTGATTTGTCTGTGTG

TCAAGAACTGAGTTGTCTGTGTG

CACACAGACAAATCAGTTCTTGA

CACACAGACAACTCAGTTCTTGA

69. Melatonin Receptor 1B (MTNR1B) polymorphism.

TTCCCCCCAGCATGGCAGGATCT

TTCCCCCCAGCGTGGCAGGATCT

AGATCCTGCCA TGCTGGGGGGAA

AGATCCTGCCACGCTGGGGGGAA

FIGURE 2 (Cont.)

70. Major Histocompatibility Complex, class II, Transactivator (MHC2TA) polymorphism.

TTCAGAGGTGTAGGGAGGGCTTA

TTCAGAGGTGTGGGGAGGGCTTA

TAAGCCCTCCCTACACCTCTGAA

TAAGCCCTCCCCACACCTCTGAA

71. BETA-2-Adrenergic Receptor polymorphism.

TGGCACCCAATGGAAGCCATGCG

TGGCACCCAATAGAAGCCATGCG

CGCATGGCTTCCATTGGGTGCCA

CGCATGGCTTCTATTGGGTGCCA

72. Methylenetetrahydrofolate Reductase (MTHFR) A1298C polymorphism.

GACCAGTGAAGAAAGTGTCTTTG

GACCAGTGAAGCAAGTGTCTTTG

CAAAGACACTTTCTTCACTGGTC

CAAAGACACTTGCTTCACTGGTC

73. Monocyte chemotactic protein 1 (MCP1).

GGCAGACAGCTGTCACTTTCCAG

GGCAGACAGCTATCACTTTCCAG

CTGGAAAGTGACAGCTGTCTGCC

CTGGAAAGTGATAGCTGTCTGCC

74. FAS LIGAND minus 843C/T polymorphism.

TGAAAACATTGCGAAATACAAAG

TGAAAACATTGTGAAATACAAAG

TTTGTATTTCGCAATGTTTTC

TTTGTATTTCACAATGTTTTC

75. IBD5 locusIGR2060a_1 polymorphism.

CCTTGCAACCCTGGCAAAGGTAATG

FIGURE 2 (Cont.)

CCTTGCAACCCTCGCAAAGGTAATG

CATTACCTTTGCCAGGGTTGCAAGG

CATTACCTTTGCGAGGGTTGCAAGG

76. cd16a V158F (G/T) polymorphism.

TGCAGGGGGCTTGTTGGGAGTAAAA

TGCAGGGGGCTTTTTGGGAGTAAAA

TTACTCCCAACAAGCCCCCTG

TTACTCCCAAAAAGCCCCCTG

77. Interleukin 1 beta minus 511a/c polymorphism.

AAGAGAATCCCAGAGCAGCCTGT

AAGAGAATCCCCGAGCAGCCTGT

ACAGGCTGCTCTGGGATTCTCTT

ACAGGCTGCTCGGGGATTCTCTT

78. Interleukin 4 (IL4) 34c/t polymorphism.

TAAACTAATTGCCTCACATTGTC

TAAACTAATTGTCTCACATTGTC

GACAATGTGAGGCAATTAGTTTA

GACAATGTGAGACAATTAGTTTA

79. Caspase 9 C93T polymorphism.

GTCCTGCTGAGCCGCGAGCTGTT

GTCCTGCTGAGTCGCGAGCTGTT

ACAGCTCGCGGCTCAGCAGGA

ACAGCTCGCGACTCAGCAGGA

80. ICAM1 K469E polymorphism.

AGGTCACCCGCAAGGTGACCGTG

CACGGTCACCTTGCGGGTGACCT

AGGTCACCCGCGAGGTGACCGTG

FIGURE 2 (Cont.)

CACGGTCACCTCGCGGGTGACCT

81. LECTIN, MANNOSE-BINDING (MBL) Gly54Asp polymorphism.

TGGGCGTGATGACACCAAGGGAG

CTCCCTTGGTGTCATCACGCCCA

TGGGCGTGATGGCACCAAGGGAG

CTCCCTTGGTGCCATCACGCCCA

82. Interleukin 4 -590 polymorphism.

GAGAACATTGTCCCCCAGTGCTG

CAGCACTGGGGGACAATGTTCTC

GAGAACATTGTTCCCCAGTGCTG

CAGCACTGGGGAACAATGTTCTC

83. Thiopurine S-Methyltransferase 5 TPMT5 T145C (Leu49Ser) polymorphism.

CTTCAGGCTATTAAAGAAGCATT

CTTCAGGCTATCAAAGAAGCATT

AATGCTTCTTTAATAGCCTGAAG

AATGCTTCTTTGATAGCCTGAAG

84. Thiopurine S-Methyltransferase 6 TPMT6 A539T polymorphism.

GAAGTTTCAGTATCTCCTGTGTG

GAAGTTTCAGTTTCTCCTGTGTG

CACACAGGAGAT ACTGAAACTTC

CACACAGGAGAAACTGAAACTTC

85. Thiopurine S-Methyltransferase 7 TPMT7 T681G (His227Gln) polymorphism.

GAAGAACGACATAAAAGTTGGGG

GAAGAACGACAGAAAAGTTGGGG

CCCCAACTTTT ATGTCGTTCTTC

CCCCAACTTTT CTGTCGTTCTTC

FIGURE 2 (Cont.)

86. Thiopurine S-Methyltransferase 8 TPMT 8 G644A (Arg215His) polymorphism.

ATGCAATATACGTTGTCTTGAGA

ATGCAATATACATTGTCTTGAGA

TCTCAAGACAACGTATATTGCAT

TCTCAAGACAATGTATATTGCAT

87. Histocompatibility Antigen HLA b27 polimorphism.

Gacagcgacgccgcgagtccgag

Ctcggactcgcggcgtcgctgtc

Gacagcgacgccgcgagtccgag

Ctcggactcgcggcgtcgctgtc

88. Solute Carrier Family 19 ( folate reductase ) SLC19A1 G80A.

GTCCTGGCGGCGCCTCGTGTGCT

GTCCTGGCGGCACCTCGTGTGCT

AGCACACGAGGCGCCGCCAGGAC

AGCACACGAGGTGCCGCCAGGAC

89. N-Acetyltransferase 2 (NAT2) 282 polymorphism.

GGGTATTTTTACATCCCTCCAGT

GGGTATTTTTATATCCCTCCAGT

GGTATTTTTACATCCCTCCAG

GGTATTTTTATATCCCTCCAG

90. N-Acetyltransferase 2 (NAT2) 590 polymorphism.

CTTCAATTGTTCGAGGTTCAAGC

CTTCAATTGTTTGAGGTTCAAGC

GCTTGAACCTCGAACAATTGAAG

GCTTGAACCTCAAACAATTGAAG

Figure 3: Table 3

Solute Carrier Family 22 A4 (SLC22A4) C1672T polymorphism. (probes to detect polymorphism C1672T of gene Solute Carrier Family 22 A4)

GCTAGATGAAGAGCAAGCGCCAAGAGTGCCCAGAGAGTCC

TACAACCGACAGATGTATGTTTCTCCCTAAGGCATTTTGGT

Runt-related Transcription Factor 1 (RUNX1) C24658G polymorphism

GCTAGATGAAGAGCAAGCGCTCTCCACTGTGCTGATGAGG

TACAACCGACAGATGTATGTTTTTTCTTGCGTGCTGACAC

Peptidylarginine Deiminase type IV (PADI 4) G117A polymorphism.

GCTAGATGAAGAGCAAGCGCACCCTCACCAACCTCTCCTC

TACAACCGACAGATGTATGTACACGGAATACGTGGGACAG

Peptidylarginine Deiminase type IV (PADI 4) G55S polymorphism.

GCTAGATGAAGAGCAAGCGCCCCATGTGTCTTGTCCACAG

TACAACCGACAGATGTATGTTCGTCAGGGTCACCTCTACC

Peptidylarginine Deiminase type IV (PADI 4) V82A polymorphism.

GCTAGATGAAGAGCAAGCGC CCCATGTGTCTTGTCCACAG

TACAACCGACAGATGTATGTCCCCACAGCTATGACACTCA

Peptidylarginine Deiminase type IV (PADI 4) G112A polymorphism.

GCTAGATGAAGAGCAAGCGCTCCAGTGGGTGTTTGTTGA

TACAACCGACAGATGTATGTGGATGAGACGGCACTCTAGG

Major Histocompatibility Complex class I chain-related gene A (MICA) Hla25 polymorphism.

GCTAGATGAAGAGCAAGCGCCATCTTCCCTTTTGCACCT

TACAACCGACAGATGTATGTGATCCCGAGGAGGACTGAA

Major Histocompatibility Complex class I chain-related gene A (MICA) Hla28 polymorphism.

GCTAGATGAAGAGCAAGCGCATGCTAAGGGCCTGGATGAT

FIGURE 3 (Cont.)

TACAACCGACAGATGTATGTCAGGACCCTCCCTGTTACAA

NOTCH4 Hla58 T/G polymorphism.

GCTAGATGAAGAGCAAGCGCGGCCAAAACAACCATCTGAG

TACAACCGACAGATGTATGTTCCCTCATGGTTGGGTTAAA

Vascular Endolial Growth Factor (VEGF) G1154A polymorphism.

GCTAGATGAAGAGCAAGCGCTTTTCAGGCTGTGAACCTTG

TACAACCGACAGATGTATGTGAGATCCTCCCCGCTACCAG

Vascular Endolial Growth Factor (VEGF) C634G polymorphism.

GCTAGATGAAGAGCAAGCGCGGATTTTGGAAACCAGCAGA

TACAACCGACAGATGTATGTCTGTCTGTCTGTCCGTCAGC

Vascular Endolial Growth Factor (VEGF)C936T polymorphism.

GCTAGATGAAGAGCAAGCGCAGGGTTTCGGGAACCAGATC

TACAACCGACAGATGTATGTCTCGGTGATTTAGCAGCAAG

Interleukin 18 (IL18) A607C polymorphism.

GCTAGATGAAGAGCAAGCGCTCCCTCTCCCCAAGCTTACT

TACAACCGACAGATGTATGTTTCAGGACTTCCCCTTCCTC

Interleukin 18 (IL18) G-137C polymorphism.

GCTAGATGAAGAGCAAGCGCGTGCTGAAGTGTGACCAGGA

TACAACCGACAGATGTATGTGGGCAATGGAAGTCGAAATA

Q551R polymorphism in the Interleukin 4 receptor (IL-4R)

GCTAGATGAAGAGCAAGCGCCAACCTGAGCCAGAAACCTG

TACAACCGACAGATGTATGTCCACATTTCTCTGGGGACAC

**IL-1 receptor antagonist allele 2 (IL1RN*2) T2018C polymorphism.**

GCTAGATGAAGAGCAAGCGCACAAGTTCTGGGGACACAG

TACAACCGACAGATGTATGTATTGCACCTAGGGTTTGTGC

Programmed Death 1 (PD-1, PDCD1) C872T polymorphism.

GCTAGATGAAGAGCAAGCGCGTGCCTGTGTTCTCTGTGGA

FIGURE 3 (Cont.)

TACAACCGACAGATGTATGTCCAAGAGCAGTGTCCATCCT

**IL-1 receptor antagonist allele 2 (IL1RN*2) C2073T polymorphism.**

GCTAGATGAAGAGCAAGCGCCTCTAGAGGGCCTGTGCAAT

TACAACCGACAGATGTATGTTCAATGTGGGAAACTGTCCA

Vitamin D (1,25- dihydroxyvitamin D3) receptor Apos.VS7+283(b>B) polymorphism.

GCTAGATGAAGAGCAAGCGCCCTCACTGCCCTTAGCTCTG

TACAACCGACAGATGTATGTCCCGCAAGAAACCTCAAATA

T-cell immunoglobulin domain and mucin domain 3 (TIM3) C-547T polymorphism.

GCTAGATGAAGAGCAAGCGCTGAGGCTTATGCTGGGAGTT

TACAACCGACAGATGTATGTAAATGGAGCATGTCCGAGTC

T-cell immunoglobulin domain and mucin domain 3 (TIM3) T4259G polymorphism.

GCTAGATGAAGAGCAAGCGCCCCCTTTGATTCCCTGAAATA

TACAACCGACAGATGTATGTGCCCCATGCATAGTTACCTG

Urokinase 3' UTR (-A2849G) polymorphism.

GCTAGATGAAGAGCAAGCGCAGGCTCTGCACAGATGGATT

TACAACCGACAGATGTATGTATGCCCTGCCCTTTTTAACT

Cytotoxic T-lymphocyte antigen-4 (CTLA4A/G) in exon 1.

GCTAGATGAAGAGCAAGCGCCTGAACACCGCTCCCATAAA

TACAACCGACAGATGTATGTCCTCCTCCATCTTCATGCTC

Transporter associated with antigen processing 2 (TAP2) Ala565Thr polymorphism.

GCTAGATGAAGAGCAAGCGC GCACCAGGTGTTCATTCTGA

TACAACCGACAGATGTATGT CCGCCATCACCTTATCATCT

I kappa BL A-62T polymorphism.

GCTAGATGAAGAGCAAGCGCCCCAAGGCCTGTGTTTAAGA

TACAACCGACAGATGTATGTGCCTCCAGTCCAGTCTTCTG

FIGURE 3 (Cont.)

Poly (ADP-ribose) polymerase 1 (PARP-1) C1362T polymorphism. Poly(ADP-ribose) polymerase 1 (PARP-1) haplotype A (410T-[A](10)-[CA](10-12)-1362C, which includes short PARP-1 CA alleles) and haplotype B (410C-[A](11)-[CA](13-0)1362T.

GCTAGATGAAGAGCAAGCGCAGGAGGGTGGACCTAGCACT

TACAACCGACAGATGTATGTCAAGTGATCTTCACGCCTCA

Protein-tyrosine phosphatase T1858C polymorphism.

GCTAGATGAAGAGCAAGCGCGGATAGCAACTGCTCCAAGG

TACAACCGACAGATGTATGTTCACACATCAGCTTCCCAAA

Vitamin D Receptor Fok I polymorphism.

GCTAGATGAAGAGCAAGCGCGGCCTGCTTGCTGTTCTTAC

TACAACCGACAGATGTATGTTGCTTCTTCTCCCTCCCTTT

Uteroglobin (UG) G38A polymorphism.

GCTAGATGAAGAGCAAGCGCCTTGCTGGGCATGTCTCATA

TACAACCGACAGATGTATGTGGGGGTCCTGAGAGTTCCTA

Matrix Metalloproteinase 3 (MMP3) 6A/6A polymorphism.

GCTAGATGAAGAGCAAGCGCTCACTGCCACCACTCTGTTC

TACAACCGACAGATGTATGTGCCTCAACCTCTCAAAGTGC

Tumor Protein p53 Arg/Arg and Pro/Pro genotypes at codon 72.

GCTAGATGAAGAGCAAGCGCCTGCCCTGGTAGGTTTTCTG

TACAACCGACAGATGTATGTGAAGACCCAGGTCCAGATG

Interleukin 10 (IL-10) (-A2849G) polymorphism.

GCTAGATGAAGAGCAAGCGCTCTCAGCTCACTGCAAGCTC

TACAACCGACAGATGTATGTACAGTGGCTCATGCCTGTAA

Tumor necrosis factor-alpha gene promotor (TNF alpha) -308 polymorphism.

GCTAGATGAAGAGCAAGCGCAAAGATGTGCGCTGATAGGG

TACAACCGACAGATGTATGTTTCCCCCATCTCTCTTCTCA

Tumor necrosis factor-alpha gene promotor (TNF alpha) -238 polymorphism.

FIGURE 3 (Cont.)

GCTAGATGAAGAGCAAGCGCAAAGATGTGCGCTGATAGGG

TACAACCGACAGATGTATGTTTCCCCCATCTCTCTTCTCA

Tumor necrosis factor-alpha gene promotor (TNF alpha) +488 polymorphism.

GCTAGATGAAGAGCAAGCGCACCTGGTCCCCAAAAGAAAT

TACAACCGACAGATGTATGTAAAGTTGGGGACACACAAGC

Tumor necrosis factor-alpha gene promotor (TNF alpha) -857 polymorphism.

GCTAGATGAAGAGCAAGCGCTGTCCAGGGCTATGGAAGTC

TACAACCGACAGATGTATGTTTTCATTCTGACCCGGAGAC

Tumor Necrosis Factor Receptor 2 (TNFR2) T587G polymorphism.

GCTAGATGAAGAGCAAGCGCCTCTCCTATCCTGCCTGCTG

TACAACCGACAGATGTATGTGGCTGGGGTAAGTGTACTGC

Tumor Necrosis Factor Receptor 1 (TNFR1) +36 A/A polymorphism.

CTGCTGCTGCCGCTGGTGAGACC GGTCTCACCAGCGGCAGCAGCAG

CTGCTGCTGCCACTGGTGAGACC GGTCTCACCACTGGCAGCAGCAG

Fibrinogen B beta polypeptide (FGB).G-455A polymorphism.

GCTAGATGAAGAGCAAGCGCGGAGTGAGAGGCCATAGCTG

TACAACCGACAGATGTATGTGCAGTGGCTGAGGTTAGGAC

Glutathione S-transferase M1 transcript variant 1 GSTM1 null genotype polymorphism.

GCTAGATGAAGAGCAAGCGCATGGTTTGCAGGAAACAAGG

TACAACCGACAGATGTATGTAAAGCGGGAGATGAAGTCCT

Glutathione S-transferase T1 (GSTT1) GSTT1-0 genotype polymorphism.

GCTAGATGAAGAGCAAGCGCGGCAGCATAAGCAGGACTTC

TACAACCGACAGATGTATGTGTTGCTCGAGGACAAGTTCC

Multidrug Resistance Protein (MDR-1) (-C3435T) polymorphism.

GCTAGATGAAGAGCAAGCGC TGCTCCCAGGCTGTTTATTT

TACAACCGACAGATGTATGT TGTTTTCAGCTGCTTGATGG

FIGURE 3 (Cont.)

Adhesion Molecule 1 (ICAM1) R241G polymorphism.

GCTAGATGAAGAGCAAGCGCGAATGAAATGCCCCAGAGAA

TACAACCGACAGATGTATGTACTGTGGGGTTCAACCTCTG

Interleukin 1 beta (IL-1B) C3954T polymorphism.

GCTAGATGAAGAGCAAGCGCTGTTCTTAGCCACCCCACTC

TACAACCGACAGATGTATGTGTGATCGTACAGGTGCATCG

Chondromodulin II (Chm II) Val58Ile polymorphism.

GCTAGATGAAGAGCAAGCGC CTGCAAACAGTGGGCTAACA

TACAACCGACAGATGTATGT CCCACAATCATTCCAGTGAA

Interleukin 6 gene (IL-6) - 622 polymorphism.

GCTAGATGAAGAGCAAGCGCTCCCCCTAGTTGTGTCTTGC

TACAACCGACAGATGTATGTTCATGGGAAAATCCCACATT

5-Aminoimidazole- 4 -carboxamide ribonucleotide formyltransferase / IMP cyclohydrolase (ATIC) 347 GG.

GCTAGATGAAGAGCAAGCGCGACAGTGGCTTCTCCAGGTG

TACAACCGACAGATGTATGTTCCCAAAACACAATCCAGAA

Solute Carrier Family 22 member 4 (SLC22A4) G80A polymorphism.

GCTAGATGAAGAGCAAGCGCCAAGAGTGCCCAGAGAGTCC

TACAACCGACAGATGTATGTTTCTCCCTAAGGCATTTTGGT

Methylenetetrahydrofolate Reductase (MTHFR) C677T polymorphism.

GCTAGATGAAGAGCAAGCGCGCCTCTCCTGACTGTCATCC

TACAACCGACAGATGTATGTTCACAAAGCGGAAGAATGTG

Methylenetetrahydrofolate Reductase (MTHFR) A1298C polymorphism.

GCTAGATGAAGAGCAAGCGCGCCTCTCCTGACTGTCATCC

TACAACCGACAGATGTATGTTCACAAAGCGGAAGAATGTG

Lymphotoxin alpha gene (LTA) 249 polymorphism.

GCTAGATGAAGAGCAAGCGCGGGTTTGGTTTTGGTTTCCT

FIGURE 3 (Cont.)

TACAACCGACAGATGTATGTCCCGAGAGAGAGATCGACAG

Lymphotoxin alpha gene (LTA) 365 polymorphism.

GCTAGATGAAGAGCAAGCGCTGTCTCCCTCTGCTCACCTT

TACAACCGACAGATGTATGTAGGAGGAGGTGTAGGGTGGT

Lymphotoxin alpha gene (LTA) 720 polymorphism.

GCTAGATGAAGAGCAAGCGCAGGTGAGGCAGCAGGAGAAT

TACAACCGACAGATGTATGTATGAGGTGAGCAGCAGGTTT

Interleukin 10 (IL-10) -1087 G/G polymorphism.

GCTAGATGAAGAGCAAGCGCTTCCCCAGGTAGAGCAACAC

TACAACCGACAGATGTATGTGATGGGGTGGAAGAAGTTGA

Tumor necrosis factor-alpha (TNF)-308 TNF1/TNF1 polymorphism.

GCTAGATGAAGAGCAAGCGCACCTGGTCCCCAAAAGAAAT

TACAACCGACAGATGTATGTAAAGTTGGGGACACACAAGC

Transforming Growth Factor beta TGF beta1 (rare C allele in codon 25)

GCTAGATGAAGAGCAAGCGCCGAGGCCCTCCTACCTTTT

TACAACCGACAGATGTATGTTCGATAGTCTTGCAGGTGGA

Interleukin-10 gene (IL-10) -1087 AA polymorphism.

GCTAGATGAAGAGCAAGCGCTTCCCCAGGTAGAGCAACAC

TACAACCGACAGATGTATGTGATGGGGTGGAAGAAGTTGA

N-Acetyltransferase 2 (arylamine N-acetyltransferase) NAT2 282C>T polymorphism.

GCTAGATGAAGAGCAAGCGCCCTGCCAAAGAAGAAACACC

TACAACCGACAGATGTATGTGATGAAGCCCACCAAACAGT

N-Acetyltransferase 2 (arylamine N-acetyltransferase) NAT2 590G>A polymorphism.

GCTAGATGAAGAGCAAGCGCACTGGGCTCTGACCACAATC

TACAACCGACAGATGTATGTGGCTGATCCTTCCCAGAAAT

Thiopurine methyltransferase (TPMT) G460A polymorphism.

FIGURE 3 (Cont.)

GCTAGATGAAGAGCAAGCGCCCAGGTCCACACATTCCTCT

TACAACCGACAGATGTATGTTTACCATTTGCGATCACCTG

Thiopurine methyltransferase (TPMT) A719G polymorphism.

GCTAGATGAAGAGCAAGCGCCCAGGTCCACACATTCCTCT

TACAACCGACAGATGTATGTTTACCATTTGCGATCACCTG

Fc receptor-like protein 3 (FCRL3) -C196T polymorphism.

GCTAGATGAAGAGCAAGCGCGGGTGGAACCTCTTTGATT

TACAACCGACAGATGTATGTGCTTAATGAGCGTGGTGTGA

Tapasin gene (TPSN) Arg260Thr polymorphism.

GCTAGATGAAGAGCAAGCGCTGGGTAAGGGACATCTGCTC

TACAACCGACAGATGTATGTCAGATAGGTGCCCTCCTGAA

Toll-Like Receptor 4 (TLR4) Asp299Gly polymorphism.

GCTAGATGAAGAGCAAGCGCCTCTAGAGGGCCTGTGCAAT

TACAACCGACAGATGTATGTTCAATGTGGGAAACTGTCCA

Solute Carrier Family 19 ( folate reductase ) SLC19A1 G80A

GCTAGATGAAGAGCAAGCGCAGGCACAGTGTCACCTTCGT

TACAACCGACAGATGTATGTGCCGTAGAAGCAAAGGTAGC

Histocompatibility Antigen Hla 76 polymorphisms.

GCTAGATGAAGAGCAAGCGCGCACAATTCAACACCTCTGC

TACAACCGACAGATGTATGTCTGCAACCTTCCACTGTCCT

Histocompatibility Antigen Hla 78 polymorphisms.

GCTAGATGAAGAGCAAGCGCGATCTGCAGAGCCATCTTCC

TACAACCGACAGATGTATGTTGAGGTCCTTCAGCTCCAGT

Melatonin Receptor 1B (MTNR1B) polymorphism.

GCTAGATGAAGAGCAAGCGCGCAGAAGAGCCCAACTCCTT

TACAACCGACAGATGTATGTTGCATGTGTGGTTGTGATTG

FIGURE 3 (Cont.)

Major Histocompatibility Complex, class II, Transactivator (MHC2TA) polymorphism.

GCTAGATGAAGAGCAAGCGCAAGGTTCCCCCAACAGACTT

TACAACCGACAGATGTATGTCAAGCTAAGCCAACATGCAA

BETA-2-Adrenergic Receptor polymorphism.

GCTAGATGAAGAGCAAGCGCGCTCACCTGCCAGACTGC

GCTAGATGAAGAGCAAGCGCGCCAGGACGATGAGAGACAT

Monocyte chemotactic protein 1 (MCP1) polymorphism (-2518)G>A polymorphism.

GCTAGATGAAGAGCAAGCGCCCAGCCAAATGCATTCTCTT

TACAACCGACAGATGTATGTCACAGGGAAGGTGAAGGGTA

FAS LIGAND gene minus 843C/T polymorphism.

GCTAGATGAAGAGCAAGCGCCTTGAGCCCAGGAGTTTGAG

TACAACCGACAGATGTATGTATCAGAGGCTGCAAACCAGT

The Inflammatory Bowel Disease gene IBD5 locusIGR2060a_1 polymorphism.

GCTAGATGAAGAGCAAGCGCCATACAGCACCTTCGGGTCT

TACAACCGACAGATGTATGTGGGCAGACTTTGGAACTCAG

The cd16a gene V158F (G/T) polymorphism.

GCTAGATGAAGAGCAAGCGC CCAAAAGCCACACTCAAAGAC

TACAACCGACAGATGTATGT CTTGAGTGATGGTGATGTTCA

The Interleukin 1 beta (IL1b) minus 511a/c polymorphism.

GCTAGATGAAGAGCAAGCG CAGGCAGAGAGGGAAGGAGAG

TACAACCGACAGATGTATGT AAACAGCGAGGGAGAAACTG

The Interleukin 4 (IL4) 34c/t polymorphism.

GCTAGATGAAGAGCAAGCGCTCATTTTCCCTCGGTTTCAG

TACAACCGACAGATGTATGTAGAACAGAGGGGGAAGCAGT

The Caspase 9 C93T polymorphism.

GCTAGATGAAGAGCAAGCGCGCGGCCTGGAGTCTTAGTT

FIGURE 3 (Cont.)

TACAACCGACAGATGTATGTGATCATATGGGGCCTGAACA

The Adhesion Molecule 1 (ICAM1) R241G polymorphism.

GCTAGATGAAGAGCAAGCGCGAATGAAATGCCCCAGAGAA

TACAACCGACAGATGTATGTACTGTGGGGTTCAACCTCTG

The Interleukin 4 (IL4) gene -590 polymorphism.

GCTAGATGAAGAGCAAGCGACCCAAACTAGGCCTCACCT

TACAACCGACAGATGTATGTACAGGTGGCATCTTGGAAAC

The THIOPURINE S-METHYLTRANSFERASE 5 (TPMT5) gene T145C (Leu49Ser) polymorphism.

GCTAGATGAAGAGCAAGCGCCACTGACTGGGTGTGTGTC

TACAACCGACAGATGTATGTCCTCAGTCCACTCTTGCCTTT

The THIOPURINE S-METHYLTRANSFERASE 6 (TPMT6) gene A539T polymorphism.

GCTAGATGAAGAGCAAGCGCTTCCTTCCCTGCCTTTTGT

TACAACCGACAGATGTATGTCCCAACAACTTTACCTGGATG

The THIOPURINE S-METHYLTRANSFERASE 7 (TPMT7) gene T681G (His227Gln) polymorphism.

GCTAGATGAAGAGCAAGCGCCATCCATTACATTTTCAGGCTTT

TACAACCGACAGATGTATGTGGTTGATGCTTTTGAAGAACG

The THIOPURINE S-METHYLTRANSFERASE 8 (TPMT8) gene G644A (Arg215His) polymorphism.

GCTAGATGAAGAGCAAGCGTCCTGACCTCAAGTGATCCA

TACAACCGACAGATGTATGTCGTTCTTCAAAAGCATCAACC

The N-Acetyltransferase 2 (arylamine N-acetyltransferase) 341T>C polymorphism.

GCTAGATGAAGAGCAAGCGTGGTGTCTCCAGGTCAATCA

TACAACCGACAGATGTATGTGGCTGATCCTTCCCAGAAAT

The N-Acetyltransferase 2 (arylamine N-acetyltransferase) 481C>T polymorphism.

GCTAGATGAAGAGCAAGCGTGACGGCAGGAATTACATTG

TACAACCGACAGATGTATGTTGTTTCTTCTTTGGCAGGAGA

FIGURE 3 (Cont.)

The N-Acetyltransferase 2 (arylamine N-acetyltransferase) 803A>G polymorphism.

GCTAGATGAAGAGCAAGCGCCTGCCAAAGAAGAAACACC

TACAACCGACAGATGTATGTCGTGAGGGTAGAGAGGATATCTG

The N-Acetyltransferase 2 (arylamine N-acetyltransferase) 857G>A polymorphism.

GCTAGATGAAGAGCAAGCGCCTGCCAAAGAAGAAACACC

TACAACCGACAGATGTATGTCGTGAGGGTAGAGAGGATATCTG

The N-Acetyltransferase 2 (arylamine N-acetyltransferase) 191G>A polymorphism.

GCTAGATGAAGAGCAAGCGCCATGGAGTTGGGCTTAGAG

TACAACCGACAGATGTATGTCCATGCCAGTGCTGTATTTG

The Lectin, Mannose-binding (MBL) gene Gly54Asp polymorphism.

GCTAGATGAAGAGCAAGCGTGGCAGCGTCTTACTCAGAA

TACAACCGACAGATGTATGTAGAACAGCCCAACACGTACC

Histocompatibility Antigen Hla B27 polymorphism.

GCTAGATGAAGAGCAAGCGCGCTACGTGGACGACACGCT

TACAACCGACAGATGTATGTCAGTCTGTGCCTTGGCGTTGC

Figure 4A: Table 4

Equation variables

| | | B | E.T. | Wald | gl | Sig. | Exp(B) | I.C. 95,0% for EXP(B) | |
|---|---|---|---|---|---|---|---|---|---|
| | | | | | | | | Inferior | Superior |
| Step 1 | ANTI_PCC | ,001 | ,000 | 4,890 | 1 | ,027 | 1,001 | 1,000 | 1,002 |
| | VSG | ,021 | ,010 | 4,661 | 1 | ,031 | 1,021 | 1,002 | 1,041 |
| | @8REC(1) | ,797 | ,532 | 2,247 | 1 | ,134 | 2,220 | ,782 | 6,297 |
| | @40REC(1) | 1,027 | ,640 | 2,572 | 1 | ,109 | 2,792 | ,796 | 9,795 |
| | @78REC(1) | 1,651 | ,790 | 4,365 | 1 | ,037 | 5,211 | 1,108 | 24,513 |
| | Constant | -5,839 | 1,067 | 29,940 | 1 | ,000 | ,003 | | |
| Step 2 | ANTI_PCC | ,001 | ,000 | 5,919 | 1 | ,015 | 1,001 | 1,000 | 1,002 |
| | VSG | ,023 | ,010 | 5,803 | 1 | ,016 | 1,023 | 1,004 | 1,043 |
| | @40REC(1) | 1,130 | ,624 | 3,286 | 1 | ,070 | 3,097 | ,912 | 10,511 |
| | @78REC(1) | 1,680 | ,786 | 4,572 | 1 | ,032 | 5,366 | 1,150 | 25,029 |
| | Constant | -5,748 | 1,073 | 28,705 | 1 | ,000 | ,003 | | | a. Variable(s) introduced on step1: ANTI_PCC, VSG, @8REC, @40REC, @78REC.

Figure 5A: Table 5

Equation Variables

| | | B | E.T. | Wald | gl | Sig. | Exp(B) |
|---|---|---|---|---|---|---|---|
| Step 1 | A_PCC_BI(1) | 2.784 | .585 | 22.614 | 1 | .000 | 16.187 |
| | Constante | -3.725 | .506 | 54.228 | 1 | .000 | .024 |
| Step 2 | A_PCC_BI(1) | 2.842 | .593 | 22.968 | 1 | .000 | 17.156 |
| | @41(1) | 2.034 | 1.065 | 3.649 | 1 | .056 | 7.648 |
| | Constant | -5.520 | 1.140 | 23.462 | 1 | .000 | .004 |
| Step 3 | A_PCC_BI(1) | 2.892 | .602 | 23.114 | 1 | .000 | 18.030 |
| | @41(1) | 2.012 | 1.074 | 3.509 | 1 | .061 | 7.476 |
| | @28_REC(1) | 1.994 | 1.075 | 3.437 | 1 | .064 | 7.344 |
| | Constant | -7.256 | 1.547 | 21.999 | 1 | .000 | .001 | a. Variable(s) introduced on the step 1: A_PCC_BI.
b. Variable(s) introduced on the step 2: @41.
c. Variable(s) introduced on the step 3: @28_REC.

Figure 6A: Table 6

Equation Variables

| | | B | E.T. | Wald | gl | Sig. | Exp(B) |
|---|---|---|---|---|---|---|---|
| Step 1[a] | @20 | | | 10.165 | 2 | .006 | |
| | @20(1) | -.987 | .472 | 4.377 | 1 | .036 | .373 |
| | @20(2) | -2.175 | .706 | 9.489 | 1 | .002 | .114 |
| | @26 | | | .778 | 2 | .678 | |
| | @26(1) | -.384 | .459 | .698 | 1 | .403 | .681 |
| | @26(2) | -9.082 | 31.635 | .082 | 1 | .774 | .000 |
| | @14 | | | 4.844 | 2 | .089 | |
| | @14(1) | .976 | .447 | 4.769 | 1 | .029 | 2.654 |
| | @14(2) | -8.422 | 31.897 | .070 | 1 | .792 | .000 |
| | @15 | | | 5.454 | 2 | .065 | |
| | @15(1) | -1.114 | .478 | 5.425 | 1 | .020 | .328 |
| | @15(2) | -7.793 | 44.305 | .031 | 1 | .860 | .000 |
| | A_PCC_BI(1) | 2.059 | .770 | 7.160 | 1 | .007 | 7.840 |
| | NºARTDOL | .108 | .032 | 11.416 | 1 | .001 | 1.114 |
| | Constant | -2.414 | .948 | 6.481 | 1 | .011 | .089 | a. Variable(s) introduced on step 1: @20, @26, @14, @15, A_PCC_BI, NºARTDOL

Figure 7A: Table 7

Equation Variables

| | | B | E.T. | Wald | gl | Sig. | Exp(B) |
|---|---|---|---|---|---|---|---|
| Step 1 | @27 | | | 6.158 | 2 | .046 | |
| | @27(1) | .288 | .281 | 1.052 | 1 | .305 | 1.334 |
| | @27(2) | 1.314 | .534 | 6.061 | 1 | .014 | 3.720 |
| | @16 | | | 5.916 | 2 | .052 | |
| | @16(1) | .665 | .278 | 5.700 | 1 | .017 | 1.944 |
| | @16(2) | .006 | .613 | .000 | 1 | .993 | 1.006 |
| | @73 | | | 7.101 | 2 | .029 | |
| | @73(1) | .523 | .275 | 3.632 | 1 | .057 | 1.688 |
| | @73(2) | -1.026 | .693 | 2.192 | 1 | .139 | .358 |
| | EDADDEBU | -.024 | .011 | 5.117 | 1 | .024 | .976 |
| | A_PCC_BI(1) | .419 | .333 | 1.585 | 1 | .208 | 1.520 |
| | FR | .001 | .001 | 4.409 | 1 | .036 | 1.001 |
| | PCR | .091 | .043 | 4.537 | 1 | .033 | 1.095 |
| | Constant | -.434 | .617 | .495 | 1 | .482 | .648 | a. Variable(s) introduced on step 1: @27, @16, @73, EDADDEBU, A_PCC_BI, FR, PCR.

Figure 8A: Table 8

Equation Variables

| | | B | E.T. | Wald | gl | Sig. | Exp(B) |
|---|---|---|---|---|---|---|---|
| Step 1 | @2 | | | 5.694 | 2 | .058 | |
| | @2(1) | -.046 | .342 | .018 | 1 | .892 | .955 |
| | @2(2) | .940 | .431 | 4.761 | 1 | .029 | 2.559 |
| | @32 | | | 4.818 | 2 | .090 | |
| | @32(1) | .678 | .316 | 4.613 | 1 | .032 | 1.970 |
| | @32(2) | -6.640 | 15.264 | .189 | 1 | .664 | .001 |
| | @29 | | | 4.048 | 2 | .132 | |
| | @29(1) | .662 | .335 | 3.910 | 1 | .048 | 1.939 |
| | @29(2) | .232 | .535 | .188 | 1 | .664 | 1.262 |
| | @12 | | | 5.972 | 2 | .050 | |
| | @12(1) | .004 | .353 | .000 | 1 | .991 | 1.004 |
| | @12(2) | 2.915 | 1.196 | 5.947 | 1 | .015 | 18.457 |
| | A_PCC_BI(1) | .473 | .396 | 1.425 | 1 | .233 | 1.605 |
| | VSG | .007 | .006 | 1.467 | 1 | .226 | 1.007 |
| | Constant | -2.886 | .532 | 29.477 | 1 | .000 | .056 | a. Variable(s) introduced on step 1: @2, @32, @29, @12, A_PCC_BI, VSG.

Figure 9A: Table 9

Equation Variables

| | | B | E.T. | Wald | gl | Sig. | Exp(B) |
|---|---|---|---|---|---|---|---|
| Step 1[a] | @32REC(1) | -.934 | .375 | 6.196 | 1 | .013 | .393 |
| | Constante | -.234 | .217 | 1.158 | 1 | .282 | .792 |
| Step 2[b] | @32REC(1) | -.947 | .395 | 5.729 | 1 | .017 | .388 |
| | @50 | | | 7.129 | 2 | .028 | |
| | @50(1) | -.134 | .408 | .108 | 1 | .743 | .875 |
| | @50(2) | 1.213 | .529 | 5.262 | 1 | .022 | 3.364 |
| | Constante | -.381 | .295 | 1.669 | 1 | .196 | .683 |
| Step 3[c] | @32REC(1) | -.914 | .406 | 5.065 | 1 | .024 | .401 |
| | @42(1) | 1.588 | .626 | 6.430 | 1 | .011 | 4.892 |
| | @50 | | | 8.797 | 2 | .012 | |
| | @50(1) | -.359 | .431 | .693 | 1 | .405 | .698 |
| | @50(2) | 1.228 | .530 | 5.365 | 1 | .021 | 3.413 |
| | Constant | -.475 | .301 | 2.496 | 1 | .114 | .622 | a. Variable(s) introduced on step 1: @32REC.
b. Variable(s) introduced on step 2: @50.
c. Variable(s) introduced on step 3: @42.

Figure 10A: Table 10

Equation Variables

| | | B | E.T. | Wald | gl | Sig. | Exp(B) |
|---|---|---|---|---|---|---|---|
| Step 1a | EDADDEBU | -.032 | .012 | 6.674 | 1 | .010 | .969 |
| | Constant | .041 | .572 | .005 | 1 | .943 | 1.042 |
| Step 2b | @50 | | | 9.025 | 2 | .011 | |
| | @50(1) | .443 | .379 | 1.365 | 1 | .243 | 1.557 |
| | @50(2) | 1.440 | .482 | 8.910 | 1 | .003 | 4.219 |
| | EDADDEBU | -.033 | .012 | 6.856 | 1 | .009 | .968 |
| | Constant | -.381 | .633 | .362 | 1 | .548 | .683 | a. Variable(s) introduced on step 1 : EDADDEBU.
b. Variable(s) introduced on step 2: @50.

Figure 11A: Table 11A

| Variable | 1 HAQ>2 | 2 Multiple erosions (RX2) | 3 >3 Different treatments (TTO_3OM) | 4 Leaving the job | 5 Surgical intervention | 6 Methotrexate intolerance (Therapy response) | 7 Remission |
|---|---|---|---|---|---|---|---|
| SNPs (rs Identifier) | | | | | | | |
| GSTM1 (not avail) | | | | | | | null allele |
| FGB (rs1800790) | A | | | | | | |
| IL4 (rs2070874) | T | | | | | | T |
| PTPN22 (rs2476601) | | | | | | | |
| VDR (rs1544410) | | G | | | | | |
| NFKBIL1 (rs2071592) | | T | | | | | |
| IL18 (rs187238) | | G | | | | | |
| IL4R (rs1801275) | | A | A | | | | |
| PARP1 (rs7531668) | | | T | | | | |
| IL1RN (rs4419598) | | | C | | | | |
| MCP1 (rs1024611) | | | | | T | | |
| RUNX1 (rs2268277) | | | | G | G | | |
| TP53 (rs1042522) | | | | | A | | |
| VDR (rs10735810) | | | | | T | | |
| VEGF (rs3025039) | | | | null allele | | | |
| GSTT1 (not avail) | | | | T | | | |
| MTHFR (rs1801133) | | | | | | T | |
| Clinical | | | | | | | |
| ANTI-PCC | high levels –high risk | | high levels –high risk | | | | |
| ANTI-PCC BI | | Presence –high risk | | | Presence –high risk | | Presence –low probability |
| VSG | high levels-high risk | | | | high levels-high risk | | |
| NoARTDOL | | high number-high risk | | | | | |
| RF | | | high levels-high risk | | | | |
| PCR | | | high levels-high risk | | | | |
| Onset age | | | Earlier onset is associated with 3 or more treatments | | | Earlier onset is associated with intolerance | |

Figure 11B: Table 11B

| SNP# | Gene Symbol | Gene Name | Polymorphism | ID (rs) |
|---|---|---|---|---|
| 41 | GSTM1 | Glutathione S-transferase M1 | null allele | not available |
| 40 | FGB | Fibrinogen B beta polypeptide | G455A | rs1800790 |
| 78 | IL4 | Interleukin 4 | C34T | rs2070874 |
| 28 | PTPN22 | Prot-tyr phosphatase, non-receptor 2 | 1858C/T | rs2476601 |
| 20 | VDR | Vitamin D receptor | AposVS7+283(b>B) | rs1544410 |
| 26 | NFKBIL1 | NF of k light pp enh B cells inh-like 1 | T-62A | rs2071592 |
| 14 | IL18 | Interleukin 18 | G-137C | rs187238 |
| 15 | IL4R | Interleukin 4 Receptor | Q551R | rs1801275 |
| 27 | PARP1 | Poly ADP-ribose polymerase 1 | C1362T | rs7531668 |
| 16 | IL1RN | The IL-1 receptor antagonist | T2018C(IL-1RN*1) (-2518)G>A | rs419598 |
| 73 | MCP1 | Monocyte chemotactic protein 1 | G2677T | rs1024611 |
| 2 | RUNX1 | Runt-related Transcription Factor 1 | codón 72 | rs2268277 |
| 32 | TP53 | Tumor Protein p53 | Fok1 | rs1042522 |
| 29 | VDR | Vitamin D receptor | C936T | rs10735810 |
| 12 | VEGF | Vascular Endothelial Growth Factor | null allele | rs3025039 |
| 42 | GSTT1 | Glutathione S-transferase T1 | C677T | not available |
| 50 | MTHFR | Methylenetetrahydrofolate Reductase | | rs1801133 |

Figure 12: Table 12

| Phenotype and SNPs | P value |
|---|---|
| HAQ>2 | |
| SNP 78 (rs2070874) | 0,01723806 |
| SNP 89 (rs1041983) | 0,01859894 |
| SNP 40 (rs1800790) | 0,01905114 |
| SNP 87 (rs not available) | 0,0480329 |
| RX2 | |
| SNP 42 (rs not available) | 0,00351956 |
| SNP 26 (rs2071592) | 0,02199691 |
| SNP 15 (rs1801275) | 0,03075416 |
| SNP 34 (rs1800629) | 0,03181104 |
| TTO_3 | |
| SNP 20 (rs1544410) | 0,00625435 |
| SNP 87 (rs not available) | 0,04457328 |
| Surgical Intervention | |
| SNP 41 (rs not available) | 0,01281179 |
| Remission | |
| SNP 87 (rs not available) | 0,02296336 |
| SNP 28 (rs2476601) | 0,0237744 |
| SNP 27 (rs7531668) | 0,02581015 |
| Leaving the job | |
| SNP 32 (rs1042522) | 0,0350 |
| Methotrexate intolerance | |
| SNP 50 (rs1801133) | 0,0100 |
| SNP 58 (rs2842934) | 0,0360 |
| SNP 78 (rs2070874) | 0,0270 |

## METHODS OF PROGNOSING A RHEUMATOID ARTHRITIS REMISSION PHENOTYPE

RELATED APPLICATIONS

This application is related to GB Patent Application No. 0613844.0, filed 12 Jul. 2006, the contents of which are incorporated herein by reference in their entirety.

This application is a national stage filing under 35§371 of PCT International application PCT/IB2007/002366 designating the United States of America, and filed Jul. 12, 2007, the entire contents of which are hereby incorporated herein by reference. This application claims the benefit under 35 U.S.C. §119 from Application No. GB 0613844.0, filed in the United Kingdom on Jul. 12, 2006, the entire contents of which are hereby incorporated herein by reference.

FIELD OF THE INVENTION

The invention relates to methods and products in particular, microarrays for in vitro genotyping of Rheumatoid Arthritis (RA) associated genetic variations. The invention further relates to methods for the prognosis and treatment of RA, and to products for use therein.

BACKGROUND TO THE INVENTION

Rheumatoid Arthritis (RA) is a chronic inflammatory disorder, which characteristically has joint involvement. The prevalence is about 0.8% (approximately 2.9 million people in Europe) with some variation among ethnic groups. RA is more common in women than men.

In the RA disease process, inflammation involves the synovium and may cause damage to the cartilage and bone itself. Areas that may be affected include the joints of the hands, wrists, neck, jaw, elbows, feet, and ankles. Often RA causes the joints of the body to be affected in a symmetrical manner, meaning that the disease attacks the same joint on both sides of the body—for example, both hands.

Diagnosis of RA is currently made according to the criteria set out by the American College of Rheumatology in 1987 (published in Arnett et al., Arthritis and Rheumatism March 1988; 31(3):315-24).

A number of pharmacological agents are commonly used to manage the signs and symptoms of RA. These fall into four main classes: NSAIDs (nonsteroidal anti-inflammatory drugs) that relieve the pain and inflammation associated with RA; DMARDs (disease-modifying antirheumatic drugs) that both relieve symptoms and help to control RA by modifying its disease process); Glucocorticoids (a group of anti-inflammatory drugs that are related to cortisol, a natural steroid hormone produced by the body); and Biologicals (drugs like Kineret® (anakinra) that are designed to target specific molecules in the immune system that contribute to the RA disease process.

Epidemiologic and genetic studies have provided evidence of the presence of genetic susceptibility factors for RA, accounting for approximately 60% of the variation in liability to disease. Identification of those genes related to RA could bring a better understanding of the pathogenesis, diagnosis, location, and prognosis and eventually appropriate adequate treatment. From a clinical point of view, early diagnosis, prognosis and location of the disease would signify an important change in therapeutic decisions used for treatment.

Association studies have recently identified several genes in which one or more genetic variations result in a higher or lower risk of contracting this disease, a better or worse response to drugs and/or, a better or worse prognosis. A means of characterising multiple RA associated variations which could be used clinically would provide a great advance in diagnosis and therapy.

DNA-chips are often used to discriminate between alleles at genetic loci.

In 2001, the Consortium for the Human Genome Project and the private company Cetera presented the first complete example of the human genome with 30,000 genes. From this moment on, the possibility of studying the complete genome or large scale (high-throughput) studies began. So-called "DNA-chips", also named "micro-arrays", "DNA-arrays" or "DNA bio-chips" are apparatus that functional genomics can use for large scale studies. Functional genomics studies changes in the expression of genes due to environmental factors and to genetic characteristics of an individual. Gene sequences present small interindividual variations at one unique nucleotide called an SNP ("single nucleotide polymorphism"), which in a small percentage are involved in changes in the expression and/or function of genes that cause certain pathologies. The majority of studies which apply DNA-chips study gene expression, although chips are also used in the detection of SNPs.

The first DNA-chip was the "Southern blot" where labelled nucleic acid molecules were used to examine nucleic acid molecules attached to a solid support. The support was typically a nylon membrane.

Two breakthroughs marked the definitive beginning of DNA-chip. The use of a solid non-porous support, such as glass, enabled miniaturisation of arrays thereby allowing a large number of individual probe features to be incorporated onto the surface of the support at a density of >1,000 probes per $cm^2$. The adaptation of semiconductor photolithographic techniques enabled the production of DNA-chips containing more than 400,000 different oligonucleotides in a region of approximately 20 $\mu m^2$, so-called high density DNA-chips.

In general, a DNA-chip comprises a solid support, which contains hundreds of fragments of sequences of different genes represented in the form of DNA, cDNA or fixed oligonucleotides, attached to the solid surface in fixed positions. The supports are generally glass slides for the microscope, nylon membranes or silicon "chips". It is important that the nucleotide sequences or probes are attached to the support in fixed positions as the robotized localisation of each probe determines the gene whose expression is being measured. DNA-chips can be classified as:

high density DNA-chips: the oligonucleotides found on the surface of the support, e.g. glass slides, have been synthesized "in situ", by a method called photolithography.

low density DNA-chips: the oligonucleotides, cDNA or PCR amplification fragments are deposited in the form of nanodrops on the surface of the support, e.g. glass, by means of a robot that prints those DNA sequences on the support. There are very few examples of low density DNA-chips which exist: a DNA-chip to detect 5 mutations in the tyrosinase gene; a DNA-chip to detect mutations in p53 and k-ras; a DNA-chip to detect 12 mutations which cause hypertrophic cardiomypathy; a DNA-chip for genotyping of *Escherichia coli* strains; or DNA-chips to detect pathogens such as *Cryptosporidium parvum* or rotavirus.

For genetic expression studies, probes deposited on the solid surface, e.g. glass, are hybridized to cDNAs synthesized from mRNAs extracted from a given sample. In general the cDNA has been labelled with a fluorophore. The larger the number of cDNA molecules joined to their complementary sequence in the DNA-chip, the greater the intensity of the fluorescent signal detected, typically measured with a laser. This measure is therefore a reflection of the number of mRNA molecules in the analyzed sample and consequently, a reflection of the level of expression of each gene represented in the DNA-chip.

Gene expression DNA-chips typically also contain probes for detection of expression of control genes, often referred to as "house-keeping genes", which allow experimental results to be standardized and multiple experiments to be compared in a quantitive manner. With the DNA-chip, the levels of expression of hundreds or thousands of genes in one cell can be determined in one single experiment. cDNA of a test sample and that of a control sample can be labelled with two different fluorophores so that the same DNA-chip can be used to study differences in gene expression.

DNA-chips for detection of genetic polymorphisms, changes or mutations (in general, genetic variations) in the DNA sequence, comprise a solid surface, typically glass, on which a high number of genetic sequences are deposited (the probes), complementary to the genetic variations to be studied. Using standard robotic printers to apply probes to the array a high density of individual probe features can be obtained, for example probe densities of 600 features per $cm^2$ or more can be typically achieved. The positioning of probes on an array is precisely controlled by the printing device (robot, inkjet printer, photolithographic mask etc) and probes are aligned in a grid. The organisation of probes on the array facilitates the subsequent identification of specific probe-target interactions. Additionally it is common, but not necessary to divide the array features into smaller sectors, also grid-shaped, that are subsequently referred to as sub-arrays. Sub-arrays typically comprise 32 individual probe features although lower (e.g. 16) or higher (e.g. 64 or more) features can comprise each subarray.

One strategy used to detect genetic variations involves hybridization to sequences which specifically recognize the normal and the mutant allele in a fragment of DNA derived from a test sample. Typically, the fragment has been amplified, e.g. by using the polymerase chain reaction (PCR), and labelled e.g. with a fluorescent molecule. A laser can be used to detect bound labelled fragments on the chip and thus an individual who is homozygous for the normal allele can be specifically distinguished from heterozygous individuals (in the case of autosomal dominant conditions then these individuals are referred to as carriers) or those who are homozygous for the mutant allele.

Another strategy to detect genetic variations comprises carrying out an amplification reaction or extension reaction on the DNA-chip itself.

For differential hybridisation based methods there are a number of methods for analysing hybridization data for genotyping:

Increase in hybridization level: The hybridization level of complementary probes to the normal and mutant alleles are compared.

Decrease in hybridization level: Differences in the sequence between a control sample and a test sample can be identified by a fall in the hybridization level of the totally complementary oligonucleotides with a reference sequence. A complete loss is produced in mutant homozygous individuals while there is only 50% loss in heterozygotes. In DNA-chips for examining all the bases of a sequence of "n" nucleotides ("oligonucleotide") of length in both strands, a minimum of "2n" oligonucleotides that overlap with the previous oligonucleotide in all the sequence except in the nucleotide are necessary. Typically the size of the oligonucleotides is about 25 nucleotides. The increased number of oligonucleotides used to reconstruct the sequence reduces errors derived from fluctuation of the hybridization level. However, the exact change in sequence cannot be identified with this method; sequencing is later necessary in order to identify the mutation.

Where amplification or extension is carried out on the DNA-chip itself, three methods are presented by way of example:

In the Minisequencing strategy, a mutation specific primer is fixed on the slide and after an extension reaction with fluorescent dideoxynucleotides, the image of the DNA-chip is captured with a scanner.

In the Primer extension strategy, two oligonucleotides are designed for detection of the wild type and mutant sequences respectively. The extension reaction is subsequently carried out with one fluorescently labelled nucleotide and the remaining nucleotides unlabelled. In either case the starting material can be either an RNA sample or a DNA product amplified by PCR.

In the Tag arrays strategy, an extension reaction is carried out in solution with specific primers, which carry a determined 5' sequence or "tag". The use of DNA-chips with oligonucleotides complementary to these sequences or "tags" allows the capture of the resultant products of the extension. Examples of this include the high density DNA-chip "Flex-flex" (Affymetrix).

For genetic diagnosis, simplicity must be taken into account. The need for amplification and purification reactions presents disadvantages for the on-chip extension/amplification methods compared to the differential hybridization based methods.

Typically, DNA-chip analysis is carried out using differential hybridization techniques. However, differential hybridization does not produce as high specificity or sensitivity as methods associated with amplification on glass slides. For this reason the development of mathematical algorithms, which increase specificity and sensitivity of the hybridization methodology, are needed (Cutler D J, Zwick M E, Carrasquillo M N, Yohn C T, Tobi K P, Kashuk C, Mathews D J, Shah N, Eichler E E, Warrington J A, Chakravarti A. Genome Research; 11:1913-1925 (2001).

Thus, despite advances in technology, the problems of existing methods is simultaneously analysing a large number of genetic variations in a sensitive, specific and reproducible way, has prevented the application of DNA-chips for routine use in clinical diagnosis.

SUMMARY OF THE INVENTION

The inventors have identified new means for prognosing RA phenotypes using combinations of informative SNP variables and clinical variables. Accordingly the invention provides a method of prognosing a rheumatoid arthritis (RA) phenotype in a subject, which comprises:
(I) obtaining outcomes for one or more single nucleotide polymorphism variables and one or more clinical variables listed in Table 11A for the subject; and
(II) using the outcomes obtained in (I) to prognose the phenotype;
wherein
(i) an outcome for an SNP variable is the identity of the nucleotide in the genomic DNA of the subject at the position of the single nucleotide polymorphism;

(ii) an outcome for the clinical variable ANTI-PCC is the level of anti-cyclic citrullinated peptide antibody in the serum of the subject;
(iii) an outcome for the clinical variable ANTI-PCC BI is a binary representation of the level of anti-cyclic citrullinated peptide antibody in the serum of the subject;
(iv) an outcome for the clinical variable VSG is the erythrocyte sedimentation rate in the blood of the subject;
(v) an outcome for the clinical variable NoARTDOL is the number of painful joints referred by the subject;
(vi) an outcome for the clinical variable RF is the level of Rheumatoid Factor antibody in the serum of the subject;
(vii) an outcome for the clinical variable PCR is the level of C-reactive protein in the blood; and
(viii) an outcome for the clinical variable onset age is the age in years at which the subject was diagnosed with RA;
and wherein:
(a) the RA phenotype is a health assessment questionnaire (HAQ) score of >2 (HAQ>2) and the variables for which outcomes are obtained in step (I) comprise the HAQ>2 SNP and clinical variables in Table 11A; and/or
(b) the RA phenotype is presence of multiple of erosions in the hands and feet (RX2) and the variables for which outcomes are obtained in step (I) comprise the RX2 SNP and clinical variables in Table 11A; and/or
(c) the RA phenotype is receiving 3 or more different treatments (TTO_30M) and the variables for which outcomes are obtained in step (I) comprise the TTO_30M SNP and clinical variables in Table 11A; and/or
(d) the RA phenotype is being forced to leave employment because of RA (leaving the job) and the variables for which outcomes are obtained in step (I) comprise the "leaving the job" SNP and clinical variables in Table 11A; and/or
(e) the RA phenotype is receiving an articular prosthesis (surgical intervention) and the variables for which outcomes are obtained in step (I) comprise the "surgical intervention" SNP and clinical variables in Table 11A; and/or
(f) the RA phenotype is methotrexate intolerance and the variables for which outcomes are obtained in step (I) comprise the "methotexate intolerance" SNP and clinical variables in Table 11A; and/or
(g) the RA phenotype is remission and the variables for which outcomes are obtained in step (I) comprise the "remission" SNP and clinical variables in Table 11A.

The invention also provides a method of deriving a probability function for use in prognosing an RA phenotype, a computational method of deriving a probability function for use in prognosing an RA phenotype and a method for prognosing an RA phenotype in a subject comprising use of a probability function derived using the data in any one of Tables 4 to 10, as set out in the claims.

The inventors have also identified SNPs which have significant allelic association with prostate cancer recurrence. Accordingly the invention also provides a method of prognosing an RA phenotype in a subject comprising determining the genotype of the subject at one or more positions of single nucleotide polymorphism selected from the SNPs in Table 12.

The invention also provides an in vitro method for genotyping RA associated genetic variations in an individual as set out in the claims.

Further aspects of the invention include a computational method for obtaining a genotype from DNA-chip hybridisation intensity data, a method of deriving linear functions for use in a genotyping method of the invention, a computational method of deriving linear functions for use in a genotyping method of the invention, a method of diagnosing RA or susceptibility to RA in an individual comprising genotyping an individual with respect to one or more genetic variations, methods for selecting a treatment for RA in a subject and for treating RA in a subject, a method of identifying genetic variations predictive of a particular RA phenotype and a method of predicting the likely development of a RA phenotype in an individual using the identified variation(s).

Still further aspects include a computer system comprising a processor and means for controlling the processor to carry out a computational method of the invention, a computer program comprising computer program code which when run on a computer or computer network causes the computer or computer network to carry out a computational method of the invention.

The invention also provides a DNA chip or micoarray suitable for use in the methods of the invention, an oligonucleotide probe, probe pair, or 4-probe set listed in Table 2 (FIG. 2), an oligonucleotide primer or primer pair listed in Table 3 (FIG. 3), a PCR amplification kit comprising at least one pair of the listed primers, a diagnostic kit for detection of RA associated genetic variations and a kit for prognosing an RA phenotype in a subject.

All of these aspects of the invention are as set out in the claims.

BRIEF DESCRIPTION OF THE SEQUENCES

SEQ ID NOS: 1-360 are probes suitable for detection of the RA associated genetic variations in Table 1 A (or Table 1 B). The probe sequences are shown in Table 2.

SEQ ID NOS: 361-540 are PCR primers suitable for amplifying target DNA regions comprising RA associated genetic variations listed in Table 1A (or Table 1B). The primer sequences are shown in Table 3.

SEQ ID NO: 541 is an external control nucleic acid.

SEQ ID NOS: 542 & 543 are probes suitable for detection of the external control nucleic acid of SEQ ID NO: 541.

SEQ ID NO: 544 is a forward TAG sequence.

SEQ ID NO: 545 is a reverse TAG sequence.

The Sequence Listing is submitted as an ASCII text file in the form of the file named Sequence_Listing.txt, which was created on Jun. 2, 2013, and is 82,415 bytes, which is incorporated by reference herein.

BRIEF DESCRIPTION OF THE DRAWINGS

FIG. 1

Figure 4B:
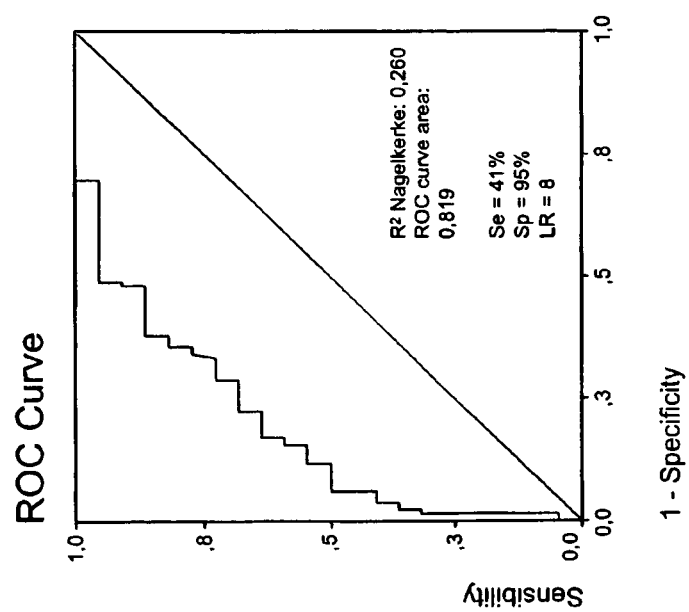

Tables 1A and 1B list genetic variations associated with RA which may be analysed according to the invention. The sequences of all the genes mentioned in Tables 1A and 1B are known and recognised on the following website: GeneBank (NcRI), GeneCard (Weizmann Institute of Sciences) and snpper.chip.org (Innate Immunity PLA).

Table 1A of GB Application No. 0613844.0, included an additional polymorphism, IL6-174 polymorphism. In one aspect Table 1A as used herein may additionally include this polymorphism.

FIG. 2

Table 2 lists oligonucleotide probes for discriminating between alleles at the SNPs listed in Tables 1A and 1B. The Table lists two probe pairs for each SNP (a four-probe set)

FIG. 3

Table 3 lists oligonucleotide primers for PCR amplification of each of the SNPs listed in Tables 1A and 1B.

FIG. 4

(A) Table 4 showing the two SNPs (40 and 78) and the 2 clinical variables (VSG and ANTI-PCC) together with their significance (Sig.) and their odds ratios (Exp (B)) used to compute the model for the prediction of the HAQ>2 phenotype. This model provides the probability to develop a HAQ>2 phenotype from 0 (no risk) to 1 (maximum risk).

(B) ROC (receiver operating characteristic) curve obtained for the model HAQ>2 that allows the estimation of its discriminatory power. The ROC curve has been calculated in order to maximize the specificity, thus reducing at the same time the "false" positive rate. A specificity of 95% with a sensibility of 41% is the cut-off for this model regarding the phenotype HAQ>2. This model shows a likelihood ratio (LR) value of 8.

FIG. 5

(A) Table 5 showing the two SNPs (28 and 41) and the clinical variable (ANTI-PCC BI) together with their significance (Sig.) and their odds ratios (Exp (B)) used to compute the model for the prediction of the phenotype REMISSION (the patient did not need any treatment in the last 5 years).

(B) ROC curve obtained for the model of the phenotype REMISSION. As shown by the curve, a sensibility of 71% and a specificity of 89% with a LR of 6.5 were obtained for this model.

FIG. 6

(A) Table 6 showing the four SNPs (14, 15, 20 and 26) and the two clinical variables (number of involved joints and ANTI-PCC BI) together with their significance (Sig.) and their odds ratios (Exp (B)) used to compute the model for the prediction of the phenotype RX2.

(B) ROC curve obtained for the model of the phenotype RX2. As shown by the curve, a sensibility of 41% and a specificity of 95% with a LR of 6.5 were obtained for this model.

FIG. 7

(A) Table 7 showing the three SNPs (16, 27 and 73) and the four clinical variables (and ANTI-PCC BI, FR, PCR and onset age) together with their significance (Sig.) and their odds ratios (Exp (B)) used to compute the model for the prediction of the phenotype TTO_30M.

(B) ROC curve obtained for the model of the phenotype TTO_30M. As shown by the curve, a sensibility of 31% and a specificity of 95% with a LR of 6.2 were obtained for this model.

FIG. 8

(A) Table 8 showing the four SNPs (2, 12, 29 and 32) and the two clinical variables (and ANTI-PCC and VSG) together with their significance (Sig.) and their odds ratios (Exp (B)) used to compute the model for the prediction of the phenotype surgical intervention.

(B) ROC curve obtained for the model of the phenotype surgical intervention. As shown by the curve, a sensibility of 23% and a specificity of 95% with a LR of 5.4 were obtained for this model.

FIG. 9

(A) Table 9 showing the three SNPs (32, 42 and 50) together with their significance (Sig.) and their odds ratios (Exp (B)) used to compute the model for the prediction of the phenotype "leaving the job".

(B) ROC curve obtained for the model of the phenotype "leaving the job". As shown by the curve, a sensibility of 10% and a specificity of 95% with a LR of 1.9 were obtained for this model.

FIG. 10

(A) Table 10 showing the SNP (50) and the clinical variable (onset age) together with their significance (Sig.) and their odds ratios (Exp (B)) used to compute the model for the prediction of the phenotype "therapy response".

(B) ROC curve obtained for the model of the phenotype "therapy response". As shown by the curve, a sensibility of 16% and a specificity of 96% with a LR of 4.3 were obtained for this model.

FIG. 11

(A) Table 11A shows the SNP variables and the clinical variables included in each of the models 1 to 7 described herein. The Table indicates which SNP variables and clinical variables (of those listed in the first column) are informative for determining each phenotype, and shows which outcome for each variable is associated with poor prognosis of phenotype.

(B) Table 11B provides more information including rs identifiers for the SNPs in Table 11A.

FIG. 12

Table 12 lists the allelic associations of individual SNPs with the RA phenotypes described herein.

DETAILED DESCRIPTION OF THE INVENTION

Rheumatoid arthritis (RA) presents a number of phenotypes, most notably in terms of disease severity. Mild disease is distinguished from severe and destructive disease, as well as the speed and nature of disease progression. This clinical heterogeneity is thought to correlate with genetic heterogeneity.

Using the Artchip of the present invention and clinical investigation, the inventors have identified a number of profiles (based on combinations of SNP and clinical variables) which are informative for predicting RA phenotypes. The inventors have thus established models for predicting the course of RA in RA patients. Accordingly, in one aspect, the present invention relates to methods for prognosis of RA.

For example, the invention relates to methods for predicting aggressive RA, as represented by one or more of the following phenotypes:

1. having a health assessment questionnaire of greater than 2;
2. having multiple erosions in hands and feet;
3. receiving 3 or more different treatments;
4. being obliged to leave one's job; and
5. a need for articular prosthesis (surgical intervention).

The invention also relates to methods for predicting response to therapy, in particular predicting methotrexate tolerance. The invention further relates to methods for predicting remission.

The inventors selected a study population of Spanish individuals, as in Example 2. Each individual was clinically assessed to determine the presence (yes) or absence (no) of each of seven phenotypes, namely phenotypes 1 to 5 above, phenotype of methotrexate intolerance, and the remission phenotype.

Each individual was also tested for baseline clinical and analytical variables, and genotyped at a number of genetic loci using the Artchip DNA microarray of the present invention (see Example 2). The inventors then used genetic analysis to select a subset of the most informative SNPs for further modelling. Statistical analysis was carried out to establish seven models (based on combinations of informative SNPs and informative clinical variables) that will allow reliable discrimination between patients with alternative forms (yes and no) of each phenotype in the population with high specificity, sensitivity and accuracy.

The SNP and clinical variables which were selected for inclusion in models 1 to 7 are listed in Table 11A (FIG. 11A). The Table also shows which SNP alleles are associated with a poor prognosis for each phenotype. The SNP variables included in the models are listed in more detail in FIG. 11B (Table 11B).

Model 1 allows discrimination between patients having a health assessment questionnaire of greater than 2 and less than 2. Model 2 allows discrimination between patients having or not having multiple erosions in hands and feet. Model 3 allows discrimination between patients receiving three or more different treatments and patients receiving less than three treatments. Model 4 allows discrimination between patients whose disease obligates them to leave their job and patients for whom this is not the case. Model 5 allows discrimination between patients needing and not needing surgical intervention (articular prosthesis). Model 6 allows discrimination patients between patients having and not having methotrexate intolerance. Model 7 allows discrimination patients between patients achieving and not achieving remission.

Figure 5B:
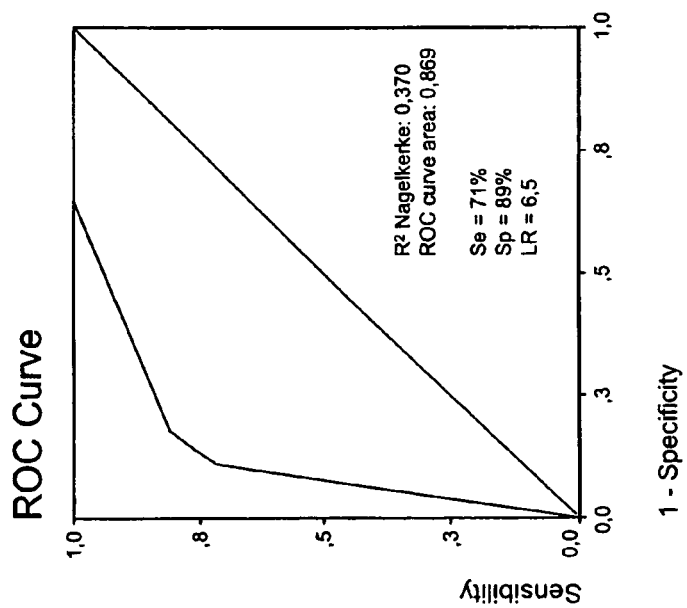
Figure 6B:
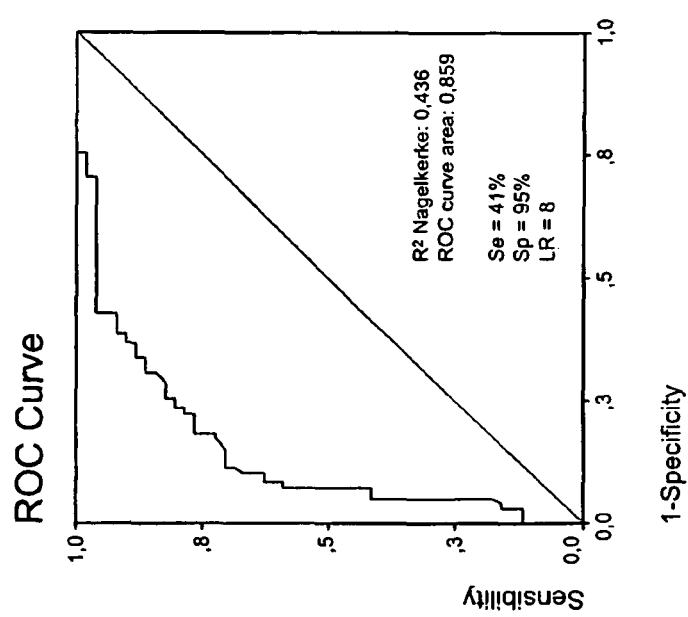
Figure 7B:
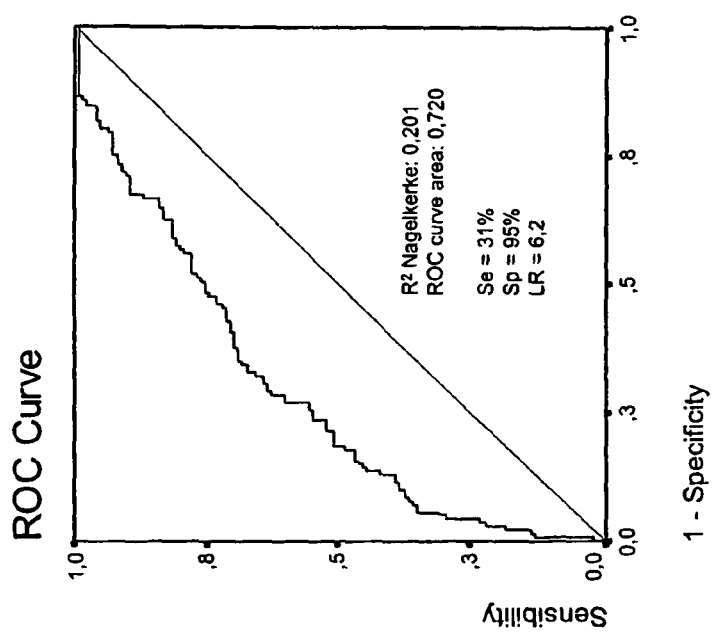
Figure 8B:
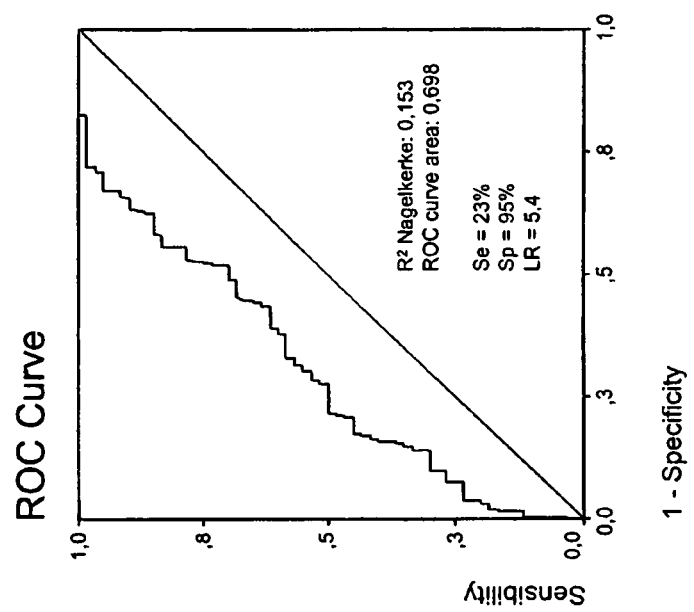
Figure 9B:
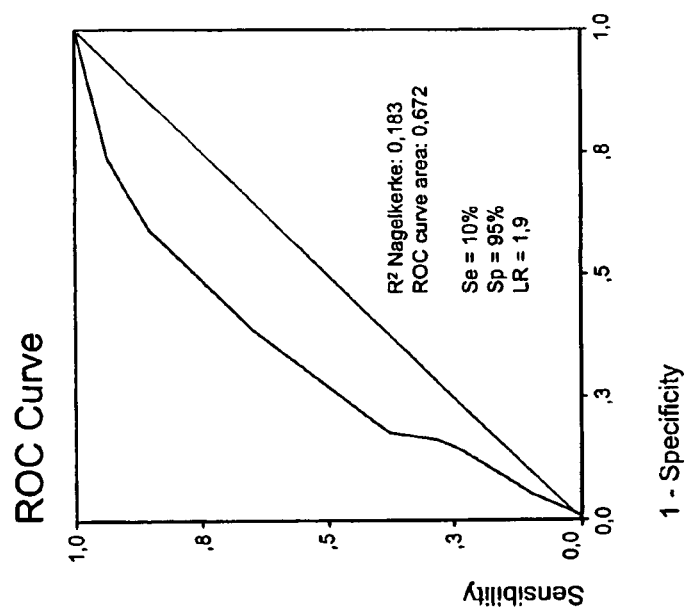
Figure 10B:
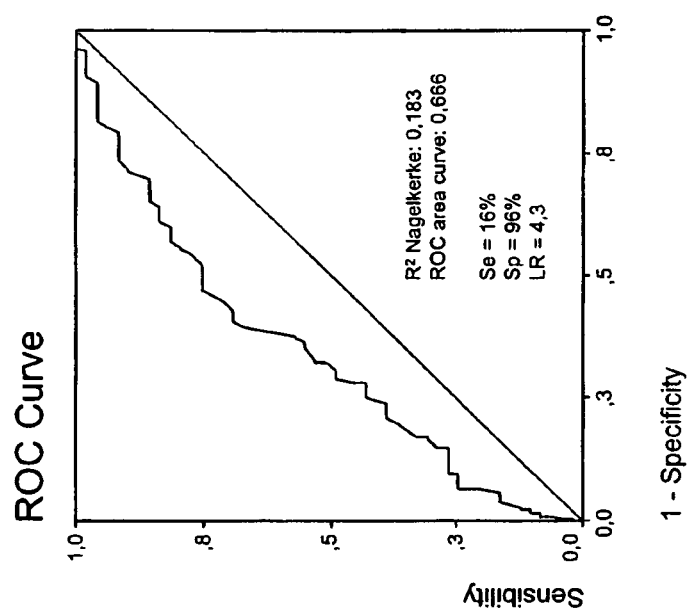

FIGS. 4 to 10 show the ROC curves, sensitivity, specificity and positive likelihood ratios (LR+) of all of the models developed by the inventors.

Tables 4 to 10 show the calculation of probability functions using the discriminating SNPs and clinical variables for each of the models. Regression probability functions are built using the statistical package for the social sciences (SPSS Inc. Headquarters, Chicago, Ill., USA) Version 14.0, SPSS Version 14. B is the coefficient associated to each genotype in the probability function. ET is the error in the calculation of B. Wald is the statistical test. GL are the degrees of freedoms. Sig. P is the value of B for the Wald test. EXP (B) is the relative risk.

The clinical and SNP variables identified, and the models constructed using them, provide new means for predicting the development of each of the corresponding phenotypes in a subject. Thus the invention provides methods for the prognosis of RA and in particular for predicting the risk of developing aggressive of RA phenotype, methotrexate intolerance phenotype, and remission phenotype, as described herein Aggressive RA may be represented clinically by one of a number of presenting phenotypes and reference to predicting aggressive RA may refer to predicting the likelihood of developing one or more of these phenotypes.

The presenting phenotypes for aggressive RA are listed below.

HAQ>2

The health assessment questionnaire (HAQ) (published in Sokka T, Krishnan E, Häkkinen A, Hannonen P, Arthritis Rheum. 2003 January;48(1):59-63) measures the ability of RA patients to carry on normal duties in daily life. A HAQ score of greater than 2 (HAQ>2) indicates that the RA disease is progressing relatively rapidly and that the RA is causing important functional incapacity. Methods for carrying out a HAQ and calculating HAQ score are known in the art Multiple Erosions in Hands and Feet (RX2)

The presence of multiple of erosions in the hands and feet may be measured through visual inspection of x-rays from patients. The greater the number of erosions, the more aggressive the disease is considered to be (Rossi F, Di Dia F, Galipò O, Pistorio A, Valle M, Magni-Manzoni S, Ruperto N, Tomà P, Martini A, Ravelli A., Arthritis Rheum. 2006 October 15;55 (5):717-23). A patient is typically considered to display the multiple erosions phenotype if the erosions are affecting multiple joints and are considered severe.

Receiving ≥3 Different Treatments (TT0 30M)

A patient is generally considered to display the receiving 3 or more different treatments phenotype if the patient doesn't improve after two different treatments and another has to be prescribed.

Obligation to Leave Job (Leaving Job)

Clinicians in general consider that a person suffering from aggressive RA is more likely to need to leave its job. A patient is considered to display the leaving job phenotype if he or she is forced to leave their employment because of RA.

Receiving an Articular Prosthesis (Surgical Intervention)

Aggressive RA normally requires surgical intervention at the joints to insert articular prosthesis (Verstappen S M, Hoes J N, Ter Borg E J, Bijlsma J W, Blaauw A A, van Albada-Kuipers G A, van Booma-Frankfort C, Jacobs J W., Ann Rheum Dis. 2006 November;65(11):1506-11). A patient is considered to display this phenotype if they receive an articular prosthesis.

Any one or more of the models for predicting these presenting phenotypes may be considered as a model for predicting aggressive RA.

Another phenotype which may be predicted according to the invention is the likely response to therapy. In particular, prediction of likely methotrexate intolerance. Intolerance to methotrexate is generally tested for clinically by testing for dose response related toxic effects, such as gastrointestinal intolerance, haematological normalities, alopecia, hepatoxicity and pulmonary toxicity. Approximately 30 to 90% of patients given methotrexate will show intolerance (McKendry R J, Dale P., J Rheumatol. 1993 November;20(11):1850-6) A patient is generally considered to display the methotrexate phenotype if he shows a secondary effect related to the administration of the drug.

The invention also provides means for predicting likelihood of remission in RA patients. A subject is generally considered to have the remission phenotype of there is complete absence of pain in the joints, in the absence of therapy for at least five years.

In general, the subject in the present methods is a human. The subject may be, for example, Chinese, Japanese or Caucasian. Preferably the subject is a Caucasian such as a Spanish individual. The subject may be male or female even if for rheumatoid arthritis the female to male ratio is 3:1.

Preferably, the subject meets the clinical criteria for the diagnosis of rheumatoid arthritis, as decided by the American College of Rheumatology in 1987 (ACR 1987 criteria). These criteria have been published by Arnette et al (Arthritis and Rheumatism, 1988). The subject has already been diagnosed with RA.

Typically the present method may be used to prognose the likelihood of development of one or more of the phenotypes described herein, e.g. at any time during the 5 years after diagnosis.

The present prognostic methods involve determining an outcome for one or more single nucleotide polymorphism (SNP) variables or predictors. The SNP variables are listed in Tables 11A and 11B. The SNPs included in models 1 to 7 are listed in Table 11 . RefSNP codes (rs#) for each SNP are taken from the Single Nucleotide Polymorphism Database (dbSNP) curated by the National Center for Biotechnology Information (NCBI) available on the World Wide Web at ncbi.nlm.nih.gov/entrez/Querv.Fcqi?CMD=search&DB=snp, as at 22 Jun. 2007). Note that rs numbers are not assigned to NULL Alleles.

An outcome for a given SNP variable is the identity of the nucleotide at that position in the genomic DNA sequence of a subject, or the genotype of the subject at that SNP. Thus an outcome for a given SNP may be A, T, C or G.

Table 11B lists the polymorphisms which exist at each of the SNPs included in the present models and Table 11A lists, for each SNP, the polymorphism or allele which is associated with a poor prognosis for each of the phenotypes.

The inventors found that by determining outcomes for these informative SNPs (i.e. nucleotide identities at the SNPs), or particular combinations thereof, it is possible to assess the likelihood of a particular phenotype, e.g. aggressive RA, methotrexate intolerance or remission, in a subject.

The present prognostic methods may also comprise determining an outcome for one or more clinical variables for a subject. These clinical variables are also listed in Table 11A, together with the clinical outcome for each variable which is associated with poor prognosis ANTI PCC is a clinical variable which refers to the level of anti-cyclic citrullinated peptide antibody in the serum of the patient. This is measure in U/ml and is in the range 0-1700U/ml. In the models this measure is a continuous variable which is included in the logistic regression function. Thus an outcome for this variable is the units per milliliter measured in the patient's serum.

ANTI PCC BI is a binary representation of the continuous ANTI PCC clinical variable. Typically, serum levels of antibody are measured, and it is determined whether the level of antibody if above or below a given threshold value. If the level is above the threshold, this is classified as high (1). If the level is below the threshold, this is classified as low or absent (0). Thus an outcome for this variable is 0 or 1.

Erythrocyte sedimentation (VSG) is a continuous variable and refers to the time take by the solid part of the blood to sediment from the liquid part. This may be measured (typically in mm/h) using standard techniques (Vives-Corrons J L, Jou J M. Sangre (Barc). 1982;27(4A):573-8). In the models this measure is a continuous variable which is included in the logistic regression function. Thus an outcome for this variable is a value in mm/h.

Number of involved joints (NoARTDOL) is a continuous variable which refers to the number of joints that are causing pain to the patient. It is typically assessed by interview. In the models this measure is a continuous variable which is included in the logistic regression function. Thus an outcome for this variable is the number of painful joints referred by the patients.

The Rheumatoid Factor test (RF) is primarily used to help diagnose RA and to distinguish it from other forms of arthritis and other conditions that cause similar symptoms of joint pain, inflammation, and stiffness. The test comprises determining the level of RF antibody (typically in units/ml (U/ml)) in a patient's serum. For the purposes of the present models, this is a continuous variable (Greiner A, Plischke H, Kellner H, Gruber R. Ann N Y Acad Sci. June 2005; 1050:295-303). In the models this measure is a continuous variable which is included in the logistic regression function. Thus an outcome for this variable is U/ml of antibodies measured in the serum of the patient.

PCR is a measure of the amount of C-reactive protein in the blood. C-reactive protein concentration in the blood is related to infections and inflammations. The laboratory PCR test measures the concentration of the protein in the serum in milligrams per liter (mg/L) (Miller V M, Redfield M M, McConnell J P. Curr Vasc Pharmacol. January 2007; 5(1):15-25). In the present models this measure has been treated as a continuous variable, which is included in the logistic regression function. Thus an outcome for this variable is quantity of protein measured in the blood of the patient.

Onset age refers to the age in years at which the patient was diagnosed with RA according to the ACR 1987. In the present models this measure has been treated as a continuous variable. which is included in the logistic regression function of the models. Thus an outcome for this variable is age of patient when diagnosed for RA.

Table 11A shows which SNP variables and clinical variables are included in each of the seven models for prognosing phenotypes. As used herein, the "(phenotype name)" variables for a particular phenotype are the SNP variables and clinical variables, selected from those in the first column of Table 11A, which are included in the model for prognosing that phenotype, and which are informative for prognosing the likelihood of the phenotype developing. For example, the "HAQ>2 variables" are the SNP variables and clinical variables, selected from those in the first column of Table 11A, which are included in the HAQ>2 model and which are informative for prognosing the likelihood of the HAQ>2 phenotype (i.e. FGB rs1800790, IL4 rs2070874, ANTI-PCC and VSG).

For each of the variables included in each phenotype model, Table 11A indicates which outcome (SNP allele or clinical outcome) is associated with or suggestive of a poor prognosis for that phenotype.

Accordingly the invention in one aspect provides a method for predicting the likely course of RA in a subject, comprising the step of determining or obtaining, for that subject, outcomes for one or more SNP variables and one or more clinical variables listed in Tables 11A & B. Predicting RA course may refer in particular to predicting one or more of the phenotypes described herein.

The methods include a method for predicting aggressive RA in a subject. This may be done by determining the likelihood of the subject developing one of more of the aggressive RA phenotypes described herein.

For example, a method may comprise determining the likelihood of a subject developing the HAQ>2 phenotype described herein. Typically the method comprises determining or obtaining for the subject, an outcome for each of the HAQ>2 variables listed in Table 11A (model 1 variables). Use of these variables allows prognosis of the HAQ>2 phenotype in a Spanish population with an LR+ of 8 (see Example 2 and FIG. 4). Details for the calculation of a probability function using these variables are given in Table 4.

For example, a method may comprise determining the likelihood of a subject developing the multiple erosions phenotype described herein. Typically the method comprises determining or obtaining for the subject, an outcome for each of the multiple erosions variables listed in Table 11A (model 2 variables). Use of these variables allows prognosis of multiple erosions phenotype in a Spanish population with an LR+ of 6.5 (see Example 2 and FIG. 6). Details for the calculation of a probability function using these variables are given in Table 6.

For example, a method may comprise determining the likelihood of a subject developing the >3 different treatments phenotype described herein. Typically the method comprises determining or obtaining for the subject, an outcome for each of the >3 different treatments variables listed in Table 11A (model 3 variables). Use of these variables allows prognosis of >3 different treatments phenotype in a Spanish population with an LR+ of 6.2 (see Example 2 and FIG. 7). Details for the calculation of a probability function using these variables are given in Table 7.

For example, a method may comprise determining the likelihood of a subject developing the leaving the job phenotype described herein. Typically the method comprises determining or obtaining for the subject, an outcome for each of the leaving the job variables listed in Table 11A (model 4 variables). Use of these variables allows prognosis of the leaving the job phenotype in a Spanish population with an LR+ of 1.9 (see Example 2 and FIG. 9). Details for the calculation of a probability function using these variables are given in Table 9.

For example, a method may comprise determining the likelihood of a subject developing the surgical intervention phenotype described herein. Typically the method comprises determining or obtaining for the subject, an outcome for each of the surgical intervention variables listed in Table 11A. (model 5 variables). Use of these variables allows prognosis of the surgical intervention phenotype in a Spanish population with an LR+ of 5.4 (see Example 2 and FIG. 8). Details for the calculation of a probability function using these variables are given in Table 8.

A method may comprise carrying out one or more of the above tests for development of aggressive phenotypes. For example, a method may comprise carrying out at least 2, 3, 4 or all 5 of the above test methods, using the corresponding model variables. For example, a method may comprise at least assessing the likelihood of the HAQ>2, multiple erosions, >3 different treatments, and surgical intervention phenotypes, or the HAQ>2, multiple erosions and >3 different treatments phenotypes, or the HAQ>2 and multiple erosions phenotypes. In one example the method comprises at least predicting the likelihood of the HAQ>2 phenotype. The variables tested will be selected accordingly in line with the models above and the information in Table 11A.

The present methods also include a method for predicting the likelihood of methotrexate intolerance in a patient. Typically the method comprises determining or obtaining for the subject, an outcome for each of the therapy response variables listed in Table 11A. (model 6 variables). Use of these variables allows prognosis of methotrexate intolerance phenotype in a Spanish population with an LR+ of 4.3 (see Example 2 and FIG. 10). Details for the calculation of a probability function using these variables are given in Table 10.

The present methods also include a method for predicting the likelihood of remission in a patient. Typically the method comprises determining or obtaining for the subject, an outcome for each of the remission variables listed in Table 11A. (model 7 variables). Use of these variables allows prognosis of remission phenotype in a Spanish population with an LR+ of 6.5 (see Example 2 and FIG. 5). Details for the calculation of a probability function using these variables are given in Table 5.

A subject may be tested for likely development of one or more of the above phenotypes. For example, a subject may be tested for likelihood of developing aggressive RA (by any one or more of the methods described above) in combination with a test for likelihood of developing methotrexate intolerance and/or remission. Similarly, a subject may be tested for likely remission as well as methotrexate intolerance. Any combination of the above methods may be used, so that a subject may be simultaneously assessed for likely development of more than one phenotype. The variables tested will be selected accordingly in line with the models above and the information in Table 11A.

In one example, a method may comprise at least assessing the likelihood of the HAQ>2, multiple erosions, remission, >3 different treatments, surgical intervention and therapy response phenotypes, or the HAQ>2, multiple erosions, remission, >3 different treatments and surgical intervention phenotypes, or the HAQ>2, multiple erosions, remission and >3 different treatments phenotypes, or the HAQ>2, multiple erosions and remission phenotypes. In one example, the method comprises at least predicting the likelihood of the HAQ>2 and remission phenotypes.

In one example, a method of the invention comprises determining the likelihood of developing the HAQ>2 phenotype and determining the likelihood of developing the multiple erosions phenotype and determining the likelihood of developing the >3 different treatments phenotype and determining the likelihood of developing the leaving the job phenotype and determining the likelihood of developing the surgical intervention phenotype and determining the likelihood of developing methotrexate intolerance and determining the likelihood of remission in a subject. In that case typically, outcomes are determined for all of the variables in Table 11A.

In some aspects the present methods may include determining other factors for a subject. For example, the subject may be genotyped for one or more other genetic variations (such as other SNPs not listed in Table 11A or 11B). These may be mutations associated with RA or another condition. For example, a subject may be genotyped at one or more of the remaining SNPs listed in Table 1A or 1B, e.g. using the Artchip microarray described herein. Other markers (e.g. SNPs) associated with other diseases may also be determined.

The present methods may be used in conjunction with or in addition to standard clinical tests.

The present methods allow accurate prediction of RA phenotypes based on a relatively small number of informative SNPs and clinical variables. This can be advantageous in that it allows use of genotyping techniques that would not necessarily be suitable for large scale SNP screening, as well as larger scale genotyping methods.

In general, even if a larger number of SNPs or genetic variations or factors are tested in the present methods, prediction of an RA phenotype can be made based only on outcomes for the variables of the corresponding phenotype model in Table 11A. These variables are sufficient for the prediction. Therefore in one example, the present methods allow differential prognosis of the RA phenotypes described herein, based on (at a maximum) the outcomes for the variables of the corresponding models in Table 11A.

In some instances though, it may be that some additional variables such as SNPs or other factors are used in the prediction. For example, in the present methods, prognosis may be made based on the outcomes of a maximum of 100, 90, 80, 70, 60, 50, 45, 40, 35, 30, 29, 25, 20, 19, 18, 17, 16, 15, 14, 13, 12, 11, 10, 9, 8, 7, 6, 5, 4, 3, or 2 variables, such as SNPs or RA associated SNPs. The SNPs may comprise (or consist of), or be selected from the Table 11A variables or SNP variables.

In one aspect the method may involve genotyping a maximum of 100, 90, 80, 70, 60, 50, 40, 30, 25, 20, 19, 18, 17, 16, 15, 14, 13, 12, 11, 10, 9, 8, 7, 6, 5, 4, 3, or 2 SNPs or RA-associated SNPs. The method may involve genotyping a maximum of (no more than) all the SNPs in Table 11A, Table 1A or Table 1B. In some instances, the method comprises genotyping at a maximum, SNP variables for one or more of models 1 to 7, selected as described above.

Preferably the number and combination of variables such as SNPs used to construct a model for predicting a phenotype according to the invention, is such that the model allows prediction to be made with an LR+ value of at least 1.5, such as at least 2, 3, 4, 5, 6, 7, 8, 9, or 10. Calculation of LR+ values is described herein.

Once an outcome is determined for each of the variables for prediction of a given phenotype, these outcomes are used in or inserted in a suitable probability function (for prediction of that phenotype), as described herein and a probability function value is calculated. Outcomes may be codified for use in the probability function and calculation of the probability function value. The probability function value is then compared with probability function values obtained for a population of individuals of known (clinically determined) phenotype. The risk of the subject having or developing the particular phenotype is thereby determined.

A suitable probability function for determining a given phenotype may be derived by methods as set out in Example 2 and described herein. Typically a study population of individuals is provided. These individuals are of known (clinically determined) phenotype with respect to the phenotype that the probability function will be used to determine. Clinical diagnosis and of RA can be made following the criteria of the American College of Rheumatology (1987) (ACR 1987) as described herein. Preferably the individuals in the study population meet the ACR 1987 definition. Each of the RA phenotypes which may be assessed according to the invention may be clinically diagnosed as described herein.

In one example, the individuals in the study population may meet one or more, for example, 2, 3, 4, 5 or all 6 of the complete inclusion criteria for the study population in Example 2: meeting the ACR 1987 criteria for RA diagnosis; having RA onset after the age of 18; having radiological erosions (damage at the level of the joints affected by RA); Caucasian; having more than 5 years of evolution; diagnosed after 1 Jan. 1990.

The population may be for example, a Chinese, Japanese or a Caucasian population, such as Spanish population. The population may comprise females and males. In one example, the female to male ratio may be about 3:1. Preferably the population used for deriving a probability function comprises a representative sample of the population in which the probability function will be applied.

In general at least n individuals are included in the study population. Typically n is 200-1000, for example 300, 400, 500 or 600. Where a probability function is for determining between alternative phenotypes, preferably there are approximately equal numbers of individuals with each of the alternative phenotypes in the population. Thus where there are two alternative phenotypes, A and B, the population is preferably approximately 50% phenotype A and 50% phenotype B. However, the ratios may be for example, 60%/40%, 70%/30%, 80%/20%, 90%/10% or any statistically acceptable distribution. For example, where the probability function is for prognosis of HAQ>2 vs HAQ≤2, preferably about 50% of the population are of clinically determined HAQ>2 phenotype and about 50% of the population are of clinically determined HAQ≤2 phenotype. Where the probability function is for prognosis of multiple erosions, preferably about 50% of the population meet the clinical criteria for multiple erosions and about 50% of the population do not.

Each individual in the study population is then tested to determine an outcome for each of the discriminating variables for the particular phenotype (see Table 11A). This provides a number of outcomes for each individual. Testing, e.g. genotyping, may be carried out by any of the methods described herein, e.g. by microarray analysis as described herein. Testing is typically ex vivo, carried out on a suitable sample obtained from an individual.

Multiple genotype-phenotype associations may then be analysed using stepwise multivariate logistic regression analysis, using as the dependent variable the clinically determined RA phenotype and as independent variables the outcomes of the informative variables, e.g. as recommended by Balding D J. (2006[35]). The goodness of fit of the models obtained may be evaluated using Hosmer-Lemeshow statistics and their accuracy assessed by calculating the area under the curve (AUC) of the Receiver Operating Characteristic curve (ROC) with 95% confidence intervals (see, e.g. (Janssens A C J W et al., 2006[36]. Suitable methods are described in Example 2.

The sensitivity, specificity, and positive likelihood ratio (LR+=sensitivity/(1-specificity)) may be computed by means of ROC curves. Preferably the model has an LR+ value of at least 1.5, for example, at least 2, 3, 4, 5, 6, 7, 8, 9 or 10.

Mean probability function values for each of the alternative phenotypes in the population can be compared using a t test. In general the probability functions are able to distinguish between the different phenotypes in the study population in a statistically significant way, for example, at p≤0.05 in a t-test. Thus the probability functions produce a statistically significant separation between individuals of different phenotype in the population.

Statistical analyses may be performed, for example, using the Statistical Package for the Social Sciences (SPSS Inc. Headquarters, Chicago, Ill., USA) version 14.0.

Probability function values can be calculated for each individual of known phenotype in the study population and plotted in a suitable graph.

In order to carry out the present methods of prognosis, a probability function value is calculated for the test individual, and this is compared with the probability function values for the individuals of known phenotype in the study population in order to determine the risk of a given phenotype in that individual. The comparison may be done by comparison with a graph or by any other suitable means known to those skilled in the art.

Thus for example, in deriving a probability function for use in differentially prognosing HAQ>2 vs HAQ≤2, a study population of individuals clinically diagnosed as HAQ>2 and individuals clinically diagnosed as HAQ≤2 is provided. Each individual may then be tested to determine an outcome for each of the HAQ>2 (model 1) discriminating variables in Table 11A. Stepwise multiple logistic regression is performed on the "outcomes" and "phenotype" data and a probability function is derived which is able to distinguish between the two phenotypic groups in the study population in a statistically significant way.

Thus in one aspect the invention further provides a method of deriving a probability function for use in determining an RA phenotype as described herein, comprising:
(i) providing a study population of individuals, wherein each individual is of known clinically determined phenotype with respect to the RA phenotype;
(ii) determining or obtaining for each individual an outcome for each of a set of variables, thereby obtaining a set of outcomes for each individual;
(iii) applying stepwise multiple logistic regression analysis to the outcomes obtained in (ii) and the known phenotypes referred to in (i); and
(iv) thereby deriving a probability function which produces a statistically significant separation between individuals of different phenotype in the population;
wherein:
(a) the probability function is for prognosing the likelihood of developing the HAQ>2 phenotype according to the invention, and the set of variables for which outcomes are determined or obtained in step (ii) is selected from or consists of the HAQ>2 variables in Table 11A;
(b) the probability function is for prognosing the likelihood of developing the multiple erosions phenotype according to the invention, and the set of variables for which outcomes are determined or obtained in step (ii) is selected from or consists of the multiple erosions variables in Table 11A;

(c) the probability function is for prognosing the likelihood of developing the >3 different treatments phenotype according to the invention, and the set of variables for which outcomes are determined or obtained in step (ii) is selected from or consists of the >3 different treatments variables in Table 11A;

(d) the probability function is for prognosing the likelihood of developing the leaving the job phenotype according to the invention, and the set of variables for which outcomes are determined or obtained in step (ii) is selected from or consists of the leaving the job variables in Table 11A;

(e) the probability function is for prognosing the likelihood of developing the surgical intervention phenotype according to the invention, and the set of variables for which outcomes are determined or obtained in step (ii) is selected from or consists of the surgical intervention variables in Table 11A;

(f) the probability function is for prognosing the likelihood of developing the methotrexate intolerance phenotype according to the invention, and the set of variables for which outcomes are determined or obtained in step (ii) is selected from or consists of the HAQ>2 variables in Table 11A; and/or (g) the probability function is for prognosing the likelihood of developing the HAQ>2 phenotype according to the invention, and the set of variables for which outcomes are determined or obtained in step (ii) is selected from or consists of the HAQ>2 variables in Table 11A.

Derivation of the probability functions may be carried out by a computer. Therefore in one aspect, the invention also relates to a computational method of deriving a probability function for use in determining an RA phenotype which method comprises applying stepwise multiple logistic regression analysis to outcomes data and phenotype data obtained from a suitable study population of individuals, wherein each individual is of known clinically determined phenotype with respect to the RA phenotype, thereby deriving a probability function which produces a statistically significant separation between individuals of different phenotype in the population; wherein:

(i) the phenotype data comprises the known clinically determined phenotype of each individual;

(ii) the outcomes data for each individual comprises outcomes for one or more single nucleotide polymorphism variables and one or more clinical variables listed in column 1 of Table 11A;

and wherein:

(a) the probability function is for prognosing the likelihood of developing the HAQ>2 phenotype according to the invention, and the variables for which outcomes data is obtained (and referred to in (ii)) comprise or consist of the HAQ>2 variables in Table 11A;

(b) the probability function is for prognosing the likelihood of developing the multiple erosions phenotype according to the invention, and the variables for which outcomes data is obtained (and referred to in (ii)) comprise or consist of the multiple erosions variables in Table 11A;

(c) the probability function is for prognosing the likelihood of developing the >3 different treatments phenotype according to the invention, and the variables for which outcomes data is obtained (and referred to in (ii)) comprise or consist of the >3 different treatments variables in Table 11A;

(d) the probability function is for prognosing the likelihood of developing the leaving the job phenotype according to the invention, and the variables for which outcomes data is obtained (and referred to in (ii)) comprise or consist of the leaving the job variables in Table 11A;

(e) the probability function is for prognosing the likelihood of developing the surgical intervention phenotype according to the invention, and the variables for which outcomes data is obtained (and referred to in (ii)) comprise or consist of the surgical intervention variables in Table 11A;

(f) the probability function is for prognosing the likelihood of developing the methotrexate intolerance phenotype according to the invention, and the variables for which outcomes data is obtained (and referred to in (ii)) comprise or consist of the HAQ>2 variables in Table 11A; and/or (g) the probability function is for prognosing the likelihood of developing the HAQ>2 phenotype according to the invention, and and the variables for which outcomes data is obtained (and referred to in (ii)) comprise or consist of the HAQ>2 variables in Table 11A.

Suitable study populations and statistical analysis methods are described above. Reference may also be made to the present Examples.

Details for calculation of a probability function from the SNP and clinical variables listed for each phenotype are given in Tables 4 to 10. Statistical analyses may be performed, for example, using the Statistical Package for the Social Sciences (SPSS Inc. Headquarters, Chicago, Ill., USA) version 14.0. These may be used for calculation of probability function values for use in the methods herein. The data in the Tables may be used to construct probability functions for use in the invention. The probability functions, together with the information in Tables 11A and 11B may be used to determine a diagnosis or prognosis according to the invention.

In one aspect the invention relates to probability functions constructed or derived using the data in any of Tables 4 to 10, and to their use in a method, e.g. a computational method, for prognosing an RA phenotype. The invention further relates to associated computer programs and computer systems as described herein. The invention also relates to the probability functions derived according to the present methods and to their use in the methods described herein.

The process of calculating a probability function value for a test subject and comparing the value to values obtained from a study population of individuals of known phenotypes in order to evaluate the risk of developing a phenotype in the test subject may also be carried out using appropriate software.

Therefore in one aspect the invention relates to a computational method for determining a RA phenotype using the outcomes of discriminating variables ("outcomes data") for that phenotype obtained according to the methods described herein. In the computational method, outcomes data for the discriminating variables for a particular phenotype obtained from a test subject (test outcomes data) is inputted in a suitable probability function to produce a probability function value for the test subject. The test probability function value is then compared with probability function values for individuals of known phenotype in order to diagnose or prognose the phenotype of the test individual. The comparison may be made using the methods described herein.

The invention further relates to a computer system comprising a processor and means for controlling the processor to carry out a computational method described herein, and to a computer program comprising computer program code which when run on a computer or computer network causes the computer or computer network to carry out the computational method. In one aspect, the computer program is stored on a computer readable medium.

As described above and in the Examples, the present inventors have also identified a number of single nucleotide polymorphisms (SNPs) which show single locus allelic association with the RA phenotypes described herein. The SNPs which show statistically significant association are listed in Table 12 (FIG. 12). P-values were calculated by Chi square test using SPSS and HelixTree softwares.

By identifying the nucleotide in the genomic DNA of a subject at one (or more) of these SNPs, it is possible to assess the risk or susceptibility of that individual to the given phenotype.

In one aspect the invention relates to the use of one or more of the SNPs in Table 12 in a method for prognosing an RA phenotype, in particular for determining the likelihood of development of an RA phenotype with which the SNP(s) is or are statistically significantly associated (Table 12) as described herein.

Thus the invention in one aspect relates to a method for prognosing HAQ>2 phenotype (as described herein) comprising determining the genotype of an individual at one or more of the HAQ>2 SNPs in Table 12.

The invention also relates to a method for prognosing RX2 phenotype (as described herein) comprising determining the genotype of an individual at one or more of the RX2 SNPs in Table 12.

The invention also relates to a method for prognosing TT0_30M phenotype (as described herein) comprising determining the genotype of an individual at one or more of the TT0_3 SNPs in Table 12.

The invention also relates to a method for prognosing surgical intervention phenotype (as described herein) comprising determining the genotype of an individual at the surgical intervention SNP in Table 12.

The invention also relates to a method for prognosing remission phenotype (as described herein) comprising determining the genotype of an individual at one or more of the remission SNPs in Table 12.

The invention also relates to a method for prognosing leaving the job phenotype (as described herein) comprising determining the genotype of an individual at one or more of the leaving the job SNPs in Table 12.

The invention also relates to a method for prognosing methotrexate intolerance phenotype (as described herein) comprising determining the genotype of an individual at one or more of the methotrexate intolerance SNPs in Table 12.

In general the present methods are carried out ex vivo or in vitro, e.g. using a sample obtained from the individual. A method may comprise use of the outcomes of clinical variables which have been obtained by the methods described herein.

Various methods are known in the art for determining the presence or absence in a test sample of a particular nucleic acid sequence, for example a nucleic acid sequence which has a particular nucleotide at a position of single nucleotide polymorphism. For example, genotype may be determined by microarray analysis, sequencing, primer extension, ligation of allele specific oligonucleotides, mass determination of primer extension products, restriction length polymorphism analysis, single strand conformational polymorphism analysis, pyrosequencing, dHPLC or denaturing gradient gel electrophoresis (DGGE). Furthermore, having sequenced nucleic acid of an individual or sample, the sequence information can be retained and subsequently searched without recourse to the original nucleic acid itself. Thus, for example, a sequence alteration or mutation may be identified by scanning a database of sequence information using a computer or other electronic means.

In general, a sample is provided, containing nucleic acid which comprises at least one of the genetic variations to be tested. The nucleic acid comprises one or more target regions comprising the genetic variation(s) (SNPs) which are to be characterised.

The nucleic acid may be obtained from any appropriate biological sample which contains nucleic acid. The sample may be taken from a fluid or tissue, secretion, cell or cell line derived from the human body.

For example, samples may be taken from blood, including serum, lymphocytes, lymphoblastoid cells, fibroblasts, platelets, mononuclear cells or other blood cells, from saliva, liver, kidney, pancreas or heart, urine or from any other tissue, fluid, cell or cell line derived from the human body. For example, a suitable sample may be a sample of cells from the buccal cavity.

Preferably nucleic acid is obtained from a blood sample.

In general, nucleic acid is extracted from the biological sample using conventional techniques. The nucleic acid to be extracted from the biological sample may be DNA, or RNA, typically total RNA. Typically RNA is extracted if the genetic variation to be studied is situated in the coding sequence of a gene. Where RNA is extracted from the biological sample, the methods may further comprise a step of obtaining cDNA from the RNA. This may be carried out using conventional methods, such as reverse transcription using suitable primers. Subsequent procedures are then typically carried out on the extracted DNA or the cDNA obtained from extracted RNA. The term DNA, as used herein, may include both DNA and cDNA.

In general the genetic variations to be tested are known and characterised, e.g. in terms of sequence. Therefore nucleic acid regions comprising the genetic variations may be obtained using methods known in the art.

In one aspect, DNA regions which contain the genetic variations (SNPS) to be identified (target regions) are subjected to an amplification reaction in order to obtain amplification products which contain the genetic variations to be identified. Any suitable technique or method may be used for amplification.

For example, the polymerase chain reaction (PCR) (reviewed for instance in "PCR protocols; A Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, NY, 1989, and Ehrlich et al, Science, 252:1643-1650, (1991)) may be used. The nucleic acid used as template in the amplification reaction may be genomic DNA, cDNA or RNA.

Other specific nucleic acid amplification techniques include strand displacement activation, the QB replicase system, the repair chain reaction, the ligase chain reaction, rolling circle amplification and ligation activated transcription.

Allele-specific oligonucleotides may be used in PCR to specifically amplify particular sequences if present in a test sample. Assessment of whether a PCR band contains a gene variant may be carried out in a number of ways familiar to those skilled in the art. The PCR product may for instance be treated in a way that enables one to display the polymorphism on a denaturing polyacrylamide DNA sequencing gel, with specific bands that are linked to the gene variants being selected.

Those skilled in the art are well versed in the design of primers for use in processes such as PCR. Various techniques for synthesizing oligonucleotide primers are well known in the art, including phosphotriester and phosphodiester synthesis methods.

A further aspect of the present invention provides a pair of oligonucleotide amplification primers suitable for use in the methods described herein.

PCR primers suitable for amplification of target DNA regions comprising the SNPs in Table 1A are listed in Table 3A and Table 3B. The present methods may comprise the use of one or more of these primers or one or more of the listed primer pairs, according to the SNPs to be genotyped, wherein these SNPs are selected as described herein. In one aspect the method comprises use of all of the primers listed in Tables 3A and 3B. Suitable reaction conditions may be determined using the knowledge in the art.

The amplified nucleic acid may then be sequenced and/or tested in any other way to determine the presence or absence of a particular feature. Nucleic acid for testing may be prepared from nucleic acid removed from cells or in a library using a variety of other techniques such as restriction enzyme digest and electrophoresis.

For example, the allele of the at least one polymorphism (i.e. the identity of the nucleotide at the position of single nucleotide polymorphism) may be determined by determining the binding of an oligonucleotide probe to the amplified region of the genomic sample. A suitable oligonucleotide probe comprises a nucleotide sequence which binds specifically to a particular allele of the at least one polymorphism and does not bind specifically to other alleles of the at least one polymorphism. Such a probe may correspond in sequence to a region of genomic nucleic acid, or its complement, which contains one or more of the SNPs described herein. Under suitably stringent conditions, specific hybridisation of such a probe to test nucleic acid is indicative of the presence of the sequence alteration in the test nucleic acid. For efficient screening purposes, more than one probe may be used on the same test sample.

Those skilled in the art are well able to employ suitable conditions of the desired stringency for selective hybridisation, taking into account factors such as oligonucleotide length and base composition, temperature and so on.

Suitable selective hybridisation conditions for oligonucleotides of 17 to 30 bases include hybridization overnight at 42° C. in 6× SSC and washing in 6× SSC at a series of increasing temperatures from 42° C. to 65° C.

Other suitable conditions and protocols are described in Molecular Cloning: a Laboratory Manual: 2nd edition, Sambrook et al., 1989, Cold Spring Harbor Laboratory Press and Current Protocols in Molecular Biology, Ausubel et al. eds., John Wiley & Sons, 1992.

A further aspect of the present invention provides an oligonucleotide which hybridises specifically to a nucleic acid sequence which comprises a particular allele of a polymorphism selected from the group consisting of the single nucleotide polymorphisms shown in Table 1A. 1B or Table 18, and does not bind specifically to other alleles of the SNP. Hybridisation may be determined under suitable selective hybridisation conditions as described herein.

Such oligonucleotides may be used in a method of screening nucleic acid.

In some preferred embodiments, oligonucleotides according to the present invention are at least about 10 nucleotides in length, more preferably at least about 15 nucleotides in length, more preferably at least about 20 nucleotides in length. Oligonucleotides may be up to about 100 nucleotides in length, more preferably up to about 50 nucleotides in length, more preferably up to about 30 nucleotides in length. The boundary value 'about X nucleotides' as used above includes the boundary value 'X nucleotides'. Oligonucleotides which specifically hybridise to particular alleles of the SNPs listed in Table 1A are listed in Table 2 and are described herein.

Where the nucleic acid is double-stranded DNA, hybridisation will generally be preceded by denaturation to produce single-stranded DNA. The hybridisation may be as part of an amplification, e.g. PCR procedure, or as part of a probing procedure not involving amplification. An example procedure would be a combination of PCR and low stringency hybridisation. A screening procedure, chosen from the many available to those skilled in the art, is used to identify successful hybridisation events and isolated hybridised nucleic acid.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RN'ase cleavage and allele specific oligonucleotide probing. Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Approaches which rely on hybridisation between a probe and test nucleic acid and subsequent detection of a mismatch may be employed. Under appropriate conditions (temperature, pH etc.), an oligonucleotide probe will hybridise with a sequence which is not entirely complementary. The degree of base-pairing between the two molecules will be sufficient for them to anneal despite a mis-match. Various approaches are well known in the art for detecting the presence of a mismatch between two annealing nucleic acid molecules.

For instance, RN'ase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid.

Nucleic acid in a test sample, which may be a genomic sample or an amplified region thereof, may be sequenced to identify or determine the identity of a polymorphic allele. The allele of the SNP in the test nucleic acid can therefore be compared with the susceptibility alleles of the SNP as described herein to determine whether the test nucleic acid contains one or more alleles which are associated with disease.

Typically in sequencing, primers complementary to the target sequence are designed so that they are a suitable distance (e.g. 50-400 nucleotides) from the polymorphism. Sequencing is then carried out using conventional techniques. For example, primers may be designed using software that aims to select sequence(s) within an appropriate window which have suitable Tm values and do not possess secondary structure or that will hybridise to non-target sequence.

Sequencing of an amplified product may involve precipitation with isopropanol, resuspension and sequencing using a TaqFS+ Dye terminator sequencing kit. Extension products may be electrophoresed on an ABI 377 DNA sequencer and data analysed using Sequence Navigator software.

Genotype analysis may be carried out by microarray analysis. Any suitable microarray technology may be used. The methodology reported in Tejedor et al 2005 (Clinical Chemistry 51: 1137-1144), including the MG 1.0 software and in International Patent Application No. PCT/IB2006/00796 filed 12 Jan. 2006 (the contents of which are hereby incorporated by reference) may be used. This technology uses a low-density DNA array and hybridisation to allele-specific oligonucleotide probes to screen for SNPs. Thus in one aspect the Artchip microarray and technology of the present invention may be used to determine the genotype of the informative SNPs as described herein.

Once a subject has received a prognosis of a particular RA phenotype (a significant risk of that phenotype developing according to the invention), the most appropriate treatment for that subject can be selected. In this way, the invention allows better targeting of therapies to patients.

Thus in a further aspect, the invention provides a method of selecting a suitable treatment for a subject diagnosed as having RA, the method comprising:
(a) determining the likelihood of a particular RA phenotype developing in the subject by a method described herein; and
(b) selecting a suitable treatment.

The selected treatment may then be administered to the subject. Thus the invention also relates to a method of treating RA in a subject comprising:
(a) determining the likelihood of particular RA phenotype developing in the subject by a method described herein; and
(b) treating the subject with a suitable treatment.

For example, if a subject is determined to be at higher risk of developing an aggressive RA phenotype (by one or more of the methods described herein), an appropriate treatment, e,g, more intensive treatment, may be selected. If a subject is assessed as likely to be intolerant to methotrexate, an alternative therapy can be provided.

Means for carrying out the present prognostic methods may be provided in kit form e.g. in a suitable container such as a vial in which the contents are protected from the external environment. Therefore in one aspect the invention further relates to prognostic kits suitable for use in the methods described herein. Typically a kit comprises:
(i) means for determining outcomes for the selected variable(s) or SNP variables; and
(ii) instructions for determining prognosis based on the outcomes of the variables.

The means (i) may comprise one or more oligonucleotide probes suitable for detection of one or more SNP variables to be determined. For example, the means (i) may comprise one or more probe pairs or probe sets listed in Table 2. In one instance the kit may comprise all of the probe sets in Table 2.

The means (i) may comprise a suitable microarray, as described herein. The means (i) may comprise one or more pairs of sequencing primers suitable for sequencing one or more of the SNP variables to be determined.

The instructions (ii) typically comprise instructions to use the outcomes determined using the means (i) for the prognosis. The instructions may comprise a chart showing risks of RA recurrence. The kit may include details of probability functions which may be used in prognosis, such as those described herein.

A kit may in some cases include a computer program as described herein.

A kit may include other components suitable for use in the present methods. For example, a kit may include primers suitable for amplification of target DNA regions containing the SNPs to be determined, such as those described herein. For example, a kit may contain one or more primer pairs listed in Tables 3. A kit may also include suitable labelling and detection means, controls and/or other reagents such as buffers, nucleotides or enzymes e.g. polymerase, nuclease, transferase.

Nucleic acid according to the present invention, such as an oligonucleotide probe and/or pair of amplification primers, may be provided as part of a kit. The kit may include instructions for use of the nucleic acid, e.g. in PCR and/or a method for determining the presence of nucleic acid of interest in a test sample. A kit wherein the nucleic acid is intended for use in PCR may include one or more other reagents required for the reaction, such as polymerase, nucleosides, buffer solution etc. The nucleic acid may be labelled.

A kit for use in determining the presence or absence of nucleic acid of interest may include one or more articles and/or reagents for performance of the method, such as means for providing the test sample itself, e.g. a swab for removing cells from the buccal cavity or a syringe for removing a blood sample (such components generally being sterile).

In a further aspect the present invention also relates to DNA chips or microarrays and methods for their use, which allow reliable genotyping of individuals with respect to multiple RA associated genetic variations simultaneously and for clinical purposes.

Thus in one aspect, the invention further provides a method of genotyping RA associated genetic variations in an individual, which is sufficiently sensitive, specific and reproducible for clinical use. The inventors have developed low density DNA-microarrays with specifically designed probes for use in the method, and a computational method or algorithm for interpreting and processing the data generated by the arrays.

In one aspect, the invention relates to an in vitro method for genotyping RA associated genetic variations in an individual. The method allows simultaneous genotyping of multiple human genetic variations present in one or more genes of a subject. The method of the invention allows identification of nucleotide changes, such as, insertions, duplications and deletions and the determination of the genotype of a subject for a given genetic variation.

Genetic variation or genetic variant refers to mutations, polymorphisms or allelic variants. A variation or genetic variant is found amongst individuals within the population and amongst populations within the species.

A RA associated genetic variation may refer to a genetic variation that is associated with RA in a statistically significant way and that can be used as an aid in the diagnosis, prognosis or prediction of response to therapy in an individual.

Polymorphism refers to a variation in the sequence of nucleotides of nucleic acid where every possible sequence is present in a proportion of equal to or greater than 1% of a population; in a particular case, when the said variation occurs in just one nucleotide (A, C, T or G) it is called a single nucleotide polymorphism (SNP).

Genetic mutation refers to a variation in the sequence of nucleotides in a nucleic acid where every possible sequence is present in less than 1% of a population Allelic variant or allele refers to a polymorphism that appears in the same locus in the same population.

Thus a genetic variation may comprise a deletion, substitution or insertion of one or more nucleotides. In one aspect the genetic variations to be genotyped according to the present methods comprise SNPs.

A given gene may comprise one or more genetic variations. Thus the present methods may be used for genotyping of one or more genetic variations in one or more genes.

Typically the individual is a human.

Typically, for a given genetic variation there are three possible genotypes:

AA the individual is homozygous for genetic variation A (e.g. homozygous for a wild type allele)

BB the individual is homozygous for genetic variation B (e.g. homozygous for a mutant allele)

AB the individual is heterozygous for genetic variations A and B (e.g. one wild type and one mutant allele)

The genetic variations, such as SNPs, to be analysed according to the present methods, are associated with RA. Examples of genetic variations associated with RA which may be assessed by the present methods include those in Table 1A and Table 1B (FIG. 1).

The sequences of all the genes mentioned in FIG. 1 are known and recognized on the following websites: GeneBank (NCBI), GeneCard (Weizmann Institute of Sciences) and Snpper.chip.org (Innate Immunity PGA). Table 11 provides refSNP codes (rs#) for a number of SNPs. These are taken from the Single Nucleotide Polymorphism Database (cfb-SNP) curated by the National Center for Biotechnology Information (NCBI) ( available on the World Wide Web at ncbi.nlm.nih.gov/entrez/
Ouerv.fcqi?CMD=search&DB=snp, as at 22 Jun. 2007).

By permitting clinical genotyping of one or more of the above genetic variations, the present method has use in for example, diagnosing susceptibility to or the presence of RA in a subject. The present genotyping methods are also be useful in prognosing RA phenotypes, as described herein.

At least one RA associated genetic variation, e.g. SNP, is analysed in the present genotyping methods. The present methods allow simultaneous genotyping of multiple variations in an individual and typically multiple variations are analysed, in general, at least 10, 12, 14, 16, 18 or 20 RA associated genetic variations. For example, at least 25, 30, 35, 40, 45, 50, 55, 60, 65, 70, 75, 80, 85, 90, 95, 100, 105 or 110 variations or up to 150, 200, 300, 400, 500, or 600 variations may be tested, such as 250, 350 or 450 variations.

Thus the genotyping methods may be used for genotyping an individual with respect to all of or a selection of the variations in Table 1A or 1B, as described herein. For example, at least 1, 2, 3, 4, 5, 10, 15, 20, 25, 30, 35, 40, 45, 50, 55, 60, 65, 70, 75, 80, 85 or all of the Table 1A or 1B variations may be genotyped. The variations to be detected may additionally include other RA associated genetic variations.

The present invention also encompasses methods in which other genetic variations are assessed in addition to the RA associated genetic variations.

According to the present methods, a sample is provided, containing nucleic acid which comprises at least one of the genetic variations to be tested (the target DNA). Suitable samples and methods for obtaining the samples are described herein in relation to the prognostic methods.

As described, DNA regions which contain the genetic variations to be identified (target DNA regions) may be subjected to an amplification reaction in order to obtain amplification products which contain the genetic variations to be identified. Any suitable technique or method may be used for amplification. In general, the technique allows the (simultaneous) amplification of all the DNA sequences containing the genetic variations to be identified. In other words, where multiple genetic variations are to be analysed, it is preferable to simultaneously amplify all of the corresponding target DNA regions (comprising the variations). Carrying out the amplification in a single step (or as few steps as possible) simplifies the method.

For example, multiplex PCR may be carried out, using appropriate pairs of oligonucleotide PCR primers which are capable of amplifying the target regions containing the genetic variations to be identified. Any suitable pair of primers which allow specific amplification of a target DNA region may be used. In one aspect, the primers allow amplification in the least possible number of PCR reactions. Thus, by using appropriate pairs of oligonucleotide primers and appropriate conditions, all of the target DNA regions necessary for genotyping the genetic variations can be amplified for genotyping (e.g. DNA-chip) analysis with the minimum number of reactions. Suitable PCR primers for amplification of target DNA regions comprising the RA-associated genetic variations in Table 1A and 1B are listed in Tables 3. The present method may comprise the use of one or more of these primers or one or more of the listed primer pairs. For example, the present methods may be used for genotyping of Table 1A variations selected as described above. The corresponding primers in Table 3 may be selected for use accordingly.

In one instance, the amplification products can be labelled during the amplification reaction with a detectable label. The aim is to be able to later detect hybridisation between the fragments of target DNA containing the genetic variations being analysed and probes fixed on a solid support. The greater the extent of hybridisation of labelled target DNA to a probe, the greater the intensity of detectable label at that probe position.

The amplification products may be labelled by conventional methods. For example, a labelled nucleotide may be incorporated during the amplification reaction or labelled primers may be used for amplification.

Labelling may be direct using for example, fluorescent or radioactive markers or any other marker known by persons skilled in the art. Examples of fluorophores which can be used, include for example, Cy3 or Cy5. Alternatively enzymes may be used for sample labelling, for example alkaline phosphatase or peroxidase. Examples of radioactive isotopes which can be used include for example $^{33}$P, $^{125}$I, or any other marker known by persons skilled in the art. In one instance, labelling of amplification products is carried out using a nucleotide which has been labelled directly or indirectly with one or more fluorophores. In another example, labelling of amplification products is carried out using primers labelled directly or indirectly with one or more fluorophores.

Labelling may also be indirect, using, for example, chemical or enzymatic methods. For example, an amplification product may incorporate one member of a specific binding pair, for example avidin or streptavidin, conjugated with a fluorescent marker and the probe to which it will hybridise may be joined to the other member of the specific binding pair, for example biotin (indicator), allowing the probe/target binding signal to be measured by fluorimetry. In another example, an amplification product may incorporate one member of a specific binding pair, for example, an anti-dioxigenin antibody combined with an enzyme (marker) and the probe to which it will hybridise may be joined to the other member of the specific binding pair, for example dioxigenin (indicator). On hybridization of amplification product to probe the enzyme substrate is converted into a luminous or fluorescent product and the signal can be read by, for example, chemiluminescence or fluorometry.

The nucleic acid comprising the genetic variation(s) to be tested, e.g. the (optionally labelled) amplification products, may further undergo a fragmentation reaction, thereby obtaining some fragmentation products which comprise or contain the genetic variations to be identified or analysed. Typically fragmentation increases the efficiency of the hybridisation reaction. Fragmentation may be carried out by any suitable method known in the art, for example, by contacting the nucleic acid, e.g. the amplification products with a suitable enzyme such as a DNase.

If the nucleic acid has not been previously labelled, e.g. during the amplification reaction, (and, typically, where no posthybridisation amplification or ligation is carried out on the solid support) then labelling with a detectable label may be carried out prehybridisation by labelling the fragmentation products. Suitable labelling techniques are known in the art and may be direct or indirect as described herein. Direct labelling may comprise the use of, for example, fluorophores, enzymes or radioactive isotopes. Indirect labelling may comprise the use of, for example, specific binding pairs that incorporate e.g. fluorophores, enzymes, etc. For example, if amplification products have not been labelled during the amplification reaction the fragmentation products may undergo a direct or indirect labelling with one or various markers, for example one or various fluorophores, although other known markers can be used by those skilled in the art.

According to the present methods the nucleic acid, e.g. the amplification or fragmentation products, comprising the genetic variation(s) to be detected (target DNA), is contacted with oligonucleotide probes which are capable of detecting the corresponding genetic variations by hybridisation under suitable conditions.

Typically the hybridisation conditions allow specific hybridisation between probes and corresponding target nucleic acids to form specific probe/target hybridisation complexes while minimising hybridisation between probes carrying one or more mismatches to the DNA. Such conditions may be determined empirically, for example by varying the time and/or temperature of hybridisation and/or the number and stringency of the array washing steps that are performed following hybridisation and are designed to eliminate all probe-DNA interactions that are inspecific.

In the method, the probes are provided deposited on a solid support or surface. The probes are deposited at positions on the solid support according to a predetermined pattern, forming a "DNA-chip". It has been found that the chips should comply with a number of requirements in order to be used in the present methods, for example in terms of the design of the probes, the number of probes provided for each genetic variation to be detected and the distribution of probes on the support. These are described in detail herein. The inventors have developed suitable genotyping chips for use in the present methods and accordingly in one aspect the invention provides a DNA-chip or (micro)array comprising a plurality of probes deposited or immobilised on a solid support as described herein.

In general the solid support or phase comprises oligonucleotide probes suitable for detection of each genetic variation to be tested in the present method. The number and type of genetic variations to be tested using a chip may be selected as described herein.

Typically there will be at least one probe which is capable of hybridising specifically to genetic variation A (e.g. a wildtype or normal allele) (probe 1) and one probe which is capable of hybridising specifically to genetic variation B (e.g. a mutant allele) (probe 2) under the selected hybridisation conditions. These probes form a probe pair. Probe 1 is for detection of genetic variation A and probe 2 for detection of genetic variation B. Typically the probes can be used to discriminate between A and B (e.g. the wildtype and mutant alleles).

The probes may examine either the sense or the antisense strand. Typically, probes 1 and 2 examine the same nucleic acid strand (e.g. the sense strand or antisense strand) although in some cases the probes may examine different strands. In one aspect probes 1 and 2 have the same sequence except for the site of the genetic variation.

In one instance, the probes in a probe pair have the same length. In some aspects, where two or more pairs of probes are provided for analysis of a genetic variation, the probes may all have the same length.

Preferably more than one probe pair is provided for detection of each genetic variation. Thus, at least 2, 3, 4, 5, 6, 7, 8, 9, 10 or more probe pairs may be provided per genetic variation. In one aspect, (at least) 2 probe pairs are provided. The aim is to reduce the rate of false positives and negatives in the present methods.

For example, for a given genetic variation there may be:
Probe 1 which is capable of hybridising to genetic variation A (e.g. a normal allele)
Probe 2 which is capable of hybridising to genetic variation B (e.g. a mutant allele)
Probe 3 which is capable of hybridising to genetic variation A (e.g. a normal allele)
Probe 4 which is capable of hybridising to genetic variation B (e.g. a mutant allele).

The probes may examine the same or different strands. Thus in one embodiment, probes 3 and 4 are the complementary probes of probes 1 and 2 respectively and are designed to examine the complementary strand. In one aspect it is preferred that the probes provided for detection of each genetic variation examine both strands.

More than 2 pairs of probes may be provided for analysis of a genetic variation as above. For example, where a genetic variation exists as any one of 4 bases in the same strand (e.g. there are three mutant possibilities), at least one pair of probes may be provided to detect each possibility. Preferably, at least 2 pairs of probes are provided for each possibility.

Thus, for example, for an SNP G2677T/A/C, at least one pair of probes may be provided for detection of G2677T, one pair for detection of G2677/A, and one pair for detection of G2677C. Preferably at least two pairs of probes are provided for each of these substitutions.

A number of methods are known in the art for designing oligonucleotide probes suitable for use in DNA-chips.

A "standard tiling" method may be used. In this method, 4 oligonucleotides are designed that are totally complementary to the reference sequence except in the central position where, typically the 4 possible nucleotides A, C, G and T are examined. An illustrative example of this strategy is the DNA-chip for genotyping of HIV-1 (Affymetrix).

In "alternative tiling" 5 oligonucleotides are designed, so that the fifth examines a possible deletion in the sequence. An example of this strategy is the DNA-chip to detect mutations in p53 (Affymetrix).

In "block tiling" 4 oligonucleotides are designed that are totally complementary to the normal sequence and another 4 totally complementary to the mutant sequence. The nucleotide which changes is placed in the central position, but a mismatch of one of the 4 bases (A, C, T or G) is placed 2 nucleotides before or after the nucleotide position that it is wished to interrogate. An example of this strategy is the DNA-chip for the detection of mutations in cytochrome p450 (Roche and Affymetrix).

A further example is "alternative block tiling" where the "mismatch" is used to increase the specificity of the hybrid not only in one position but also in the positions −4, −1, 0, +1 and +4 to identify the change produced in the central position or 0. An example is the DNA-chip to detect 1,500 SNPs (Affymetrix).

Any one or more of these strategies may be used to design probes for the present invention. Preferably standard tiling is used, in particular with 2 pairs of probes e.g. 2 pairs of complementary probes as above. Thus it is preferable that the oligonucleotide sequence is complementary to the target DNA or sequence in the regions flanking the variable nucleotide(s). However, in some cases, one or more mismatches may be introduced, as described above.

The oligonucleotide probes for use in the present invention typically present the base to be examined (the site of the genetic variation) at the centre of the oligonucleotide. This is particularly the case where differential hybridisation methods are used, as in general this allows the best discrimination between matched and mismatched probes. In these methods, typically there is formation of specific detectable hybridisation complexes without post-hybridisation on-chip amplification. For example, for precise (single base) mutations, the base which differs between the normal and the mutant allele is typically placed in the central position of the probe. In the case of insertions, deletions and duplications, the first nucleotide which differs between the normal and the mutant sequence is placed in the central position. It is believed that placing the mutation at the centre of the probe maximises specificity.

Where post-hybridisation on-chip amplification (e.g. ligation or primer extension methods) is employed, oligonucleotide probes typically present the variable base(s) at the 3' end of the probe. Where OLA methodology is used, oligonucleotides (labelled directly or indirectly) are also designed which hybridise to probe-target complexes to allow ligation.

In general the probes for use in the present invention comprise or in some embodiments consist (essentially) of 17 to 27 nucleotides, for example, 19, 21, 23, or 25 nucleotides or 18, 20, 22, 24 or 26 nucleotides.

Preferably the individual probes provided for detection of a genetic variation are capable of hybridising specifically to the normal and mutant alleles respectively under the selected hybridisation conditions. For example, the melting temperature of the probe/target complexes may occur at 75-85° C. and hybridisation may be for one hour, although higher and lower temperatures and longer or shorter hybridisations may also suffice.

The probes provided for (suitable for) detection of each genetic variation (as described above) are typically capable of discriminating between genetic variation A and B (e.g. the normal and mutant alleles) under the given hybridisation conditions as above. Preferably the discrimination capacity of the probes is substantially 100%. If the discrimination capacity is not 100%, the probes are preferably redesigned. Preferably the melting temperature of the probe/target complexes occurs at 75-85 degrees C. Methods for testing discrimination capacity are described herein.

In one example, the probes provided for detection of a genetic variation examine both strands and have lengths ranging from 19-27 nucleotides. Preferably the probes have 100% discrimination capacity and the melting temperature of probe/target complexes is 75-85 degrees C.

Typically in order to obtain probes for use in the present methods, a number of probes are designed and tested experimentally for, e.g. hybridisation specificity and ability to discriminate between genetic variants (e.g. a normal and a mutant allele). Candidate oligonucleotide probe sequences may be designed as described above. These may vary for example in length, strand specificity, position of the genetic variation and degree of complementarity to the sequence flanking the genetic variation in the target DNA. Once probe pairs have been designed, these can be tested for hybridisation specificity and discrimination capacity. The capacity of specific probes to discriminate between the genetic variations A and B (e.g. normal and mutant alleles) depends on hybridisation conditions, the sequence flanking the mutation and the secondary structure of the sequence in the region of the mutation. By using stable hybridisation conditions, appropriate parameters such as strand specificities and lengths can be established in order to maximise discrimination. Preferably, the genetic variation is maintained at the central position in the tested probes.

Methods for testing discrimination capacity of probes are described herein. Typically a number of candidate probe pairs are provided and used in a training method as described below. In general two pairs of probes (probes 1 and 2, and probes 3 and 4) are tested in the method. For example, two pairs of probes examining both strands (complementary to each other) may be tested. If it is not possible to obtain 100% discrimination between the three genotyping groups using the probes, the probes are typically redesigned. Hybridisation conditions in the training method are generally maintained stably. Typically the melting temperature of probe/target complexes is 75-85° C.

For example, starting from probes of 25 nucleotides which detect a genetic variation (e.g. the normal allele) and another genetic variation (e.g. a mutant allele) in both strands (sense and antisense), in general an average of 8 probes may be experimentally tested to identify two definite pairs.

Probes are chosen to have maximum hybridisation specificity and discrimination capacity between genetic variants (e.g. a normal and a mutant allele) under suitable hybridisation conditions. For example, the probes for detection of a given genetic variation, e.g. two probe pairs, typically have substantially 100% discrimination capacity. Typically the melting temperature of probe/target complexes is at 75-85° C.

Using the methods herein the inventors have developed oligonucleotide probes suitable for detection of the RA-associated genetic variations in Table 1A and 1B. These probes are presented as SEQ ID NOS 1-360 (Table 2). The probes are listed in probe sets (90 sets in total), according to the genetic variation to be detected. At least two pairs of probes are listed in each set.

In one aspect the invention relates to any one or more of the oligonucleotide probes, pairs of probes or sets of probes set out in SEQ ID NOS 1-360 (Table 2), and to their use in the genotyping, diagnostic or prognostic or therapeutic methods of the invention. The invention further relates to any one or more of the oligonucleotide probes, pairs of probes or sets of probes set out in SEQ ID NOS 1-360 for use in medicine, for example in a diagnostic or prognostic or therapeutic method described herein. A chip of the invention may comprise one or more of the listed probe pairs or sets as described herein.

In general probes are provided on the support in replicate. Typically, at least 4, 6, 8, 10, 12, 14, 16, 18 or 20 replicates are provided of each probe, in particular, 6, 8 or 10 replicates. Thus for example, the support (or DNA-chip) may comprise or include 10 replicates for each of (at least) 4 probes used to detect each genetic variation (i.e. 40 probes). Alternatively the support (or DNA-chip) may comprise or include 8 replicates for each of (at least) 4 probes used to detect each genetic variation (i.e. 32 probes). Still further the support (or DNA-chip) may comprise or include 6 replicates for each of (at least) 4 probes used to detect each genetic variation (i.e. 24 probes). Using probe replicates helps to minimise distortions in data interpretation from the chip and improves reliability of the methods.

In general the support also comprises one or more control oligonucleotide probes. These are also provided in replicate as above. Thus the support (or DNA-chip) may additionally comprise one or more oligonucleotides deposited on the support which are useful as positive and/or negative controls of the hybridisation reactions. If post-hybridisation amplification or ligation reactions are carried out on the chip, there may also be one or more positive or negative controls of these reactions.

Typically the chip or array will include positive control probes, e.g., probes known to be complementary and hybridisable to sequences in the target polynucleotide molecules, probes known to hybridise to an external control DNA, and negative control probes, e.g., probes known to not be complementary and hybridizable to sequences in the target polynucleotide molecules. The chip may have one or more controls specific for each target, for example, 2, 3, or more controls. There may also be at least one control for the array.

Positive controls may for example be synthesized along the perimeter of the array or in diagonal stripes across the array. The reverse complement for each probe may be synthesized next to the position of the probe to serve as a negative control. In yet another example, sequences from other species of organism may be used as negative controls in order to help determine background (non-specific) hybridisation.

As above, the support (or DNA-chip) may include some (one or more) oligonucleotides deposited on the support which are useful as positive and negative controls of the hybridization reactions. In general, each one of the sub-arrays, for example 16, which typically constitute a DNA-chip, is flanked by some external hybridization controls, which serve as reference points allowing allow the points within the grid to be located more easily.

In one instance, the nucleotide sequence of an external control DNA is the following (5->3'):

```
CEH:
                                    (SEQ ID NO: 541)
GTCGTCAAGATGCTACCGTTCAGGAGTCGTCAAGATGCTACCGTTCAGGA
``` and the sequences of the oligonucleotides for its detection are the following:

```
ON1:   CTTGACGACTCCTGAACGG      (SEQ ID NO: 542)

ON2:   CTTGACGACACCTGAACGG      (SEQ ID NO: 543)
```

Positive control probes are generally designed to hybridise equally to all target DNA samples and provide a reference signal intensity against which hybridisation of the target DNA (sample) to the test probes can be compared. Negative controls comprise either "blanks" where only solvent (DMSO) has been applied to the support or control oligonucleotides that have been selected to show no, or only minimal, hybridisation to the target, e.g. human, DNA (the test DNA). The intensity of any signal detected at either blank or negative control oligonucleotide features is an indication of non-specific interactions between the sample DNA and the array and is thus a measure of the background signal against which the signal from real probe-sample interactions must be discriminated.

Desirably, the number of sequences in the array will be such that where the number of nucleic acids suitable for detection of genetic variations is n, the number of positive and negative control nucleic acids is n', where n' is typically from 0.01 to 0.4n.

In general, the support or chip is suitable for genotyping RA associated genetic variations, in particular, genotyping according to the present methods. The chip typically comprises probes suitable for detection of at least one but preferably multiple, RA associated genetic variation(s), typically at least 10, 12, 14, 16, 18 or 20 variations. For example, at least 25, 30, 35, 40, 45, 50, 55, 60, 65, 70, 75, 80, 85, 90, 95, 100, 105 or 110 variations or up to 150, 200, 300, 400, 500, or 600 variations may be tested, such as 250, 350 or 450 variations.

The RA associated genetic variations may include any or all of those in Table 1A or 1B. Thus an array or chip may comprise probes suitable for genotyping an individual with respect to all of the variations in Table 1A or 1B, or a selection of the variations in the Table, as described herein.

A DNA-chip according to the invention ('Artchip') allows simultaneous, sensitive, specific and reproducible genotyping of genetic variations associated with RA. Non-limiting examples of such variations are given in Table 1A and 1B. Nevertheless, the number of genetic variations contained in the Table can be increased as other genetic variations are subsequently identified and are associated with RA. Thus the genetic variations detectable by the chip may comprise, or consist (essentially) of those listed in Table 1A or Table 1B or FIG. 11 or a selection of these, as described in relation to the present methods. The chip will comprise probes suitable for detection of these genetic variations as described herein. Preferably where a chip comprises probes for detection of a genetic variation in Table 1A the chip comprises one or more of the probes listed in SEQ ID NOS 1-360 (Table 2) as suitable for detection of that genetic variation, e.g. the probes set listed in SEQ ID NOs 1-360 for detection of that variation. In one aspect the present chip comprises one or more probes selected from those in SEQ ID NOS 1-360. The probes are listed in probe sets, according to the genetic variation to be detected. At least two pairs of probes are provided in each set. A chip may comprise at least one probe pair or at least one probe set, or a selection of the probe sets, for example a probe pair or a probe set from at least 5, 10, 15, 20, 25, 30, 35, 40, 45, 50, 55, 60, 65, 70, 75, 80, 85 or all 90 sets, according to the genetic variations being tested. A chip may comprise other probes for detection of variations in Table 1A or other variations associated with RA instead of or in addition to those specifically listed.

Artchip may additionally comprise oligonucleotide probes for detection of genetic variations not associated with RA. For example, the chips may comprise probes for detection of genetic variations such as SNPs associated with another (related) condition such as colon, rectal or bladder cancer. Typically, in Artchip, the number of nucleic acids suitable for detection of genetic variations associated with RA (e.g. those in Table 1A or Table 1B or FIG. 11) represent at least 50%, 60%, 70%, 75%, 80%, 85%, 90%, 95%, 97%, 98%, 99% or more of the nucleic acids in the array.

In general the support or chip has from 300 to 40000 nucleic acids (probes), for example, from 400 to 30000 or 400 to 20000. The chip may have from 1000 to 20000 probes, such as 1000 to 15000 or 1000 to 10000, or 1000 to 5000. A suitable chip may have from 2000 to 20000, 2000 to 10000 or 2000 to 5000 probes. For example, a chip may have 1000, 2000, 3000, 4000, 5000, 6000, 7000, 8000, 9000, 10000, 12000, 14000, 16000, 18000 or 20000 probes. Smaller chips 400 to 1000 probes, such as 400, 500, 600, 700, 800, 900 or 950 probes are also envisaged.

In general the array or chip of the invention comprises a support or surface with an ordered array of binding (e.g. hybridisation) sites or probes. Thus the arrangement of probes on the support is predetermined. Each probe (i.e each probe replicate) is located at a known predetermined position on the solid support such that the identity (i.e. the sequence) of each probe can be determined from its position in the array. Typically the probes are uniformly distributed in a predetermined pattern.

Preferably, the probes deposited on the support, although they maintain a predetermined arrangement, are not grouped by genetic variation but have a random distribution. Typically they are also not grouped within the same genetic variation. If desired, this random distribution can be always the same. Therefore, typically the probes are deposited on the solid support (in an array) following a predetermined pattern so that they are uniformly distributed, for example, between the two areas that may constitute a DNA-chip, but not grouped according to the genetic variation to be characterised. Distributing probe replicates across the array in this way helps to reduce or eliminate any distortion of signal and data interpretation, e.g. arising from a non-uniform distribution of background noise across the array.

As explained above, probes may be arranged on the support in subarrays.

The support, on which the plurality of probes is deposited, can be any solid support to which oligonucleotides can be attached. Practically any support, to which an oligonucleotide can be joined or immobilized, and which may be used in the production of DNA-chips, can be used in the invention. For example, the said support can be of a non-porous material, for example, glass, silicone, plastic, or a porous material such as a membrane or fitter (for example, nylon, nitrocellulose) or a gel. In one embodiment, the said support is a glass support, such as a glass slide.

Microarrays are in general prepared by selecting probes which comprise a given polynucleotide sequence, and then immobilizing such probes to a solid support or surface. Probes may be designed, tested and selected as described herein. In general the probes may comprise DNA sequences. In some embodiments the probes may comprise RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Microarrays or chips can be made in a number of ways. However produced, microarrays typically share certain characteristics. The arrays are reproducible, allowing multiple copies of a given array to be produced and easily compared with each other. Preferably, microarrays are made from materials that are stable under binding (e.g., nucleic acid hybridization) conditions. The microarrays are preferably small, e.g., between 0.25 to 25 or 0.5 to 20 $cm^2$, such 0.5 to 20 $cm^2$ or 0.5 to 15 $cm^2$, for example, 1 to 15 $cm^2$ or 1 to 10 $cm^2$, such as 2, 4, 6 or 8 $cm^2$.

Probes may be attached to the present support using conventional techniques for immobilization of oligonucleotides on the surface of the supports. The techniques used depend, amongst other factors, on the nature of the support used [porous (membranes, micro-particles, etc.) or non-porous (glass, plastic, silicone, etc.)] In general, the probes can be immobilized on the support either by using non-covalent immobilization techniques or by using immobilization techniques based on the covalent binding of the probes to the support by chemical processes.

Preparation of non-porous supports (e.g., glass, silicone, plastic) requires, in general, either pre-treatment with reactive groups (e.g., amino, aldehyde) or covering the surface of the support with a member of a specific binding pair (e.g. avidin, streptavidin). Likewise, in general, it is advisable to pre-activate the probes to be immobilized by means of corresponding groups such as thiol, amino or biotin, in order to achieve a specific immobilization of the probes on the support.

The immobilization of the probes on the support can be carried out by conventional methods, for example, by means of techniques based on the synthesis in situ of probes on the support (e.g., photolithography, direct chemical synthesis, etc.) or by techniques based on, for example, robotic arms which deposit the corresponding pre-synthesized probe (e.g. printing without contact, printing by contact).

In one embodiment, the support is a glass slide and in this case, the probes, in the number of established replicates (for example, 6, 8 or 10) are printed on pre-treated glass slides, for example coated with aminosilanes, using equipment for automated production of DNA-chips by deposition of the oligonucleotides on the glass slides ("micro-arrayer"). Deposition is carried out under appropriate conditions, for example, by means of crosslinking with ultraviolet radiation and heating (80° C.), maintaining the humidity and controlling the temperature during the process of deposition, typically at a relative humidity of between 40-50% and typically at a temperature of 20° C.

The replicate probes are distributed uniformly amongst the areas or sectors (sub-arrays), which typically constitute a DNA-chip. The number of replicas and their uniform distribution across the DNA-chip minimizes the variability arising from the printing process that can affect experimental results. Likewise, positive and negative hybridisation controls (as described herein) may be printed.

To control the quality of the manufacturing process of the DNA-chip, in terms of hybridization signal, background noise, specificity, sensitivity and reproducibility of each replica as well as differences caused by variations in the morphology of the spotted probe features after printing, a commercial DNA can be used. For example, as a quality control of the printing of the DNA-chips, hybridization may be carried out with a commercial DNA (e.g. k562 DNA High Molecular Weight, Promega).

In the first place, the morphology and size of the printed spots are analyzed. In the hybridization with control DNA the parameters described below for determining reliability of genotype determination, are adhered to; specifically the relationship between the signal intensity and background noise, average specificity and sensitivity and reproducibility between replicated copies of the same probe. This method allows the correct genotype of the control DNA to be determined.

As above, in accordance with the present method, a nucleic acid sample, e.g. amplification or fragmentation products, comprising the genetic variation(s) to be detected (target DNA) is contacted with a probe array as described herein, under conditions which allow hybridisation to occur between target DNA and the corresponding probes. Specific hybridisation complexes are thus formed between target nucleic acid and corresponding probes.

The hybridization of e.g. fragmentation products, with probes capable of detecting corresponding genetic variations deposited on a support may be carried out using conventional methods and devices. In one instance, hybridization is carried out using an automated hybridisation station. For hybridization to occur, the e.g. fragmentation products, are placed in contact with the probes under conditions which allow hybridization to take place. Using stable hybridization conditions allows the length and sequence of the probes to be optimised in order to maximize the discrimination between genetic variations A and B, e.g. between wild type and mutant sequences, as described herein.

In one instance, the method relies on differential hybridisation, in particular an increase in hybridisation signal. The method involves formation of specific hybridisation complexes between target DNA and corresponding probes. Thus target DNA bearing the wild type sequence will hybridise to the probes designed to detect the wild type sequence, whereas target DNA bearing a mutant sequence will hybridise to the probes designed to detect that mutant sequence. The hybridisation complexes are detectably labelled by means described herein (e.g. the target DNA is directly labelled, or both target and probe are labelled in such a way that the label is only detectable on hybridisation). By detecting the intensity of detectable label (if any) at the predetermined probe positions it is possible to determine the nature of the target DNA in the sample. In this instance the probes (also referred to as allele specific oligonucleotides, ASOs) preferably have the variable nucleotide(s) at the central position, as described herein.

In another instance, hybridisation of target DNA to probes on the solid support (chip) may be followed by on-chip amplification, for example, using primer extension or ligation, e.g. oligonucleotide ligation assay (OLA) technologies (Eggerding F A, Iovannisci D M, Brinson E., Grossman P., Winn-Deen E. S. 1995 Human Mutation, 5:153-65). In this case, the probes on the support typically comprise the variable nucleotide(s) at the 3' end of the probe.

Labelling can be carried out during post hybridisation amplification. The labelling can be by direct labelling using, for example, fluorophores, enzymes, radioactive isotopes, etc. or by indirect labelling using, for example, specific binding pairs which incorporate fluorophores, enzymes etc., by using conventional methods, such as those previously mentioned in relation to labelling amplification or fragmentation products.

Post-hybridization amplification may be carried out, for example, using the "primer extension" methodology. Typically, after hybridization, an extension reaction of the hybrid oligonucleotides is carried out on the support (e.g. a glass slide). Extension may be carried out with directly or indirectly labelled nucleotides and will only happen if the extreme 3' of the oligonucleotide hybridizes perfectly with the amplification product.

Primer extension is a known method for genotype discrimination (Pastinen T, Raitio M, Lindroos K, Tainola P, Peltonen L, Syvanen A C. 2000 Genome Research 10:1031-42.) and can be performed in a number of different ways. In a commonly used approach a set of allele specific oligonucleotide probes are designed to hybridise to the target sequences. The probes differ from one another in their extreme 3' nucleotide, which for each probe is designed to complement one of the possible polymorphic nucleotides at a given position.

When the 3' nucleotide of the probe complements the sequence under test then the ensuing base pairing allows a DNA polymerase to extend the oligonucleotide primer by incorporation of additional nucleotides that can be directly or indirectly labelled thereby allowing the subsequent identification of those probes that have been extended and those that have not. Probes that are successfully extended carry the complementary nucleotide to the SNP at their 3' end thus allowing the genotype of the test sample to be determined. Similar approaches, for example the Amplification Refractory Mutation System (ARMS) have also been developed.

Alternatively, a post hybridization ligation reaction may be carried out, for example using OLA methodology. After hybridization, a ligation reaction of the hybridised oligonucleotides is carried out on the support (e.g. glass slide) with labelled oligonucleotides. A ligation will only take place if the extreme 3' end of the probe deposited on the support hybridizes perfectly with the target DNA (e.g. amplification product).

The oligonucleotide ligation assay (OLA) is another method for interrogating SNPs (Eggerding F A, Iovannisci D M, Brinson E., Grossman P., Winn-Deen E. S. 1995 Human Mutation, 5:153-65). OLA uses a pair of oligonucleotide probes that hybridize to adjacent segments of target DNA including the variable base. The probe designed to hybridise to the 5' side of the polymorphic nucleotide is an allele-specific oligonucleotide (ASO) to one of the target alleles. The last base at the 3' end of this ASO is positioned at the site of the target DNA's polymorphism; the ASO typically also has a biotin molecule at its 5' end that functions as a "hook" that can subsequently be used to recover the oligonucleotide by virtue of the highly specific interaction that biotin undergoes with streptavidin.

The oligomer on the 3' or right-hand side of the pair is the common oligomer (the sequence is the same for the two or more different alleles it is wished to test.) The common oligomer is positioned at an invariable site next to the target DNA's polymorphism and is fluorescently labelled at its 3' end.

If the ASO is perfectly complementary to the target sequence the ASO hybridizes completely when annealed and will lie flat against that target allowing DNA ligase to covalently join the ASO to the common oligomer. After the ligation reaction the biotin hook is used to remove the ASO and the e.g. fluorescently labeled common oligomer will also be removed, producing detectable fluorescence.

When the ASO is not a perfect match to the target sequence hybridization is incomplete and the 3' base of the oligomer will not be base-paired to the target DNA thus preventing ligation. Under these circumstances when the biotin hook is used to remove the ASO, the common oligonucleotide will not be removed and therefore there is no detectable label, e.g. fluorescence, in the molecule removed.

To distinguish between two known alleles that differ by a single base, three oligonucleotides are necessary: Two are allele-specific oligonucleotides (ASOs) that differ from each other only in the single 3' terminal base; the first is complementary to one allele and the second is complementary to the second allele. The third oligonucleotide is complementary to the invariable sequence adjacent to the variant base.

Once hybridisation (and optionally post-hybridisation amplification) has taken place, the intensity of detectable label at each probe position (including control probes) can be determined. The intensity of the signal (the raw intensity value) is a measure of hybridisation at each probe.

The intensity of detectable label at each probe position (each probe replica) may be determined using any suitable means. The means chosen will depend upon the nature of the label. In general an appropriate device, for example, a scanner, collects the image of the hybridized and developed DNA-chip. An image is captured and quantified.

In one instance, e.g. where fluorescent labelling is used, after hybridization, (optionally after post-hybridization amplification or ligation) the hybridized and developed DNA-chip is placed in a scanner in order to quantify the intensity of labelling at the points where hybridization has taken place. Although practically any scanner can be used, in one embodiment a fluorescence confocal scanner is used. In this case, the DNA-chip is placed in the said apparatus and the signal emitted by the fluorpohore due to excitation by a laser is scanned in order to quantify the signal intensity at the points where hybridization has taken place. Non-limiting examples of scanners which can be used according to the present invention, include scanners marketed by the following companies: Axon, Agilent, Perkin Elmer, etc.

Typically, in determining the intensity of detectable label at each probe position (i.e. for each probe replica), account is taken of background noise, which is eliminated. Background noise arises because of non-specific binding to the probe array and may be determined by means of controls included in the array. Once the intensity of the background signal has been determined, this can be subtracted from the raw intensity value for each probe replica in order to obtain a clean intensity value. Typically the local background, based on the signal intensity detected in the vicinity of each individual feature is subtracted from the raw signal intensity value. This background is determined from the signal intensity in a predetermined area surrounding each feature (e.g. an area of X, Y or Z μm2 centred on the position of the probe).

The background signal is typically determined from the local signal of "blank" controls (solvent only). In many instances the device, e.g. scanner, which is used to determine signal intensities will provide means for determining background signal.

Thus, for example, where the label is a fluorescent label, absolute fluorescence values (raw intensity values) may be gathered for each probe replica and the background noise associated with each probe replica can also be assessed in order to produce "clean" values for signal intensity at each probe position.

Once the target DNA has been hybridised to the chip and the intensity of detectable label has been determined at the probe replica positions on the chip (the raw intensity values), it is necessary to provide a method (model) which can relate the intensity data from the chip to the genotype of the individual.

The inventors have found that this can be done by applying a suitable algorithm to the intensity data. The algorithm and computer software developed by the inventors allows analysis of the genetic variations with sufficient sensitivity and reproducibility as to allow use in a clinical setting. The algorithm uses three linear functions which characterise each of the three genotypes AA, AB and BB for a given genetic variation. The method generally involves collating the intensity values for all of the replicas of each probe, to calculate an average intensity value for each probe. Optionally, the raw intensity values for each replica may be amended to take account of background noise (to obtain a clean intensity value) before the intensity values for each of the replicas are collated.

In general, for a given genetic variation, analysis and interpretation of a chip comprises the following steps:

(a) providing the intensity of detectable label at each replica for each of at least four probes (probes 1, 2, 3 and 4) provided for detection of the genetic variation (the raw intensity value), wherein:
   probe 1 detects (is capable of specifically hybridising to) genetic variation A (e.g. a normal allele), and probe 2 detects (is capable of specifically hybridising to) genetic variation B (e.g. a mutant allele);
   probe 3 detects (is capable of specifically hybridising to) genetic variation A (e.g. a normal allele) and probe 4 detects (is capable of specifically hybridising to) genetic variation B (e.g. a mutant allele); and
   probes 1 and 2 form a first probe pair and probes 3 and 4 form a second probe pair;

(b) optionally amending the raw intensity value for each replica to take account of background noise, thus obtaining a clean intensity value;

(c) collating the (optionally clean) intensity values for each of the replicas of each probe and determining an average intensity value for each probe;

(d) calculating ratios 1 and 2 wherein:

$$\text{Ratio } 1 = \frac{\text{average intensity value for probe } 1}{\text{average intensity value for probe } 1 + \text{average intensity value for probe } 2}$$

and $$\text{Ratio } 2 = \frac{\text{average intensity value for probe } 3}{\text{average intensity value for probe } 3 + \text{average intensity value for probe } 4}$$

(e) inputting ratios 1 and 2 into each of three linear functions which characterise each of the three possible genotypes, AA, AB and BB, wherein:
   Function 1 is the linear function that characterises individuals with the genotype AA and consists of a linear combination of ratios 1 and 2;
   Function 2 is the linear function that characterises individuals with the genotype AB and consists of a linear combination of ratios 1 and 2;
   Function 3 is the linear function that characterises individuals with the genotype BB and consists of a linear combination of ratios 1 and 2;
   the linear functions are formed by coefficients which accompany the variables ratio 1 and 2;

(f) determining which of the three linear functions has the highest value; and (g) thereby determining the genotype of the individual for the genetic variation.

Thus the linear function corresponding to the genotype of that individual will have the highest absolute value.

The inventors have found that the use of replicas and averages calculated from replicas is important for reliable working of the invention. Use of the functions speeds up analysis and allows better discrimination.

Preferably the discrimination capacity between the three genotypes is (approximately) 100%. If the discrimination is less than 100% the probes are preferably redesigned.

The raw intensity value for each probe replica may be determined according to the methods described above. Thus probe sequences and replicas can be selected as described herein. In one example, 4 probes are used per genetic variation and 6, 8 or 10 replicas are used per probe.

Typically, amending the raw intensity value to obtain the clean intensity value for each probe replica comprises subtracting background noise from the raw value. Background noise is typically determined using appropriate controls as described herein.

Typically calculating the average intensity value comprises eliminating extreme values or outliers. Thus, when the (optionally clean) intensity values from each of the probe replicas are collated, outlying values can be identified and excluded from further consideration. In one embodiment outliers make up between 10% and 50%, for example, 15, 20, 25, 30, 35, 40 or 45% of the values obtained. In one embodiment, 40% of values are eliminated. In one embodiment, 4 probes are used with 6, 8 or 10 replicas per probe and extreme values or outliers make up between 10% and 50% of the values obtained.

A number of suitable linear functions are known in the art. These functions may be used in a linear discriminant analysis for the purposes of the present invention.

In one aspect the invention thus relates to a computational method or model (algorithm) for determining genotype with respect to a given genetic variation using ratios 1 and 2 in the three linear functions as defined above (steps e and f). The method can thus in one embodiment produce an output of genotype (AA, AB or BB) from an input of ratios 1 and 2. The method may also include calculating one or both of ratios 1 and 2 (step d). In some embodiments the method additionally comprises calculating an average intensity value for each probe (step c) and/or calculating a clean intensity value for each probe replica (step b). Thus the input to the model may comprise one or more of the average intensity values, clean replica intensity values or raw replica intensity values. The method may additionally comprise determining the raw intensity value for each probe replica (step a). The method may comprise one or more of the above steps.

In order to carry out the above methods, the coefficients for the linear functions must first be determined in a training process using data from control individuals whose genotype for the genetic variation is already known. Methods for training are known in the art. Typically in such methods, input data (in this case, typically ratios 1 and 2) is used for which the output (in the present case, genotype) is already known. Coefficients are substituted in the three linear equations at random and the output is calculated. Based on that output, one or more coefficients are altered and the input data is entered again to produce another output. The process is continued until coefficients are obtained which optimise the desired output. These optimised coefficients are then used in the linear functions when the method is applied to test data (where the output is as yet unknown).

In order to train the present model, ratios 1 and 2 are obtained for n control individuals having genotype AA (for example, homozygous wild type), n control individuals having genotype AB (heterozygous) and n control individuals having genotype BB (for example, homozygous mutant). The ratios may be obtained using the methods described above. The ratios are inputted as above and the coefficients altered in a discriminatory analysis until three linear functions are obtained which maximise discrimination between the AA, AB and BB groups. These coefficients are then used in the three functions when the model is used on unknown test samples (where the genotype is not predetermined).

Thus in one aspect the invention provides a method of deriving linear functions for use in the present genotyping methods. The method typically comprises carrying out the steps of the genotyping methods as described, for n control individuals having genotype AA (for example, homozygous wild type), n control individuals having genotype AB (heterozygous) and n control individuals having genotype BB (for example, homozygous mutant) with respect to a genetic variation. The intensity values obtained for each of the probe replicas are gathered as described and an algorithm is applied.

As described for the genotyping methods, application of the algorithm comprises calculating an average intensity value for each probe and the algorithm uses three linear functions intended to characterise each of the three possible genotypes, AA, AB and BB for the given genetic variation. Coefficients are inserted in the functions in a repetitive way until functions are derived which maximise discrimination between the genotypes in a discriminatory analysis. This provides the coefficients for use in the linear functions when the method or algorithm is in operational use (i.e. to determine the genotype of test individuals).

The algorithm or method which uses the three linear functions for analysing the intensity data may be as described above.

In some cases, the training method allows feedback optimisation. Thus, as intensity values and ratios are obtained for test individuals and these are genotyped, the intensity data, e.g. the ratios, and genotype are inputted and coefficients recalculated for the linear functions.

In one aspect the invention relates to a computational method for training. The method can be used to derive linear functions for use in the present genotyping methods by using ratios 1 and 2 obtained for each of n individuals having genotype AA, n individuals having genotype AB and n individuals having genotype BB with respect to a genetic variation. The ratios can be obtained by the methods described above. The method typically comprises applying the algorithm which uses the three linear functions (Functions 1, 2 and 3) intended to characterise each of the three possible genotypes AA, AB or BB for the genetic variation such that:

Function 1 is the linear function that characterises individuals with the genotype AA and consists of a linear combination of ratios 1 and 2;

Function 2 is the linear function that characterises individuals with the genotype AB and consists of a linear combination of ratios 1 and 2;

Function 3 is the linear function that characterises individuals with the genotype BB and consists of a linear combination of ratios 1 and 2; and the linear functions are formed by coefficients which accompany the variables ratio 1 and 2;

and deriving linear functions which maximise discrimination between the three genotype groups AA, AB and BB in a discriminatory analysis, so as to obtain the coefficients which can be used in the linear functions when the algorithm is used in a test method (i.e. is in operational use for determining genotype).

The algorithm or method which uses the three linear functions for analysing the intensity data may be as described above.

The computational training method may additionally involve calculating ratios 1 and 2 from average intensity value provided for each of the probes, and/or collating intensity values from probe replicas to determine an average intensity value for each probe and/or amending a raw intensity value for a probe replica to take account of background noise thereby obtaining clean intensity values for the replica.

In some aspects the computational method also allows a feedback optimisation step as described.

Typically in training n is ≥3, for example, 3, 4, 5, 6, 7, 8, 9 or 10. In one aspect, n is ≥5. In some cases n may be from 10 to 50 or more, for example, 15 to 40, or 25 to 35, such as 20 or 30.

Probes and probe replicas for the training method are selected as described herein. In one embodiment 4 probes are used for each genetic variation, with 6, 8 or 10 replicas of each probe. Once selected, the probes used in training are also used when the model is in operational use (to determine unknown genotype). If the probes are altered, typically the model must be retrained to optimise discrimination with the new probes.

Preferably the coefficients are such that the discrimination between the three genotype groups (both in training and in operational use) is substantially 100%. If the discrimination is not 100%, the probes are preferably redesigned.

As above, the model may also undergo feedback optimisation when it is in operational use. In that case, the model is first used to determine the genotype of an individual (AA, AB or BB). The ratios 1 and 2 for that individual are then inputted into the model and the coefficients in the linear functions altered as necessary in order to optimise discrimination between the three genotype groups. In this way, the additional data gathered as the model is in use can be used to optimise the discrimination capacity of the linear functions.

There are a number of parameters which can be determined and optimised in order to optimise performance and reliability of the analytical model or method.

(i) In one aspect ratios 1 and 2 determined for an individual fall within the range of ratios 1 and 2 used to train the model (i.e. to optimise the three linear functions). If desired this can thus provide a double test for the genotype of an individual.
(ii) In one aspect the average fluorescence intensity of 4n replicas (where "n" is the number of replicas for each probe, e.g. 6, 8 or 10), for example, 40 replicas, with regard to the background noise is greater than 5.
(iii) In one aspect the variation between intensity values (raw or clean) for replicas of the same probe is a minimum. For example, the coefficient of variation between the intensity values for the replicas of a given probe is preferably less than 0.25
(iv) In one aspect the ratio of the sum of the raw intensity values for all probe replicas on a chip to the intensity of the background noise is greater than 15 when a fluorescence scanner is used.
(v) In one aspect the raw signal intensity value obtained for the negative controls is ≤3 times greater than the intensity value of the background noise. For example, negative controls may include the DMSO "blank" and the non-hybridising oligonucleotides referred to above. The background noise is the signal derived from the regions of the array where no probe has been spotted and may be determined as above.

Preferably any one or more of (i) to (v) applies when intensity is fluorescence intensity of a fluorescent label, in particular where the intensity is determined by means of a confocal fluorescent scanner.

Ensuring that the model meets one or more of the above helps to provide reliability and reproducibility. Any one or more of (i) to (v) may be true for the model. Preferably the model meets (i) above. In one example, (i), (ii) and (iii) are true. In another example, (iii), (iv), (v) are true. Preferably, all of the above are true for the model. This applies both to training and to operational use.

As above, the experimentally derived ratios obtained for a test sample may be compared to the ratios previously obtained for the (n) control samples obtained from individuals of known genotype, where n is as above, usually >5, or >10, or >20. The reference ratios derived from analysis of the control samples permits a genotype to be assigned to the test sample. This can therefore be a double test.

In one instance the analytical method or algorithm of the invention comprises a sequence of the following steps:

using 4 probes (2 pairs of probes) in replicate (6, 8 or 10 replicas), calculating the average intensity of each probe from the collated intensities of the replicas; calculating ratios 1 and 2 as above for the 2 pairs of probes (to detect the genetic variations A and B); substituting ratios 1 and 2 obtained in three linear equations which have been derived in a discriminatory analysis using ratios 1 and 2 calculated for "n" control patients with genotype AA, "n" control patients with genotype AB and "n" control patients with genotype BB (with respect to the genetic variation) (in one experiment "n" is 5); and determining the genotype of a patient for the genetic variation (for each genetic variation included in the DNA-chip) based on which linear function has the greatest absolute value. The test ratios may also be compared to the ratios of the "n" control patients to determine each genotype.

The analysis and interpretation above has been described with respect to one genetic variation. However, it is to be understood that the present chip generally includes probes for detection of multiple genetic variations which can be analysed at the same time. Thus the present methods include analysis of multiple genetic variations, as described herein, in parallel.

In a further aspect the invention relates to a computer system comprising a processor and means for controlling the processor to carry out a computational method of the invention.

The invention additionally relates to a computer program comprising computer program code which when run on a computer or computer network causes the computer or computer network to carry out a computational method of the invention. The computer program may be stored on a computer readable medium.

In addition to the probes and chips described herein, the inventors have also designed and validated oligonucleotide primers which are capable of amplifying, e.g. by means of multiplex PCR, target DNA regions containing the human genetic variations associated with RA in Table 1A. These primers are useful in preparing nucleic acid for use in the present genotyping, prognostic and therapeutic methods.

Table 3 lists pairs of primers which amplify target DNA regions containing the RA associated genetic variations in Table 1A (SEQ ID NOS 361-540) along with the corresponding genetic variation.

The listed oligonucleotide primers have the advantage of allowing specific amplification of the said target DNA regions in a very low number of PCR reactions. The listed primers allow, in a minimum number of multiplex PCR reactions, amplification of all the fragments necessary for genotyping the genetic variations in Table 1A, and which may be analyzed on Artchip.

In a further aspect, the present invention relates to each of the PCR primers listed in Table 3, and in particular to each of the listed pairs of PCR primers and their use in PCR amplification, e.g. in a multiplex PCR reaction, of a target DNA region containing the corresponding genetic variation. The invention in one aspect provides any one of these primers or pairs of primers for use in medicine, in particular for use in the present genotyping, prognostic or therapeutic methods.

The invention further relates to a PCR amplification kit comprising at least one pair of listed PCR primers. The kit may additionally include, for example, a (thermostable) polymerase, dNTPs, a suitable buffer, additional primers, and/or instructions for use, e.g. to amplify a target DNA region containing the corresponding genetic variation. The kit may be used for amplification of target DNA regions from nucleic acid samples, for use in the present methods.

In another aspect the present invention relates to a genotyping or diagnostic (preferably in vitro) kit for genotyping RA associated genetic variations and/or for diagnosing RA or susceptibility to RA. The kit comprises a DNA-chip or array according to the invention. The kit may additionally comprise instructions for use of the chip in a genotyping method of the invention, for example instructions for use in the present analytical method or algorithm. Further components of a kit may include:
- computer software, a computer program or a computer system according to the invention;
- one or more PCR primers or pairs of PCR primers according to the invention; and/or
- a PCR amplification kit according to the invention.

The probes for the chip or PCR primers may be selected as above depending on the genetic variations to be detected or the diagnostic purpose of the kit.

The kit may contain one or more positive and/or negative controls of the hybridisation reaction.

The invention further relates to the use of the kit in a genotyping, prognostic or therapeutic method of the invention.

As described herein, the present genotyping methods are useful for diagnosing RA or susceptibility to RA in a subject. The genotyping results obtained in the methods may be used to determine prognosis and may be useful in determining the appropriate treatment for RA (e.g. by predicting response to therapy).

RA presents a number of phenotypes, most notably in terms of disease severity. Mild disease is distinguished from severe and destructive disease, as well as the speed and nature of disease progression, and this clinical heterogeneity correlates with genetic heterogeneity.

Particular genetic variations associated with RA may be predictive of particular phenotypes or development of particular phenotypes and hence disease progression. In other words, it may be that there is a statistically significant association between e.g. the mutant allele B, of a given genetic variation and the occurrence/development of a particular phenotype.

Since the present genotyping methods allow reliable genotyping of multiple genetic variations in a clinical setting, these can be used to genotype individuals of known RA phenotype, and to thus identify genetic variations predictive of particular RA phenotypes.

In one aspect the invention therefore relates to a method of identifying genetic variations predictive of a particular RA phenotype, such as the phenotypes listed above. The method involves genotyping a plurality of individuals with respect to one or more genetic variations associated with RAa using a method of the invention. In such a retrospective study typically 300-1000 individuals are genotyped, for example 400, 500 or 600 individuals may be genotyped. The phenotype of each individual is already known based on standard clinical procedures.

Once the genotypes are obtained, this data is compared with the phenotype data and statistically significant associations between particular genotypes and particular phenotypes are identified. Methods for determining statistical significance are known in the art.

The genetic variations identified as predictive of particular phenotypes/disease course can then be used to diagnose these phenotypes/disease courses in test individuals, by genotyping the individuals with respect to the predictive genetic variation(s). Thus it is possible to determine the likely course of disease progression in the individual. Genotyping can be done by any appropriate method, depending on the number of variations to be tested. For example, a genotyping method of the invention may be used. Alternatively, sequence based or other chip-based methods may be appropriate.

Thus in one aspect the invention further relates to a method of diagnosing RA phenotype or predicting the likely course of disease progression in an individual by determining the genotype of the individual with respect to one or more genetic variations which have been identified as predictive (of the particular RA phenotype or disease course) by the methods described herein.

Once the prediction has been made, it will then be possible to select the most suitable therapeutic approach, e.g. to determine the need for surgical intervention.

The present arrays and methods thus provide a means for clinicians to predict the likely course of disease progression in RA patients and also aid in the selection of the most suitable treatment regime. They are therefore useful prognostic tools. Genotype information obtained according to the present invention may aid in clinical decision making or diagnosis in cases where symptoms (disease phenotype) are ambiguous. Genetic information provided by Artchip or other methods could also help in determining the likelihood of disease development in asymptomatic individuals (e.g. immediate family members of RA sufferers) allowing, for example, guidance on lifestyle and diet to be provided and indicating the need for continued monitoring of individuals who have a genetic constitution that indicates possible susceptibility to disease development.

In one aspect the invention therefore relates to a method of diagnosing RA or susceptibility to RA in an individual, or determining the likely course of disease progression in an individual as above.

Preferably the method is in vitro. The invention further relates to a method of selecting a treatment, for an individual having RA, in some cases where the individual has been diagnosed or tested according to the methods of the invention. Still further the invention in some aspects relates to methods of treating an individual suffering from RA, wherein, after the treatment is selected, the treatment is administered to the individual.

The diagnostic, predictive and therapeutic methods may comprise carrying out a genotyping method of the invention as described herein. Any of the methods may involve carrying out a training method of the invention as described herein in order to derive linear functions for use in determining genotype. Further the methods may comprise the use of a chip, computer system, computer program, oligonucleotide probes or pair or set of probes, oligonucleotide primer or pair of primers, PCR amplification kit or diagnostic kit of the invention as described herein.

Apart from the contribution to the diagnosis and treatment of RA and the development of new therapeutic strategies for this disease, the present invention is useful for elucidating the physiopathology of the inflammatory reaction in RA which will also be of great interest for the study of other diseases, of an autoimmune base, and belonging to fields so diverse such as pneumology, dermatology, etc.

In one aspect the present invention relates to a microarray adapted for use in the present methods as described herein.

The invention further relates to the use of one or more oligonucleotide probe(s) and/or one or more primer(s) or primer pair(s) of the invention in a method for prognosing RA, such as a method described herein.

Further aspects of the invention will now be illustrated with reference to the accompanying Figures and experimental exemplification, by way of example and not limitation. Further aspects and embodiments will be apparent to those of ordinary skill in the art. All documents mentioned in this specification are hereby incorporated herein by reference.

Examples

Although in general, the techniques mentioned herein are well known in the art, reference may be made in particular to Sambrook et al, 1989, Molecular Cloning: a laboratory manual.

Example 1

Detection of RA Associated Human Genetic Variations Using a DNA-Chip According to the Invention (Artchip)

1.1 Design of the DNA-Chip for Genotyping RA Associated Genetic Variations

A DNA-chip to detect human genetic variations associated with RA which permits simultaneous, sensitive, specific and reproducible detection was designed and manufactured. The said genetic variations are related to a greater or lesser risk of suffering from RA, a better or worse response to treatment and also a better or worse prognosis of the disease. Illustrative examples of human genetic variations associated with antigens connected to RA which can be determined using this DNA-chip are shown in Table 1A and 1B.

The DNA-chip designed and manufactured consists of a support (glass slide) which shows a plurality of probes on its surface that permits the detection of genetic variations previously mentioned. These probes are capable of hybridizing with the amplified sequences of the genes related to RA. The DNA sequences of each one of the probes used are listed in Table 2 (FIG. 2) In general, the name of the gene and the mutation is indicated (change of nucleotide, "ins": insertion "del" deletion or change of aminoacid) All of the listed probes have been technically validated.

The probes are listed below in probes sets, each set consisting of 4 or more probes. The listed probes correspond to SEQ ID NOS: 1-360 with consecutive probes given consecutive SEQ ID NOS. For example, the probes listed below the set for analysis of the C1672T polymorphism correspond to SEQ ID NOS: 1-4 respectively, with the first listed probe SEQ ID NO: 1 and the fourth listed probe in the set, SEQ ID NO: 4. Similarly, for example, the probes listed below in the set for analysis of the (VEGF) G1154A polymorphism correspond to SEQ ID NOS: 37-40, with the first listed probe SEQ ID NO: 37 and the fourth listed probe in the set SEQ ID NO: 40.

1.2 Production of the DNA-Chip

Printing and Processing of the Glass Slides

The probes capable of detecting the genetic variations previously identified are printed onto aminosilane coated supports (glass slides) using DMSO as a solvent. The printing is carried out using a spotter or printer of oligonucleotides (probes) while controlling the temperature and relative humidity.

The joining of the probes to the support (glass slides) is carried out by means of crosslinking with ultraviolet radiation and heating as described in the documentation provided by the manufacturer (for example, Corning Lifesciences http://www.corning.com). The relative humidity during the deposition process is maintained between 40-50% and the temperature around 20° C.

1.3 Validation of the Clinical Usefulness of the DNA-Chip 1.3.1 Preparation of the Sample to be Hybridized The DNA of the individual is extracted from a blood sample by a standard protocol of filtration. (For example, commercial kits from Macherey Nagel, Qiagene etc).

Target DNA regions containing the genetic variations of interest are amplified by multiplex PCR using appropriate pairs of oligonucleotide primers. Any suitable pair of oligonucleotides can be used which allow specific amplification of genetic fragments where a genetic variation to be detected might exist. Advantageously, those pairs of oligonucleotide primers which permit the said amplifications to be performed in the least possible number of PCR reactions are used.

The oligonucleotide primers used to PCR amplify target regions containing the genetic variations in FIG. 1 are listed in Table 3 (FIG. 3). These primers represent an additional aspect to the invention.

The PCR multiplex reactions are carried out simultaneously under the same conditions of time and temperature which permit specific amplification of the gene fragments in which the genetic variations to be detected might exist. Once the PCR multiplex has finished, agarose gel analysis is used to check that the amplification reaction has taken place.

Next, the sample to be hybridized (products of amplification) is subjected to fragmentation with a DNase and the resulting fragmentation products subjected to indirect labelling. A terminal transferase adds a nucleotide, covalently joined to one member of a pair of molecules that specifically bind to one another (e.g. biotin allowing subsequent specific binding to streptavidin) to the ends of these small DNA fragments.

Before applying the sample to the DNA-chip, the sample is denatured by heating to 95° C. for 5 minutes and then, the "ChipMap Kit Hybridization Buffer" (Ventana Medical System) is added.

1.3.2 Hybridization

Hybridization is carried out automatically in a hybridisation station such as the Ventana Discovery (Ventana Medical Systems) that has been specifically developed for such a use. Alternatively hybridisation can be performed manually.

The prehybridization and blocking of the slides is carried out with BSA. Next, the hybridization solution {ChipMap Kit Hybridization Buffer, Ventana Medical System) is applied to the surface of the DNA-chip which is maintained at 45° C. for 1 hour following the protocol of Ventana 9.0 Europe (Ventana Medical System). Finally the slides are subjected to different cleaning solutions (ChipMap hybridisation Kit Buffers, Ventana Medical System). Once the process of hybridization has finished, the final cleaning and drying of the slides begins.

When hybridization has taken place, the DNA chip is developed by incubation with a fluorescently labelled molecule that is able to specifically bind to the molecule incorporated into the amplification product by terminal transferase (e.g. in the case of biotin incorporation a fluorophore coupled to streptavidin such as streptavidin-Cy3 can be used) to label the probe positions where hybridization has occured.

1.3.3. Scanning the Slides

The slides are placed in a fluorescent confocal scanner, for example Axon 4100©, and the signal emitted by the fluorophore is scanned when stimulated by the laser.

1.3.4 Quantification of the Image

The scanner's own software allows quantification of the image obtained from the signal at the points where hybridization has taken place.

1.3.5 Interpretation of the Results

From the signal obtained with the probes which detect the different genetic variations, the genotype of the individual is established. In the first instance the scanner software executes a function to subtract the local background noise from the absolute signal intensity value obtained for each probe. Next, the replicates for each of the 4 probes that are used to characterize each genetic variation are grouped. The average intensity value for each of 4 probes is calculated using the average collated from the replicates in order to identify abnormal values (outliers) that can be excluded from further consideration. Once the average intensity value for each of the probes is known then two ratios are calculated (ratio 1 and ratio 2):

$$\text{Ratio } 1 = \frac{\text{Average intensity for probe 1}}{\text{Average intensity for probe 1 + Average intensity for probe 2}}$$

$$\text{Ratio } 2 = \frac{\text{Average intensity for probe 3}}{\text{Average intensity for probe 3 + Average intensity for probe 4}}$$

wherein probe 1 detects (is capable of specifically hybridising to) genetic variation A (e.g. a normal allele), probe 2 detects (is capable of specifically hybridising to) genetic variation B (e.g. a mutant allele), probe 3 detects (is capable of specifically hybridising to) genetic variation A (e.g. a normal allele) and probe 4 detects (is capable of specifically hybridising to) genetic variation B (e.g. a mutant allele).

These ratios are substituted in three linear functions which characterize each one of the three possible genotypes:
AA Function 1
AB Function 2
BB Function 3

The function which presents the highest absolute value determines the genotype of the patient.

In this case, the linear functions are obtained by analyzing 5 subjects for each of the three possible genotypes of the genetic variation (AA, AB, BB). With the results, ratios 1 and 2 are calculated for the 15 subjects. These ratios are classification variables for the three groups to create the linear functions, with which the discriminatory capacity of the two pairs of designed probes are evaluated. If the discriminatory capacity is not 100%, the probes are redesigned. New subjects characterized for each of the three genotypes make up new ratios 1 and 2 to perfect the linear functions and in short, to improve the discriminatory capacity of the algorithm based on these three functions.

When using a confocal fluorescent scanner, to obtain reliable results it is preferable that ratios 1 and 2 are within the range of the ratios used to build the groups, the average fluorescence intensity of the 4n (for example 40) replicates with regard to background noise is greater than 5 and the coefficient of variation of all of the DNA-chip replicates is below 0.25.

Again when a fluorescent confocal scanner is used in the experiment, for a complete hybridization to be considered reliable preferably the ratio of probe fluorescence intensity to background noise of all the DNA-chip probes is above 15. Likewise, the average of all the ratios is preferably above 0.6 and the negative control is preferably less than or equal to 3 times the background noise To sum up, in this case 4 probes (repeated 10 times) are presented on the slide for detection of each mutation. Two of the probes detect one genetic variation (A) and the other two the other genetic variation (B). The examined base is located in the central position of the probes.

A subject homozygous for the genetic variation A will not show genetic variation B. Consequently, in the image obtained from the glass support the probes which detect genetic variation B will show a hybridization signal significantly less than that shown by variation A and vice versa. In this case the ratios 1 and 2 will show 1 and the subjects will be assigned as homozygous AA by the software analysis.

On the other hand, a heterozygous subject for the determined genetic variation shows both the genetic variations. Therefore, the probes which detect them show an equivalent hybridization signal. The ratios 1 and 2 will show 0.5 and the subject will be assigned as heterozygous AB by the software analysis.

The oligonucleotide primers used to amplify (by means of PCR multiplex) target regions containing RA associated genetic variations in FIG. 1 are listed in Table 3. The said oligonucleotide primers represent an additional aspect to the present invention.

Oligonucleotide primers used for PCR amplifications are listed in Table 3. These correspond to SEQ ID NOS: 361-540, with primers numbered consecutively as they are listed.

Example 2

Establishing Models for Predicting RA Phenotypes

Methods
Study Design

Patients with RA fulfilling the 1987 ACR criteria were enrolled from five Rheumatology Departments of university hospitals in Spain: Hospital Puerta de Hierro (Madrid), Hospital Virgen de las Nieves (Granada), Hospital Clinic (Barcelona), Hospital La Paz (Madrid) and Hospital Juan Canalejo (A Coruña). In order to have a homogeneous therapeutical management, the patients included in the study had to be diagnosed and treated in a Rheumatology Service after 1 Jan. 1990, that is to say, the samples should have at least five years of follow-up. Complete inclusion criteria were the following: 1) patients disclosed according to American College of Rheumatology (ACR) criteria, 2) RA onset after 18 years old, 3) with radiological erosions. 4) caucasian, 5) more than 5 years of evolution and 6) diagnosed after the 1 Jan. 1990. A total of 375 individuals matching those criteria were included in the study.

Baseline clinical and analytical variables were recorded from every patient: onset age, number of involved joints, anti-cyclic citrullinated peptide, erythrocyte sedimentation rate, rheumatoid factor, C-reactive protein, gender, age and smoking status. The study adhered to the Helsinki Declaration (World Medical Association) and the EMEA (European Medicines Agency) recommendations.

Studied Phenotypes

After five years of follow-up the seven following outcomes were considered: 1) Aggressiveness; prediction of aggressive RA was analyzed by studying different sub-phenotypes: 1.1) Patients with Health Assessment Questionnaire (HAQ) greater than 2, wherein indicates RA causing important functional incapacity. 1.2) Patients showing multiple erosions in hands and feet. 1.3) Patients receiving more than three different treatments. 1.4) Patients whose disease obliged them to leave their jobs. 1.5) Patients receiving an articular prosthesis due to RA. 2) Therapy response; prediction of patients showing methotrexate intolerance. 3) Remission; defined as complete absence of joint symptoms without therapy, for at least 5 years. Every patient was classified as No/Yes (0/1) regarding those seven phenotypes.

Genotyping and Single Nucleotide Polymorphism (SNP) selection Peripheral blood (2 ml) was obtained from each patient, placed in an EDTA-treated tube. Plasma DNA was extracted with the QIAAMP® DNA Blood MiniKit (Qiagen) following the manufacturer's specifications. Genotyping was carried out using ARTchip DNA microarray. Several SNPs belonging to genes coding for protein involved in innate and adaptive immunity and metabolism of the bone and of the cartilage were genotyped for each patient. The SNP selection was based on previous published data, emerging pharmacological therapies and our own research expertise. The SNP selection in those genes was based on a minor allele frequency of 0.1. Only "TagSNPs" ($R^2<0.8$) were taken into account as this gave more statistical power by reducing the degrees of freedom (df) of our tests

```
Foward TAG
SEQ ID NO 544     GCTAGATGAAGAGCAAGCGC

Reverse TAG
SEQ ID NO 545     TACAACCGACAGATGTATGT
```

From all the SNPs genotyped, only one fraction was included in the stepwise logistic regression analysis to limit the overall false-positive rate. First of all, chi-squared ($\chi^2$) tests were performed in order to test the conformity with Hardy-Weinberg expectations (HWE) of the genetic polymorphisms under analysis. Only SNPs that agreed HWE law in both separate groups under analysis were included in this study. SNPs with extremely high deviations from the predictions of HWE (p values lower than 0.01) were excluded from the analysis as deviations could indicate problems such as genotyping errors. In addition, single locus association tests between SNP allele frequency (allelic associations) and patient phenotype were carried out using the standard contingency $\chi^2$ test, and p-values were determined, including Bonferroni correction for multiple testing. The possibility that deviations from HWE in our overall population (both phenotypes under analysis together) could be important in disease causation was also investigated by combining the effect of the allelic association and total HWE. The product of the HWE p-value and the allelic association p-value was used to rank the SNPs in order of importance. The ones with the smallest p-values were included in the regression analysis. All the genetic analyses were carried out using HelixTree® software (Golden Helix, Inc., Bozeman, Mont., USA).

Statistical Modelling

The statistical analysis was carried out between the patient groups (No-0/Yes-1) to attempt discrimination between both groups for each of the seven different studied phenotypes. Seven different models were evaluated: one model to distinguish between HAQ<2 and HAQ>2 (model 1); one model to distinguish patients with or without multiple erosions in hands and feet (model 2); one model to distinguish patients receiving equal or more than or less than three different treatments (model 3); one model to distinguish patients whose disease obliged them to leave their jobs (Yes or No) (model 4); one model to distinguish patients receiving an articular prosthesis due to RA (Yes or No) (model 5); one model to distinguish patients showing methotrexate intolerance (Yes or No) (model 6) and one model to distinguish patients achieving remission (Yes or No) (model 7).

Statistical analyses were performed using the Statistical Package for the Social Sciences (SPSS Inc. Headquarters, Chicago, Ill., USA) version 11.0. Multiple genotype-phenotype associations were analysed by means of multivariate logistic regression (Forward LR) with clinically determined disease phenotypes as dependent variables and the individual loci and clinical and analytical data as independent variables. The goodness of fit of the models was evaluated using Hosmer-Lemeshow statistics and their accuracy was assessed by calculating the area under the curve (AUC) of the Receiver Operating Characteristic curve (ROC) with 95% confidence intervals. The explained variability of the models on the basis of the SNPs was evaluated by means of the R2 Nagelkerke. To measure the impact of the SNPs and variables included in the models of the analysed phenotypes, the sensitivity, specificity, and positive likelihood ratio (LR+=sensitivity/(1−specificity)) were computed by means of ROC curves.

Results

To differentiate between HAQ>2 (model 1) 3 predictors (2 SNPs+1 clinical variable) entered into the forward LR model. For model 2 (Multiple erosions) 4 predictors SNPs+2 clinical variables entered in the model. For model 3 (3 or more treatments) 3 predictors SNPs+4 clinical variables entered in the model. For model 4 (leaving the job) only 3 predictors SNPs entered in the model. For model 5 (articular prosthesis) 4 predictors SNPs+2 clinical variable entered in the model. For model 6 (Methotrexate intolerance) 1 predictors SNPs+1 clinical variable entered in the model. Finally, for model 7 (achieving remission status) 2 predictors SNPs+1 clinical variable entered in the model. The SNP variables and clinical variables included on each model are listed in Table 11A (FIG. 11A).

Information regarding the variables (clinical and SNPs) remaining in each function is shown in. Tables 4 to 10. Regression probability functions are built using the Statistical Package for the Social Sciences (SPSS Inc. Headquarters, Chicago, Ill., USA) version 14.0. SPSSv14. B is the coefficient associated to each genotype in the probability function. ET is the error in the calculation of B. Wald is the statistical test. GL freedom degrees. Sig. P value of B for the Wald test. Exp (B) is Relative Risk.

The contribution of genetic and clinical factors to studied RA phenotypes can be further demonstrated by the substantial proportion of variance ($R^2$ Nagelkerke) explained by the functions (26.0% for model 1; 43.6% for model 2; 20.1% for model 3; 18.3% for model 4; 15.3% for model 5; 18.3% for model 6 and 26% for model 7). Probability functions and ROC curves were obtained for each phenotype analysed. ROC curves, sensitivity, specificity and positive likelihood ratios (LR+) of all the models are given in FIGS. 4 to 10.

Nagelkerke R2 is a way of measuring the proportion of variants explained by the function. The area under the ROC curve (ROC AUC) is a measure of test performance or diagnostic accuracy. The positive likelihood ratio (LR+) is calculated as sensititivty/1−specificity.

Discussion

Likelihood ratios are a useful and practical way of expressing the power of diagnostic tests. Four of the seven models described in this patent present a relatively high LR value, thus evidencing the capacity of the SNP combinations studied to predict that particular phenotype. The high ROC-AUCs obtained for these models provides further evidence for the high discriminatory power of the SNP combinations used. The usefulness of the ROC-AUC magnitude as a tool for evaluating the strength of the relationship between genotypes and disease has been described previously. Using these SNPs to obtain a genetic profile of the patient provides an extra tool for the physician to differentiate between patients with a different course of the disease, possibility of remission, presence of major erosion on the X-rays and number of treatment needed. For the remaining models we obtained a lower LR probably due to the fact that the studied phenotype is also dependent on environmental factors not calculated in our functions. However with these models, based mainly on genetics factors, physicians can reasonably consider the possibility of a surgical intervention, that a patient could leave its job and the possibility of a different therapy. The clinical symptoms, together with biochemical routine tests form part of the diagnosis of RA and are necessary for a correct therapeutic and prognostic orientation. The models described herein, based both on genetics and biochemical laboratory data, are suitable for use during the follow-up of RA patients and allow the identification of well defined patient subtypes, giving important indications on their future treatment.

The invention claimed is:

1. A method of prognosing a rheumatoid arthritis (RA) remission phenotype in a subject comprising:
genotyping a sample obtained from the subject at one or more positions of single nucleotide polymorphism selected from the remission SNPs in Table 12; and
determining that the subject has the RA remission phenotype if the genotype of the subject comprises one or more of the remission SNPs in Table 12, wherein the RA remission phenotype comprises at least 5 years of remission.

2. The method of claim 1, wherein said one or more SNPs include SNP 28 (rs2476601) or a SNP having $R^2 > 0.8$ with said SNP 28 (rs2476601).

3. The method of claim 2, wherein said one or more SNPs include SNP 28 (rs2476601).

4. The method of claim 2, wherein said method further comprises determining a binary representation of the level of anti-cyclic citrullinated peptide antibody (ANTI-PCC BI) in the serum of the subject.

5. The method of claim 1, wherein genotyping the sample obtained from the subject comprises microarray analysis or sequencing.

6. The method of claim 1, wherein said remission is complete absence of pain in the joints of said subject in the absence of therapy for at least 5 years.

7. The method of claim 1, wherein genotyping the sample obtained from the subject comprises genotyping a sample which has been obtained from blood, saliva, liver, kidney, pancreas, heart, urine or from cells from the buccal cavity of the subject.

8. The method of claim 7, wherein said blood comprises serum, lymphocytes, lymphoblastoid cells, fibroblasts, platelets, mononuclear cells or other blood cells.

9. The method of claim 1, wherein said method further comprises prognosing a further RA phenotype in the subject, wherein said method further comprises:
genotyping the sample obtained from the subject at one or more positions of single nucleotide polymorphism selected from the SNPs in Table 12, wherein:
(a) the RA phenotype is a health assessment questionnaire (HAQ) score of >2 (HAQ>2) and the one or more SNPs is selected from the HAQ>2 SNPs in Table 12;
(b) the RA phenotype is presence of multiple of erosions in the hands and feet (RX2) and the one or more SNPs is selected from the RX2 SNPs in Table 12;
(c) the RA phenotype is receiving 3 or more different treatments (TT0 30M) and the one or more SNPs is selected from the TT0 30M SNPs in Table 12;
(d) the RA phenotype is being forced to leave employment because of RA (leaving the job) and the one or more SNPs is selected from the "leaving the job" SNPs in Table 12;
(e) the RA phenotype is receiving an articular prosthesis (surgical intervention) and the one or more SNPs is selected from the "surgical intervention" SNPs in Table 12;
(f) the RA phenotype is methotrexate intolerance and the one or more SNPs is selected from the "methotrexate intolerance" SNPs in Table 12; or
(g) a combination of two or more of (a) through (f); and
determining that the subject has said further RA phenotype if the genotype of the subject comprises the one or more positions of single nucleotide polymorphism of (a) through (g).

10. A method of prognosing a rheumatoid arthritis (RA) remission phenotype in a subject comprising:
genotyping a sample obtained from the subject at one or more positions of single nucleotide polymorphism selected from the remission SNPs in Table 12; and
determining that the subject is likely to have the RA remission phenotype if the genotype of the subject comprises one or more of the remission SNPs in Table 12.

11. The method of claim 10, wherein the sample obtained from the subject has been obtained from blood, saliva, liver, kidney, pancreas, heart, urine or from cells from the buccal cavity of the subject.

12. The method of claim 10, wherein said one or more SNPs include SNP 28 (rs2476601) or a SNP having $R^2 > 0.8$ with said SNP 28 (rs2476601).

13. The method of claim 12, wherein said one or more SNPs include SNP 28 (rs2476601).

14. The method of claim 12, wherein said remission phenotype is at least 5 years of remission of RA in said subject.

15. The method of claim 14, wherein said remission is complete absence of pain in the joints of said subject in the absence of therapy for at least 5 years.

16. A method of prognosing a rheumatoid arthritis (RA) remission phenotype in a subject comprising:
genotyping a sample obtained from the subject at one or more positions of single nucleotide polymorphism selected from the remission SNPs in Table 12;
determining a binary representation of the level of anti-cyclic citrullinated peptide antibody (ANTI-PCC BI) in a serum sample from the subject; and
determining that the subject is likely to have the RA remission phenotype if the genotype of the subject comprises one or more of the remission SNPs in Table 12 and determining that the subject has the RA remission phenotype if the ANTI-PCC BI comprises the ANTI-PCC BI in Table 11A, wherein the remission phenotype comprises at least 5 years of remission.

17. The method of claim 15, wherein the sample obtained from the subject has been obtained from blood, saliva, liver, kidney, pancreas, heart, urine or from cells from the buccal cavity of the subject.

18. The method of claim 15, wherein said one or more SNPs include SNP 28 (rs2476601) or a SNP having $R^2>0.8$ with said SNP 28 (rs2476601).

19. The method of claim 18, wherein said one or more SNPs include SNP 28 (rs2476601).

20. The method of claim 18, wherein said remission is complete absence of pain in the joints of said subject in the absence of therapy for at least 5 years.

* * * * *

SEQUENCE LISTING

```
<160> NUMBER OF SEQ ID NOS: 545

<210> SEQ ID NO 1
<211> LENGTH: 25
<212> TYPE: DNA
<213> ORGANISM: Homo sapiens;

<400> SEQUENCE: 1 aaaaagggt gaggattcca atcag                                          25

<210> SEQ ID NO 2
<211> LENGTH: 25
<212> TYPE: DNA
<213> ORGANISM: Homo sapiens;

<400> SEQUENCE: 2 aaaaagggt gaagattcca atcag                                          25

<210> SEQ ID NO 3
<211> LENGTH: 23
<212> TYPE: DNA
<213> ORGANISM: Homo sapiens;

<400> SEQUENCE: 3
aaaaagggtg aggattccaa tca                                           23

<210> SEQ ID NO 4
<211> LENGTH: 23
<212> TYPE: DNA
<213> ORGANISM: Homo sapiens;

<400> SEQUENCE: 4
aaaaagggtg aagattccaa tca                                           23

<210> SEQ ID NO 5
<211> LENGTH: 23
<212> TYPE: DNA
<213> ORGANISM: Homo sapiens;

<400> SEQUENCE: 5
taagagctgt ccctggggca gat                                           23

<210> SEQ ID NO 6
<211> LENGTH: 23
<212> TYPE: DNA
<213> ORGANISM: Homo sapiens;

<400> SEQUENCE: 6
taagagctgt cgctggggca gat                                           23

<210> SEQ ID NO 7
<211> LENGTH: 23
<212> TYPE: DNA
<213> ORGANISM: Homo sapiens;

<400> SEQUENCE: 7
atctgcccca gggacagctc tta                                           23

<210> SEQ ID NO 8
<211> LENGTH: 23
```

-continued

```
<212> TYPE: DNA
<213> ORGANISM: Homo sapiens;

<400> SEQUENCE: 8
atctgcccca gcgacagctc tta                                              23

<210> SEQ ID NO 9
<211> LENGTH: 23
<212> TYPE: DNA
<213> ORGANISM: Homo sapiens;

<400> SEQUENCE: 9
cagaaatctc cctgtgcgca gac                                              23

<210> SEQ ID NO 10
<211> LENGTH: 23
<212> TYPE: DNA
<213> ORGANISM: Homo sapiens;

<400> SEQUENCE: 10
cagaaatctc cttgtgcgca gac                                              23

<210> SEQ ID NO 11
<211> LENGTH: 23
<212> TYPE: DNA
<213> ORGANISM: Homo sapiens;

<400> SEQUENCE: 11
gtctgcgcac agggagattt ctg                                              23

<210> SEQ ID NO 12
<211> LENGTH: 23
<212> TYPE: DNA
<213> ORGANISM: Homo sapiens;

<400> SEQUENCE: 12
gtctgcgcac aaggagattt ctg                                              23

<210> SEQ ID NO 13
<211> LENGTH: 23
<212> TYPE: DNA
<213> ORGANISM: Homo sapiens;

<400> SEQUENCE: 13
atattgccca cggccctcca gcc                                              23

<210> SEQ ID NO 14
<211> LENGTH: 23
<212> TYPE: DNA
<213> ORGANISM: Homo sapiens;

<400> SEQUENCE: 14
atattgccca cagccctcca gcc                                              23

<210> SEQ ID NO 15
<211> LENGTH: 23
<212> TYPE: DNA
<213> ORGANISM: Homo sapiens;

<400> SEQUENCE: 15
ggctggaggg ccgtgggcaa tat                                              23

<210> SEQ ID NO 16
<211> LENGTH: 23
```

<212> TYPE: DNA
<213> ORGANISM: Homo sapiens;

<400> SEQUENCE: 16
ggctggaggg ctgtgggcaa tat                                              23

<210> SEQ ID NO 17
<211> LENGTH: 23
<212> TYPE: DNA
<213> ORGANISM: Homo sapiens;

<400> SEQUENCE: 17
gacgatgaaa gtggccagtg gta                                              23

<210> SEQ ID NO 18
<211> LENGTH: 23
<212> TYPE: DNA
<213> ORGANISM: Homo sapiens;

<400> SEQUENCE: 18
gacgatgaaa gcggccagtg gta                                              23

<210> SEQ ID NO 19
<211> LENGTH: 23
<212> TYPE: DNA
<213> ORGANISM: Homo sapiens;

<400> SEQUENCE: 19
taccactggc cactttcatc gtc                                              23

<210> SEQ ID NO 20
<211> LENGTH: 23
<212> TYPE: DNA
<213> ORGANISM: Homo sapiens;

<400> SEQUENCE: 20
taccactggc cgctttcatc gtc                                              23

<210> SEQ ID NO 21
<211> LENGTH: 23
<212> TYPE: DNA
<213> ORGANISM: Homo sapiens;

<400> SEQUENCE: 21
ctacctcacc gcggtgggta agt                                              23

<210> SEQ ID NO 22
<211> LENGTH: 23
<212> TYPE: DNA
<213> ORGANISM: Homo sapiens;

<400> SEQUENCE: 22
ctacctcacc ggggtgggta agt                                              23

<210> SEQ ID NO 23
<211> LENGTH: 23
<212> TYPE: DNA
<213> ORGANISM: Homo sapiens;

<400> SEQUENCE: 23
acttacccac cgcggtgagg tag                                              23

<210> SEQ ID NO 24
<211> LENGTH: 23

```
<212> TYPE: DNA
<213> ORGANISM: Homo sapiens;

<400> SEQUENCE: 24
acttacccac cccggtgagg tag                                              23

<210> SEQ ID NO 25
<211> LENGTH: 23
<212> TYPE: DNA
<213> ORGANISM: Homo sapiens;

<400> SEQUENCE: 25
agcgggagca gagggacgtt tcc                                              23

<210> SEQ ID NO 26
<211> LENGTH: 23
<212> TYPE: DNA
<213> ORGANISM: Homo sapiens;

<400> SEQUENCE: 26
agcgggagca ggggacgtt tcc                                               23

<210> SEQ ID NO 27
<211> LENGTH: 23
<212> TYPE: DNA
<213> ORGANISM: Homo sapiens;

<400> SEQUENCE: 27
ggaaacgtcc ctctgctccc gct                                              23

<210> SEQ ID NO 28
<211> LENGTH: 23
<212> TYPE: DNA
<213> ORGANISM: Homo sapiens;

<400> SEQUENCE: 28
ggaaacgtcc ccctgctccc gct                                              23

<210> SEQ ID NO 29
<211> LENGTH: 23
<212> TYPE: DNA
<213> ORGANISM: Homo sapiens;

<400> SEQUENCE: 29
gccctgcctg tgtagccctt tgg                                              23

<210> SEQ ID NO 30
<211> LENGTH: 23
<212> TYPE: DNA
<213> ORGANISM: Homo sapiens;

<400> SEQUENCE: 30
gccctgcctg tttagccctt tgg                                              23

<210> SEQ ID NO 31
<211> LENGTH: 23
<212> TYPE: DNA
<213> ORGANISM: Homo sapiens;

<400> SEQUENCE: 31
ccaaagggct acacaggcag ggc                                              23

<210> SEQ ID NO 32
<211> LENGTH: 23
```

```
<212> TYPE: DNA
<213> ORGANISM: Homo sapiens;

<400> SEQUENCE: 32
ccaaagggct aaacaggcag ggc                                      23

<210> SEQ ID NO 33
<211> LENGTH: 23
<212> TYPE: DNA
<213> ORGANISM: Homo sapiens;

<400> SEQUENCE: 33
cacacagaca aatcagttct tga                                      23

<210> SEQ ID NO 34
<211> LENGTH: 23
<212> TYPE: DNA
<213> ORGANISM: Homo sapiens;

<400> SEQUENCE: 34
cacacagaca actcagttct tga                                      23

<210> SEQ ID NO 35
<211> LENGTH: 23
<212> TYPE: DNA
<213> ORGANISM: Homo sapiens;

<400> SEQUENCE: 35
tcaagaactg atttgtctgt gtg                                      23

<210> SEQ ID NO 36
<211> LENGTH: 23
<212> TYPE: DNA
<213> ORGANISM: Homo sapiens;

<400> SEQUENCE: 36
tcaagaactg agttgtctgt gtg                                      23

<210> SEQ ID NO 37
<211> LENGTH: 23
<212> TYPE: DNA
<213> ORGANISM: Homo sapiens;

<400> SEQUENCE: 37
ccgcgtgtgg aggggctgag gct                                      23

<210> SEQ ID NO 38
<211> LENGTH: 23
<212> TYPE: DNA
<213> ORGANISM: Homo sapiens;

<400> SEQUENCE: 38
agcctcagcc cctccacacg cgg                                      23

<210> SEQ ID NO 39
<211> LENGTH: 23
<212> TYPE: DNA
<213> ORGANISM: Homo sapiens;

<400> SEQUENCE: 39
ccgcgtgtgg aagggctgag gct                                      23

<210> SEQ ID NO 40
<211> LENGTH: 23
```

```
<212> TYPE: DNA
<213> ORGANISM: Homo sapiens;

<400> SEQUENCE: 40
agcctcagcc cctccacacg cgg                                              23

<210> SEQ ID NO 41
<211> LENGTH: 23
<212> TYPE: DNA
<213> ORGANISM: Homo sapiens;

<400> SEQUENCE: 41
agcagcgaaa gggacagggg caa                                              23

<210> SEQ ID NO 42
<211> LENGTH: 23
<212> TYPE: DNA
<213> ORGANISM: Homo sapiens;

<400> SEQUENCE: 42
agcagcgaaa gcgacagggg caa                                              23

<210> SEQ ID NO 43
<211> LENGTH: 23
<212> TYPE: DNA
<213> ORGANISM: Homo sapiens;

<400> SEQUENCE: 43
ttgcccctgt ccctttcgct gct                                              23

<210> SEQ ID NO 44
<211> LENGTH: 23
<212> TYPE: DNA
<213> ORGANISM: Homo sapiens;

<400> SEQUENCE: 44
ttgcccctgt cgctttcgct gct                                              23

<210> SEQ ID NO 45
<211> LENGTH: 23
<212> TYPE: DNA
<213> ORGANISM: Homo sapiens;

<400> SEQUENCE: 45
gtgacccagc acggtccctc ttg                                              23

<210> SEQ ID NO 46
<211> LENGTH: 23
<212> TYPE: DNA
<213> ORGANISM: Homo sapiens;

<400> SEQUENCE: 46
gtgacccagc atggtccctc ttg                                              23

<210> SEQ ID NO 47
<211> LENGTH: 23
<212> TYPE: DNA
<213> ORGANISM: Homo sapiens;

<400> SEQUENCE: 47
caagagggac cgtgctgggt cac                                              23

<210> SEQ ID NO 48
<211> LENGTH: 23
```

```
<212> TYPE: DNA
<213> ORGANISM: Homo sapiens;

<400> SEQUENCE: 48
caagagggac catgctgggt cac                                     23

<210> SEQ ID NO 49
<211> LENGTH: 23
<212> TYPE: DNA
<213> ORGANISM: Homo sapiens;

<400> SEQUENCE: 49
aaaaattatt acataaaatt cta                                     23

<210> SEQ ID NO 50
<211> LENGTH: 23
<212> TYPE: DNA
<213> ORGANISM: Homo sapiens;

<400> SEQUENCE: 50
aaaaattatt aaataaaatt cta                                     23

<210> SEQ ID NO 51
<211> LENGTH: 23
<212> TYPE: DNA
<213> ORGANISM: Homo sapiens;

<400> SEQUENCE: 51
tagaatttta tgtaataatt ttt                                     23

<210> SEQ ID NO 52
<211> LENGTH: 23
<212> TYPE: DNA
<213> ORGANISM: Homo sapiens;

<400> SEQUENCE: 52
tagaatttta tttaataatt ttt                                     23

<210> SEQ ID NO 53
<211> LENGTH: 23
<212> TYPE: DNA
<213> ORGANISM: Homo sapiens;

<400> SEQUENCE: 53
acggaagaaa acatttcatg aaa                                     23

<210> SEQ ID NO 54
<211> LENGTH: 23
<212> TYPE: DNA
<213> ORGANISM: Homo sapiens;

<400> SEQUENCE: 54
acggaagaaa agatttcatg aaa                                     23

<210> SEQ ID NO 55
<211> LENGTH: 23
<212> TYPE: DNA
<213> ORGANISM: Homo sapiens;

<400> SEQUENCE: 55
tttcatgaaa tgttttcttc cgt                                     23

<210> SEQ ID NO 56
<211> LENGTH: 23
```

```
<212> TYPE: DNA
<213> ORGANISM: Homo sapiens;

<400> SEQUENCE: 56
tttcatgaaa tcttttcttc cgt                                               23

<210> SEQ ID NO 57
<211> LENGTH: 23
<212> TYPE: DNA
<213> ORGANISM: Homo sapiens;

<400> SEQUENCE: 57
cagtggctat cgggagtttg tac                                               23

<210> SEQ ID NO 58
<211> LENGTH: 23
<212> TYPE: DNA
<213> ORGANISM: Homo sapiens;

<400> SEQUENCE: 58
cagtggctat caggagtttg tac                                               23

<210> SEQ ID NO 59
<211> LENGTH: 23
<212> TYPE: DNA
<213> ORGANISM: Homo sapiens;

<400> SEQUENCE: 59
gtacaaactc ccgatagcca ctg                                               23

<210> SEQ ID NO 60
<211> LENGTH: 23
<212> TYPE: DNA
<213> ORGANISM: Homo sapiens;

<400> SEQUENCE: 60
gtacaaactc ctgatagcca ctg                                               23

<210> SEQ ID NO 61
<211> LENGTH: 25
<212> TYPE: DNA
<213> ORGANISM: Homo sapiens;

<400> SEQUENCE: 61
ccaactagtt gctggatact tgcaa                                             25

<210> SEQ ID NO 62
<211> LENGTH: 25
<212> TYPE: DNA
<213> ORGANISM: Homo sapiens;

<400> SEQUENCE: 62
ccaactagtt gccggatact tgcaa                                             25

<210> SEQ ID NO 63
<211> LENGTH: 23
<212> TYPE: DNA
<213> ORGANISM: Homo sapiens;

<400> SEQUENCE: 63
caactagttg ctggatactt gca                                               23

<210> SEQ ID NO 64
<211> LENGTH: 23
```

```
<212> TYPE: DNA
<213> ORGANISM: Homo sapiens;

<400> SEQUENCE: 64
caactagttg ccggatactt gca                                          23

<210> SEQ ID NO 65
<211> LENGTH: 21
<212> TYPE: DNA
<213> ORGANISM: Homo sapiens;

<400> SEQUENCE: 65
gccaggaaag ccaatgtatg t                                            21

<210> SEQ ID NO 66
<211> LENGTH: 21
<212> TYPE: DNA
<213> ORGANISM: Homo sapiens;

<400> SEQUENCE: 66
gccaggaaag tcaatgtatg t                                            21

<210> SEQ ID NO 67
<211> LENGTH: 21
<212> TYPE: DNA
<213> ORGANISM: Homo sapiens;

<400> SEQUENCE: 67
gccaggaaag ccaatgtatg t                                            21

<210> SEQ ID NO 68
<211> LENGTH: 21
<212> TYPE: DNA
<213> ORGANISM: Homo sapiens;

<400> SEQUENCE: 68
gccaggaaag tcaatgtatg t                                            21

<210> SEQ ID NO 69
<211> LENGTH: 23
<212> TYPE: DNA
<213> ORGANISM: Homo sapiens;

<400> SEQUENCE: 69
aggggctcag ccgacggccc tcg                                          23

<210> SEQ ID NO 70
<211> LENGTH: 23
<212> TYPE: DNA
<213> ORGANISM: Homo sapiens;

<400> SEQUENCE: 70
aggggctcag ctgacggccc tcg                                          23

<210> SEQ ID NO 71
<211> LENGTH: 23
<212> TYPE: DNA
<213> ORGANISM: Homo sapiens;

<400> SEQUENCE: 71
cgagggccgt cggctgagcc cct                                          23

<210> SEQ ID NO 72
<211> LENGTH: 23
```

```
<212> TYPE: DNA
<213> ORGANISM: Homo sapiens;

<400> SEQUENCE: 72
cgagggccgt cagctgagcc cct                                    23

<210> SEQ ID NO 73
<211> LENGTH: 25
<212> TYPE: DNA
<213> ORGANISM: Homo sapiens;

<400> SEQUENCE: 73
aagtcaataa tatcatcgag gtagt                                  25

<210> SEQ ID NO 74
<211> LENGTH: 25
<212> TYPE: DNA
<213> ORGANISM: Homo sapiens;

<400> SEQUENCE: 74
aagtcaataa taccatcgag gtagt                                  25

<210> SEQ ID NO 75
<211> LENGTH: 23
<212> TYPE: DNA
<213> ORGANISM: Homo sapiens;

<400> SEQUENCE: 75
agtcaataat atcatcgagg tag                                    23

<210> SEQ ID NO 76
<211> LENGTH: 23
<212> TYPE: DNA
<213> ORGANISM: Homo sapiens;

<400> SEQUENCE: 76
agtcaataat accatcgagg tag                                    23

<210> SEQ ID NO 77
<211> LENGTH: 23
<212> TYPE: DNA
<213> ORGANISM: Homo sapiens;

<400> SEQUENCE: 77
gacaggcctg cgcattccca ata                                    23

<210> SEQ ID NO 78
<211> LENGTH: 23
<212> TYPE: DNA
<213> ORGANISM: Homo sapiens;

<400> SEQUENCE: 78
gacaggcctg cacattccca ata                                    23

<210> SEQ ID NO 79
<211> LENGTH: 23
<212> TYPE: DNA
<213> ORGANISM: Homo sapiens;

<400> SEQUENCE: 79
tattgggaat gcgcaggcct gtc                                    23

<210> SEQ ID NO 80
<211> LENGTH: 23
```

```
<212> TYPE: DNA
<213> ORGANISM: Homo sapiens;

<400> SEQUENCE: 80
tattgggaat gtgcaggcct gtc                                              23

<210> SEQ ID NO 81
<211> LENGTH: 23
<212> TYPE: DNA
<213> ORGANISM: Homo sapiens;

<400> SEQUENCE: 81
ctgggagttg cgatggtctg taa                                              23

<210> SEQ ID NO 82
<211> LENGTH: 23
<212> TYPE: DNA
<213> ORGANISM: Homo sapiens;

<400> SEQUENCE: 82
ctgggagttg ctatggtctg taa                                              23

<210> SEQ ID NO 83
<211> LENGTH: 23
<212> TYPE: DNA
<213> ORGANISM: Homo sapiens;

<400> SEQUENCE: 83
ttacagacca tcgcaactcc cag                                              23

<210> SEQ ID NO 84
<211> LENGTH: 23
<212> TYPE: DNA
<213> ORGANISM: Homo sapiens;

<400> SEQUENCE: 84
ttacagacca tagcaactcc cag                                              23

<210> SEQ ID NO 85
<211> LENGTH: 23
<212> TYPE: DNA
<213> ORGANISM: Homo sapiens;

<400> SEQUENCE: 85
tgcaccgact ctgcagagag act                                              23

<210> SEQ ID NO 86
<211> LENGTH: 23
<212> TYPE: DNA
<213> ORGANISM: Homo sapiens;

<400> SEQUENCE: 86
tgcaccgact cggcagagag act                                              23

<210> SEQ ID NO 87
<211> LENGTH: 23
<212> TYPE: DNA
<213> ORGANISM: Homo sapiens;

<400> SEQUENCE: 87
agtctctctg cagagtcggt gca                                              23

<210> SEQ ID NO 88
<211> LENGTH: 23
```

<212> TYPE: DNA
<213> ORGANISM: Homo sapiens;

<400> SEQUENCE: 88
agtctctctg ccgagtcggt gca                                    23

<210> SEQ ID NO 89
<211> LENGTH: 23
<212> TYPE: DNA
<213> ORGANISM: Homo sapiens;

<400> SEQUENCE: 89
acccaccagg gcgaacgaca ata                                    23

<210> SEQ ID NO 90
<211> LENGTH: 23
<212> TYPE: DNA
<213> ORGANISM: Homo sapiens;

<400> SEQUENCE: 90
acccaccagg gtgaacgaca ata                                    23

<210> SEQ ID NO 91
<211> LENGTH: 23
<212> TYPE: DNA
<213> ORGANISM: Homo sapiens;

<400> SEQUENCE: 91
tattgtcgtt cgccctggtg ggt                                    23

<210> SEQ ID NO 92
<211> LENGTH: 23
<212> TYPE: DNA
<213> ORGANISM: Homo sapiens;

<400> SEQUENCE: 92
tattgtcgtt caccctggtg ggt                                    23

<210> SEQ ID NO 93
<211> LENGTH: 23
<212> TYPE: DNA
<213> ORGANISM: Homo sapiens;

<400> SEQUENCE: 93
tgaacctggc tgccaggacc tgg                                    23

<210> SEQ ID NO 94
<211> LENGTH: 23
<212> TYPE: DNA
<213> ORGANISM: Homo sapiens;

<400> SEQUENCE: 94
tgaacctggc taccaggacc tgg                                    23

<210> SEQ ID NO 95
<211> LENGTH: 23
<212> TYPE: DNA
<213> ORGANISM: Homo sapiens;

<400> SEQUENCE: 95
ccaggtcctg gcagccaggt tca                                    23

<210> SEQ ID NO 96
<211> LENGTH: 23

```
<212> TYPE: DNA
<213> ORGANISM: Homo sapiens;

<400> SEQUENCE: 96
ccaggtcctg gtagccaggt tca                                      23

<210> SEQ ID NO 97
<211> LENGTH: 23
<212> TYPE: DNA
<213> ORGANISM: Homo sapiens;

<400> SEQUENCE: 97
ggaacaacat tgcttatggg ctg                                      23

<210> SEQ ID NO 98
<211> LENGTH: 23
<212> TYPE: DNA
<213> ORGANISM: Homo sapiens;

<400> SEQUENCE: 98
cagcccataa gcaatgttgt tcc                                      23

<210> SEQ ID NO 99
<211> LENGTH: 23
<212> TYPE: DNA
<213> ORGANISM: Homo sapiens;

<400> SEQUENCE: 99
ggaacaacat tacttatggg ctg                                      23

<210> SEQ ID NO 100
<211> LENGTH: 23
<212> TYPE: DNA
<213> ORGANISM: Homo sapiens;

<400> SEQUENCE: 100
cagcccataa gtaatgttgt tcc                                      23

<210> SEQ ID NO 101
<211> LENGTH: 23
<212> TYPE: DNA
<213> ORGANISM: Homo sapiens;

<400> SEQUENCE: 101
agcagagacg caggtggagg acg                                      23

<210> SEQ ID NO 102
<211> LENGTH: 23
<212> TYPE: DNA
<213> ORGANISM: Homo sapiens;

<400> SEQUENCE: 102
agcagagacg ctggtggagg acg                                      23

<210> SEQ ID NO 103
<211> LENGTH: 23
<212> TYPE: DNA
<213> ORGANISM: Homo sapiens;

<400> SEQUENCE: 103
cgtcctccac ctgcgtctct gct                                      23

<210> SEQ ID NO 104
<211> LENGTH: 23
```

<212> TYPE: DNA
<213> ORGANISM: Homo sapiens;

<400> SEQUENCE: 104
cgtcctccac cagcgtctct gct                                              23

<210> SEQ ID NO 105
<211> LENGTH: 23
<212> TYPE: DNA
<213> ORGANISM: Homo sapiens;

<400> SEQUENCE: 105
aggcgggggc ccgcgcttcc cgg                                              23

<210> SEQ ID NO 106
<211> LENGTH: 23
<212> TYPE: DNA
<213> ORGANISM: Homo sapiens;

<400> SEQUENCE: 106
aggcgggggc ctgcgcttcc cgg                                              23

<210> SEQ ID NO 107
<211> LENGTH: 23
<212> TYPE: DNA
<213> ORGANISM: Homo sapiens;

<400> SEQUENCE: 107
ccgggaagcg cgggcccccg cct                                              23

<210> SEQ ID NO 108
<211> LENGTH: 23
<212> TYPE: DNA
<213> ORGANISM: Homo sapiens;

<400> SEQUENCE: 108
ccgggaagcg caggcccccg cct                                              23

<210> SEQ ID NO 109
<211> LENGTH: 23
<212> TYPE: DNA
<213> ORGANISM: Homo sapiens;

<400> SEQUENCE: 109
cacttcctgt acggacacct gaa                                              23

<210> SEQ ID NO 110
<211> LENGTH: 23
<212> TYPE: DNA
<213> ORGANISM: Homo sapiens;

<400> SEQUENCE: 110
cacttcctgt atggacacct gaa                                              23

<210> SEQ ID NO 111
<211> LENGTH: 23
<212> TYPE: DNA
<213> ORGANISM: Homo sapiens;

<400> SEQUENCE: 111
ttcaggtgtc cgtacaggaa gtg                                              23

<210> SEQ ID NO 112
<211> LENGTH: 23

```
<212> TYPE: DNA
<213> ORGANISM: Homo sapiens;

<400> SEQUENCE: 112
ttcaggtgtc catacaggaa gtg                                              23

<210> SEQ ID NO 113
<211> LENGTH: 23
<212> TYPE: DNA
<213> ORGANISM: Homo sapiens;

<400> SEQUENCE: 113
tcttacaggg atggaggcaa tgg                                              23

<210> SEQ ID NO 114
<211> LENGTH: 23
<212> TYPE: DNA
<213> ORGANISM: Homo sapiens;

<400> SEQUENCE: 114
tcttacaggg acggaggcaa tgg                                              23

<210> SEQ ID NO 115
<211> LENGTH: 23
<212> TYPE: DNA
<213> ORGANISM: Homo sapiens;

<400> SEQUENCE: 115
ccattgcctc catccctgta aga                                              23

<210> SEQ ID NO 116
<211> LENGTH: 23
<212> TYPE: DNA
<213> ORGANISM: Homo sapiens;

<400> SEQUENCE: 116
ccattgcctc cgtccctgta aga                                              23

<210> SEQ ID NO 117
<211> LENGTH: 23
<212> TYPE: DNA
<213> ORGANISM: Homo sapiens;

<400> SEQUENCE: 117
gaaccagaga cgggccagag cat                                              23

<210> SEQ ID NO 118
<211> LENGTH: 23
<212> TYPE: DNA
<213> ORGANISM: Homo sapiens;

<400> SEQUENCE: 118
gaaccagaga caggccagag cat                                              23

<210> SEQ ID NO 119
<211> LENGTH: 23
<212> TYPE: DNA
<213> ORGANISM: Homo sapiens;

<400> SEQUENCE: 119
atgctctggc ccgtctctgg ttc                                              23

<210> SEQ ID NO 120
<211> LENGTH: 23
```

```
<212> TYPE: DNA
<213> ORGANISM: Homo sapiens;

<400> SEQUENCE: 120
atgctctggc ctgtctctgg ttc                                      23

<210> SEQ ID NO 121
<211> LENGTH: 23
<212> TYPE: DNA
<213> ORGANISM: Homo sapiens;

<400> SEQUENCE: 121
acatggtttt ttccccccat caa                                      23

<210> SEQ ID NO 122
<211> LENGTH: 23
<212> TYPE: DNA
<213> ORGANISM: Homo sapiens;

<400> SEQUENCE: 122
acatggtttt tccccccatc aaa                                      23

<210> SEQ ID NO 123
<211> LENGTH: 23
<212> TYPE: DNA
<213> ORGANISM: Homo sapiens;

<400> SEQUENCE: 123
ttgatggggg gaaaaaacca tgt                                      23

<210> SEQ ID NO 124
<211> LENGTH: 23
<212> TYPE: DNA
<213> ORGANISM: Homo sapiens;

<400> SEQUENCE: 124
ttgatggggg ggaaaaacca tgt                                      23

<210> SEQ ID NO 125
<211> LENGTH: 23
<212> TYPE: DNA
<213> ORGANISM: Homo sapiens;

<400> SEQUENCE: 125
caggggccac gcggggagca gcc                                      23

<210> SEQ ID NO 126
<211> LENGTH: 23
<212> TYPE: DNA
<213> ORGANISM: Homo sapiens;

<400> SEQUENCE: 126
caggggccac gggggagca gcc                                       23

<210> SEQ ID NO 127
<211> LENGTH: 23
<212> TYPE: DNA
<213> ORGANISM: Homo sapiens;

<400> SEQUENCE: 127
ggctgctccc cgcgtggccc ctg                                      23

<210> SEQ ID NO 128
<211> LENGTH: 23
```

```
<212> TYPE: DNA
<213> ORGANISM: Homo sapiens;

<400> SEQUENCE: 128
ggctgctccc cccgtggccc ctg                                            23

<210> SEQ ID NO 129
<211> LENGTH: 23
<212> TYPE: DNA
<213> ORGANISM: Homo sapiens;

<400> SEQUENCE: 129
accttatgat ctgcccgcct tgg                                            23

<210> SEQ ID NO 130
<211> LENGTH: 23
<212> TYPE: DNA
<213> ORGANISM: Homo sapiens;

<400> SEQUENCE: 130
accttatgat ccgcccgcct tgg                                            23

<210> SEQ ID NO 131
<211> LENGTH: 23
<212> TYPE: DNA
<213> ORGANISM: Homo sapiens;

<400> SEQUENCE: 131
ccaaggcggg cagatcataa ggt                                            23

<210> SEQ ID NO 132
<211> LENGTH: 23
<212> TYPE: DNA
<213> ORGANISM: Homo sapiens;

<400> SEQUENCE: 132
ccaaggcggg cggatcataa ggt                                            23

<210> SEQ ID NO 133
<211> LENGTH: 19
<212> TYPE: DNA
<213> ORGANISM: Homo sapiens;

<400> SEQUENCE: 133
accccgtccc catgcccct                                                 19

<210> SEQ ID NO 134
<211> LENGTH: 19
<212> TYPE: DNA
<213> ORGANISM: Homo sapiens;

<400> SEQUENCE: 134
accccgtcct catgcccct                                                 19

<210> SEQ ID NO 135
<211> LENGTH: 19
<212> TYPE: DNA
<213> ORGANISM: Homo sapiens;

<400> SEQUENCE: 135
accccgtccc catgcccct                                                 19

<210> SEQ ID NO 136
<211> LENGTH: 19
```

<212> TYPE: DNA
<213> ORGANISM: Homo sapiens;

<400> SEQUENCE: 136
accccgtcct catgcccct                                              19

<210> SEQ ID NO 137
<211> LENGTH: 23
<212> TYPE: DNA
<213> ORGANISM: Homo sapiens;

<400> SEQUENCE: 137
gagaaaaaaa catggagaaa gac                                         23

<210> SEQ ID NO 138
<211> LENGTH: 23
<212> TYPE: DNA
<213> ORGANISM: Homo sapiens;

<400> SEQUENCE: 138
gagaaaaaaa cgtggagaaa gac                                         23

<210> SEQ ID NO 139
<211> LENGTH: 19
<212> TYPE: DNA
<213> ORGANISM: Homo sapiens;

<400> SEQUENCE: 139
aggtcctggc agccaggtt                                              19

<210> SEQ ID NO 140
<211> LENGTH: 19
<212> TYPE: DNA
<213> ORGANISM: Homo sapiens;

<400> SEQUENCE: 140
aggtcctggt agccaggtt                                              19

<210> SEQ ID NO 141
<211> LENGTH: 23
<212> TYPE: DNA
<213> ORGANISM: Homo sapiens;

<400> SEQUENCE: 141
gaaccagaga cgggccagag cat                                         23

<210> SEQ ID NO 142
<211> LENGTH: 23
<212> TYPE: DNA
<213> ORGANISM: Homo sapiens;

<400> SEQUENCE: 142
gaaccagaga caggccagag cat                                         23

<210> SEQ ID NO 143
<211> LENGTH: 23
<212> TYPE: DNA
<213> ORGANISM: Homo sapiens;

<400> SEQUENCE: 143
atgctctggc ccgtctctgg ttc                                         23

<210> SEQ ID NO 144
<211> LENGTH: 23

```
<212> TYPE: DNA
<213> ORGANISM: Homo sapiens;

<400> SEQUENCE: 144
atgctctggc ctgtctctgg ttc                                      23

<210> SEQ ID NO 145
<211> LENGTH: 21
<212> TYPE: DNA
<213> ORGANISM: Homo sapiens;

<400> SEQUENCE: 145
ctccctgctc cgattccgag g                                        21

<210> SEQ ID NO 146
<211> LENGTH: 21
<212> TYPE: DNA
<213> ORGANISM: Homo sapiens;

<400> SEQUENCE: 146
ctccctgctc tgattccgag g                                        21

<210> SEQ ID NO 147
<211> LENGTH: 19
<212> TYPE: DNA
<213> ORGANISM: Homo sapiens;

<400> SEQUENCE: 147
tccctgctcc gattccgag                                           19

<210> SEQ ID NO 148
<211> LENGTH: 19
<212> TYPE: DNA
<213> ORGANISM: Homo sapiens;

<400> SEQUENCE: 148
tccctgctct gattccgag                                           19

<210> SEQ ID NO 149
<211> LENGTH: 23
<212> TYPE: DNA
<213> ORGANISM: Homo sapiens;

<400> SEQUENCE: 149
gaatgcaagc atggatgcag tct                                      23

<210> SEQ ID NO 150
<211> LENGTH: 23
<212> TYPE: DNA
<213> ORGANISM: Homo sapiens;

<400> SEQUENCE: 150
gaatgcaagc agggatgcag tct                                      23

<210> SEQ ID NO 151
<211> LENGTH: 21
<212> TYPE: DNA
<213> ORGANISM: Homo sapiens;

<400> SEQUENCE: 151
gactgcatcc atgcttgcat t                                        21

<210> SEQ ID NO 152
<211> LENGTH: 21
```

```
<212> TYPE: DNA
<213> ORGANISM: Homo sapiens;

<400> SEQUENCE: 152
gactgcatcc ctgcttgcat t                                              21

<210> SEQ ID NO 153
<211> LENGTH: 23
<212> TYPE: DNA
<213> ORGANISM: Homo sapiens;

<400> SEQUENCE: 153
ctgctgctgc cgctggtgag acc                                            23

<210> SEQ ID NO 154
<211> LENGTH: 23
<212> TYPE: DNA
<213> ORGANISM: Homo sapiens;

<400> SEQUENCE: 154
ctgctgctgc cactggtgag acc                                            23

<210> SEQ ID NO 155
<211> LENGTH: 23
<212> TYPE: DNA
<213> ORGANISM: Homo sapiens;

<400> SEQUENCE: 155
ggtctcacca gcggcagcag cag                                            23

<210> SEQ ID NO 156
<211> LENGTH: 23
<212> TYPE: DNA
<213> ORGANISM: Homo sapiens;

<400> SEQUENCE: 156
ggtctcacca gtggcagcag cag                                            23

<210> SEQ ID NO 157
<211> LENGTH: 23
<212> TYPE: DNA
<213> ORGANISM: Homo sapiens;

<400> SEQUENCE: 157
ttgattttaa tggccccttt tga                                            23

<210> SEQ ID NO 158
<211> LENGTH: 23
<212> TYPE: DNA
<213> ORGANISM: Homo sapiens;

<400> SEQUENCE: 158
ttgattttaa tagccccttt tga                                            23

<210> SEQ ID NO 159
<211> LENGTH: 23
<212> TYPE: DNA
<213> ORGANISM: Homo sapiens;

<400> SEQUENCE: 159
tcaaaagggg ccattaaaat caa                                            23

<210> SEQ ID NO 160
<211> LENGTH: 23
```

<210> SEQ ID NO 160
<211> LENGTH: 23
<212> TYPE: DNA
<213> ORGANISM: Homo sapiens;

<400> SEQUENCE: 160
tcaaaggggg ctattaaaat caa                                              23

<210> SEQ ID NO 161
<211> LENGTH: 23
<212> TYPE: DNA
<213> ORGANISM: Homo sapiens;

<400> SEQUENCE: 161
acacattctt ggccttctgc aga                                              23

<210> SEQ ID NO 162
<211> LENGTH: 23
<212> TYPE: DNA
<213> ORGANISM: Homo sapiens;

<400> SEQUENCE: 162
acacattctt gaccttctgc aga                                              23

<210> SEQ ID NO 163
<211> LENGTH: 23
<212> TYPE: DNA
<213> ORGANISM: Homo sapiens;

<400> SEQUENCE: 163
tctgcagaag gccaagaatg tgt                                              23

<210> SEQ ID NO 164
<211> LENGTH: 23
<212> TYPE: DNA
<213> ORGANISM: Homo sapiens;

<400> SEQUENCE: 164
tctgcagaag gtcaagaatg tgt                                              23

<210> SEQ ID NO 165
<211> LENGTH: 23
<212> TYPE: DNA
<213> ORGANISM: Homo sapiens;

<400> SEQUENCE: 165
tgcctagtgg gttcacctgc cca                                              23

<210> SEQ ID NO 166
<211> LENGTH: 23
<212> TYPE: DNA
<213> ORGANISM: Homo sapiens;

<400> SEQUENCE: 166
tgcctagtgg ggtcacctgc cca                                              23

<210> SEQ ID NO 167
<211> LENGTH: 23
<212> TYPE: DNA
<213> ORGANISM: Homo sapiens;

<400> SEQUENCE: 167
tgggcaggtg aacccactag gca                                              23

<210> SEQ ID NO 168
<211> LENGTH: 23

<212> TYPE: DNA
<213> ORGANISM: Homo sapiens;

<400> SEQUENCE: 168
tgggcaggtg accccactag gca                                              23

<210> SEQ ID NO 169
<211> LENGTH: 21
<212> TYPE: DNA
<213> ORGANISM: Homo sapiens;

<400> SEQUENCE: 169
aggaagagat cgtgagggca g                                                21

<210> SEQ ID NO 170
<211> LENGTH: 21
<212> TYPE: DNA
<213> ORGANISM: Homo sapiens;

<400> SEQUENCE: 170
aggaagagat tgtgagggca g                                                21

<210> SEQ ID NO 171
<211> LENGTH: 21
<212> TYPE: DNA
<213> ORGANISM: Homo sapiens;

<400> SEQUENCE: 171
aggaagagat cgtgagggca g                                                21

<210> SEQ ID NO 172
<211> LENGTH: 21
<212> TYPE: DNA
<213> ORGANISM: Homo sapiens;

<400> SEQUENCE: 172
aggaagagat tgtgagggca g                                                21

<210> SEQ ID NO 173
<211> LENGTH: 21
<212> TYPE: DNA
<213> ORGANISM: Homo sapiens;

<400> SEQUENCE: 173
ttccctggac gggctgttcc c                                                21

<210> SEQ ID NO 174
<211> LENGTH: 21
<212> TYPE: DNA
<213> ORGANISM: Homo sapiens;

<400> SEQUENCE: 174
ttccctggac aggctgttcc c                                                21

<210> SEQ ID NO 175
<211> LENGTH: 21
<212> TYPE: DNA
<213> ORGANISM: Homo sapiens;

<400> SEQUENCE: 175
gggaacagcc cgtccaggga a                                                21

<210> SEQ ID NO 176
<211> LENGTH: 21

```
<212> TYPE: DNA
<213> ORGANISM: Homo sapiens;

<400> SEQUENCE: 176
gggaacagcc tgtccaggga a                                    21

<210> SEQ ID NO 177
<211> LENGTH: 25
<212> TYPE: DNA
<213> ORGANISM: Homo sapiens;

<400> SEQUENCE: 177
acctatcttc ttcgacacat gggat                                25

<210> SEQ ID NO 178
<211> LENGTH: 25
<212> TYPE: DNA
<213> ORGANISM: Homo sapiens;

<400> SEQUENCE: 178
acctatcttc tttgacacat gggat                                25

<210> SEQ ID NO 179
<211> LENGTH: 25
<212> TYPE: DNA
<213> ORGANISM: Homo sapiens;

<400> SEQUENCE: 179
atcccatgtg tcgaagaaga taggt                                25

<210> SEQ ID NO 180
<211> LENGTH: 25
<212> TYPE: DNA
<213> ORGANISM: Homo sapiens;

<400> SEQUENCE: 180
atcccatgtg tcaaagaaga taggt                                25

<210> SEQ ID NO 181
<211> LENGTH: 23
<212> TYPE: DNA
<213> ORGANISM: Homo sapiens;

<400> SEQUENCE: 181
agggtgtgga cgtcttgtgc tct                                  23

<210> SEQ ID NO 182
<211> LENGTH: 23
<212> TYPE: DNA
<213> ORGANISM: Homo sapiens;

<400> SEQUENCE: 182
agggtgtgga catcttgtgc tct                                  23

<210> SEQ ID NO 183
<211> LENGTH: 23
<212> TYPE: DNA
<213> ORGANISM: Homo sapiens;

<400> SEQUENCE: 183
agagcacaag acgtccacac cct                                  23

<210> SEQ ID NO 184
<211> LENGTH: 23
```

```
<212> TYPE: DNA
<213> ORGANISM: Homo sapiens;

<400> SEQUENCE: 184
agagcacaag atgtccacac cct                                              23

<210> SEQ ID NO 185
<211> LENGTH: 23
<212> TYPE: DNA
<213> ORGANISM: Homo sapiens;

<400> SEQUENCE: 185
tgggattttc cgatgctaaa gga                                              23

<210> SEQ ID NO 186
<211> LENGTH: 23
<212> TYPE: DNA
<213> ORGANISM: Homo sapiens;

<400> SEQUENCE: 186
tgggattttc ccatgctaaa gga                                              23

<210> SEQ ID NO 187
<211> LENGTH: 23
<212> TYPE: DNA
<213> ORGANISM: Homo sapiens;

<400> SEQUENCE: 187
tcctttagca tcggaaaatc cca                                              23

<210> SEQ ID NO 188
<211> LENGTH: 23
<212> TYPE: DNA
<213> ORGANISM: Homo sapiens;

<400> SEQUENCE: 188
tcctttagca tgggaaaatc cca                                              23

<210> SEQ ID NO 189
<211> LENGTH: 23
<212> TYPE: DNA
<213> ORGANISM: Homo sapiens;

<400> SEQUENCE: 189
tccaggtgta actgttgagg agg                                              23

<210> SEQ ID NO 190
<211> LENGTH: 23
<212> TYPE: DNA
<213> ORGANISM: Homo sapiens;

<400> SEQUENCE: 190
tccaggtgta agtgttgagg agg                                              23

<210> SEQ ID NO 191
<211> LENGTH: 23
<212> TYPE: DNA
<213> ORGANISM: Homo sapiens;

<400> SEQUENCE: 191
cctcctcaac agttacacct gga                                              23

<210> SEQ ID NO 192
<211> LENGTH: 23
```

```
<212> TYPE: DNA
<213> ORGANISM: Homo sapiens;

<400> SEQUENCE: 192
cctcctcaac acttacacct gga                                          23

<210> SEQ ID NO 193
<211> LENGTH: 25
<212> TYPE: DNA
<213> ORGANISM: Homo sapiens;

<400> SEQUENCE: 193
aaaaaagggt gaggattcca atcag                                        25

<210> SEQ ID NO 194
<211> LENGTH: 25
<212> TYPE: DNA
<213> ORGANISM: Homo sapiens;

<400> SEQUENCE: 194
aaaaaagggt gaagattcca atcag                                        25

<210> SEQ ID NO 195
<211> LENGTH: 23
<212> TYPE: DNA
<213> ORGANISM: Homo sapiens;

<400> SEQUENCE: 195
aaaaagggtg aggattccaa tca                                          23

<210> SEQ ID NO 196
<211> LENGTH: 23
<212> TYPE: DNA
<213> ORGANISM: Homo sapiens;

<400> SEQUENCE: 196
aaaaagggtg aagattccaa tca                                          23

<210> SEQ ID NO 197
<211> LENGTH: 21
<212> TYPE: DNA
<213> ORGANISM: Homo sapiens;

<400> SEQUENCE: 197
gatgaaatcg gctcccgcag a                                            21

<210> SEQ ID NO 198
<211> LENGTH: 21
<212> TYPE: DNA
<213> ORGANISM: Homo sapiens;

<400> SEQUENCE: 198
gatgaaatcg actcccgcag a                                            21

<210> SEQ ID NO 199
<211> LENGTH: 21
<212> TYPE: DNA
<213> ORGANISM: Homo sapiens;

<400> SEQUENCE: 199
gatgaaatcg gctcccgcag a                                            21

<210> SEQ ID NO 200
<211> LENGTH: 21
```

<212> TYPE: DNA
<213> ORGANISM: Homo sapiens;

<400> SEQUENCE: 200
gatgaaatcg actcccgcag a                                              21

<210> SEQ ID NO 201
<211> LENGTH: 23
<212> TYPE: DNA
<213> ORGANISM: Homo sapiens;

<400> SEQUENCE: 201
acagagagga atcatggcag aaa                                            23

<210> SEQ ID NO 202
<211> LENGTH: 23
<212> TYPE: DNA
<213> ORGANISM: Homo sapiens;

<400> SEQUENCE: 202
acagagagga accatggcag aaa                                            23

<210> SEQ ID NO 203
<211> LENGTH: 21
<212> TYPE: DNA
<213> ORGANISM: Homo sapiens;

<400> SEQUENCE: 203
ttctgccatg attcctctct g                                              21

<210> SEQ ID NO 204
<211> LENGTH: 21
<212> TYPE: DNA
<213> ORGANISM: Homo sapiens;

<400> SEQUENCE: 204
ttctgccatg gttcctctct g                                              21

<210> SEQ ID NO 205
<211> LENGTH: 23
<212> TYPE: DNA
<213> ORGANISM: Homo sapiens;

<400> SEQUENCE: 205 cgggggtgc tctctcccag ggc                                             23

<210> SEQ ID NO 206
<211> LENGTH: 23
<212> TYPE: DNA
<213> ORGANISM: Homo sapiens;

<400> SEQUENCE: 206 cgggggtgc tgtctcccag ggc                                             23

<210> SEQ ID NO 207
<211> LENGTH: 23
<212> TYPE: DNA
<213> ORGANISM: Homo sapiens;

<400> SEQUENCE: 207
gccctgggag agagcacccc ccg                                            23

<210> SEQ ID NO 208
<211> LENGTH: 23

-continued

<212> TYPE: DNA
<213> ORGANISM: Homo sapiens;

<400> SEQUENCE: 208
gccctgggag acagcacccc ccg    23

<210> SEQ ID NO 209
<211> LENGTH: 23
<212> TYPE: DNA
<213> ORGANISM: Homo sapiens;

<400> SEQUENCE: 209
caggtttgag ggtgctgtgg gca    23

<210> SEQ ID NO 210
<211> LENGTH: 23
<212> TYPE: DNA
<213> ORGANISM: Homo sapiens;

<400> SEQUENCE: 210
caggtttgag gttgctgtgg gca    23

<210> SEQ ID NO 211
<211> LENGTH: 19
<212> TYPE: DNA
<213> ORGANISM: Homo sapiens;

<400> SEQUENCE: 211
ggtttgaggg tgctgtggg    19

<210> SEQ ID NO 212
<211> LENGTH: 19
<212> TYPE: DNA
<213> ORGANISM: Homo sapiens;

<400> SEQUENCE: 212
ggtttgaggt tgctgtggg    19

<210> SEQ ID NO 213
<211> LENGTH: 23
<212> TYPE: DNA
<213> ORGANISM: Homo sapiens;

<400> SEQUENCE: 213
cttctttggg aagggggaagt agg    23

<210> SEQ ID NO 214
<211> LENGTH: 23
<212> TYPE: DNA
<213> ORGANISM: Homo sapiens;

<400> SEQUENCE: 214
cttctttggg aggggggaagt agg    23

<210> SEQ ID NO 215
<211> LENGTH: 23
<212> TYPE: DNA
<213> ORGANISM: Homo sapiens;

<400> SEQUENCE: 215
cctacttccc ctagggtttc ttc    23

<210> SEQ ID NO 216
<211> LENGTH: 23

```
<212> TYPE: DNA
<213> ORGANISM: Homo sapiens;

<400> SEQUENCE: 216
cctacttccc ccagggtttc ttc                                          23

<210> SEQ ID NO 217
<211> LENGTH: 19
<212> TYPE: DNA
<213> ORGANISM: Homo sapiens;

<400> SEQUENCE: 217
accccgtccc catgcccct                                               19

<210> SEQ ID NO 218
<211> LENGTH: 19
<212> TYPE: DNA
<213> ORGANISM: Homo sapiens;

<400> SEQUENCE: 218
accccgtcct catgcccct                                               19

<210> SEQ ID NO 219
<211> LENGTH: 19
<212> TYPE: DNA
<213> ORGANISM: Homo sapiens;

<400> SEQUENCE: 219
accccgtccc catgcccct                                               19

<210> SEQ ID NO 220
<211> LENGTH: 19
<212> TYPE: DNA
<213> ORGANISM: Homo sapiens;

<400> SEQUENCE: 220
accccgtcct catgcccct                                               19

<210> SEQ ID NO 221
<211> LENGTH: 23
<212> TYPE: DNA
<213> ORGANISM: Homo sapiens;

<400> SEQUENCE: 221
gacgcctggc cggccggccg cgg                                          23

<210> SEQ ID NO 222
<211> LENGTH: 23
<212> TYPE: DNA
<213> ORGANISM: Homo sapiens;

<400> SEQUENCE: 222
gacgcctggc ccgccggccg cgg                                          23

<210> SEQ ID NO 223
<211> LENGTH: 23
<212> TYPE: DNA
<213> ORGANISM: Homo sapiens;

<400> SEQUENCE: 223
ccgcggccgg ccggccaggc gtc                                          23

<210> SEQ ID NO 224
<211> LENGTH: 23
```

```
<212> TYPE: DNA
<213> ORGANISM: Homo sapiens;

<400> SEQUENCE: 224
ccgcggccgg cgggccaggc gtc                                    23

<210> SEQ ID NO 225
<211> LENGTH: 23
<212> TYPE: DNA
<213> ORGANISM: Homo sapiens;

<400> SEQUENCE: 225
cttctttggg aggggaagt agg                                     23

<210> SEQ ID NO 226
<211> LENGTH: 23
<212> TYPE: DNA
<213> ORGANISM: Homo sapiens;

<400> SEQUENCE: 226
cttctttggg aagggaagt agg                                     23

<210> SEQ ID NO 227
<211> LENGTH: 23
<212> TYPE: DNA
<213> ORGANISM: Homo sapiens;

<400> SEQUENCE: 227
cctacttccc ccagggtttc ttc                                    23

<210> SEQ ID NO 228
<211> LENGTH: 23
<212> TYPE: DNA
<213> ORGANISM: Homo sapiens;

<400> SEQUENCE: 228
cctacttccc ctagggtttc ttc                                    23

<210> SEQ ID NO 229
<211> LENGTH: 25
<212> TYPE: DNA
<213> ORGANISM: Homo sapiens;

<400> SEQUENCE: 229
tgggatagag gagcattagt tgcca                                  25

<210> SEQ ID NO 230
<211> LENGTH: 25
<212> TYPE: DNA
<213> ORGANISM: Homo sapiens;

<400> SEQUENCE: 230
tgggatagag gaacattagt tgcca                                  25

<210> SEQ ID NO 231
<211> LENGTH: 23
<212> TYPE: DNA
<213> ORGANISM: Homo sapiens;

<400> SEQUENCE: 231
gggatagagg agcattagtt gcc                                    23

<210> SEQ ID NO 232
<211> LENGTH: 23
```

```
<212> TYPE: DNA
<213> ORGANISM: Homo sapiens;

<400> SEQUENCE: 232
gggatagagg aacattagtt gcc                                       23

<210> SEQ ID NO 233
<211> LENGTH: 25
<212> TYPE: DNA
<213> ORGANISM: Homo sapiens;

<400> SEQUENCE: 233
tctgtaagta gatataactt ttcaa                                     25

<210> SEQ ID NO 234
<211> LENGTH: 25
<212> TYPE: DNA
<213> ORGANISM: Homo sapiens;

<400> SEQUENCE: 234
tctgtaagta gacataactt ttcaa                                     25

<210> SEQ ID NO 235
<211> LENGTH: 23
<212> TYPE: DNA
<213> ORGANISM: Homo sapiens;

<400> SEQUENCE: 235
ctgtaagtag atataacttt tca                                       23

<210> SEQ ID NO 236
<211> LENGTH: 23
<212> TYPE: DNA
<213> ORGANISM: Homo sapiens;

<400> SEQUENCE: 236
ctgtaagtag acataacttt tca                                       23

<210> SEQ ID NO 237
<211> LENGTH: 23
<212> TYPE: DNA
<213> ORGANISM: Homo sapiens;

<400> SEQUENCE: 237
acgggaagtc cttgatctgt aca                                       23

<210> SEQ ID NO 238
<211> LENGTH: 23
<212> TYPE: DNA
<213> ORGANISM: Homo sapiens;

<400> SEQUENCE: 238
acgggaagtc cctgatctgt aca                                       23

<210> SEQ ID NO 239
<211> LENGTH: 23
<212> TYPE: DNA
<213> ORGANISM: Homo sapiens;

<400> SEQUENCE: 239
tgtacagatc aaggacttcc cgt                                       23

<210> SEQ ID NO 240
<211> LENGTH: 23
```

```
<212> TYPE: DNA
<213> ORGANISM: Homo sapiens;

<400> SEQUENCE: 240
tgtacagatc agggacttcc cgt                                              23

<210> SEQ ID NO 241
<211> LENGTH: 23
<212> TYPE: DNA
<213> ORGANISM: Homo sapiens;

<400> SEQUENCE: 241
ctggctgcct agagttcaac cct                                              23

<210> SEQ ID NO 242
<211> LENGTH: 23
<212> TYPE: DNA
<213> ORGANISM: Homo sapiens;

<400> SEQUENCE: 242
ctggctgcct acagttcaac cct                                              23

<210> SEQ ID NO 243
<211> LENGTH: 23
<212> TYPE: DNA
<213> ORGANISM: Homo sapiens;

<400> SEQUENCE: 243
agggttgaac tctaggcagc cag                                              23

<210> SEQ ID NO 244
<211> LENGTH: 23
<212> TYPE: DNA
<213> ORGANISM: Homo sapiens;

<400> SEQUENCE: 244
agggttgaac tgtaggcagc cag                                              23

<210> SEQ ID NO 245
<211> LENGTH: 23
<212> TYPE: DNA
<213> ORGANISM: Homo sapiens;

<400> SEQUENCE: 245
gcaggtgacc attgacggca gga                                              23

<210> SEQ ID NO 246
<211> LENGTH: 23
<212> TYPE: DNA
<213> ORGANISM: Homo sapiens;

<400> SEQUENCE: 246
tcctgccgtc aatggtcacc tgc                                              23

<210> SEQ ID NO 247
<211> LENGTH: 23
<212> TYPE: DNA
<213> ORGANISM: Homo sapiens;

<400> SEQUENCE: 247
gcaggtgacc actgacggca gga                                              23

<210> SEQ ID NO 248
<211> LENGTH: 23
```

-continued

<212> TYPE: DNA
<213> ORGANISM: Homo sapiens;

<400> SEQUENCE: 248
tcctgccgtc agtggtcacc tgc                                              23

<210> SEQ ID NO 249
<211> LENGTH: 23
<212> TYPE: DNA
<213> ORGANISM: Homo sapiens;

<400> SEQUENCE: 249
gaatctggta cctggaccaa atc                                              23

<210> SEQ ID NO 250
<211> LENGTH: 23
<212> TYPE: DNA
<213> ORGANISM: Homo sapiens;

<400> SEQUENCE: 250
gatttggtcc aggtaccaga ttc                                              23

<210> SEQ ID NO 251
<211> LENGTH: 23
<212> TYPE: DNA
<213> ORGANISM: Homo sapiens;

<400> SEQUENCE: 251
gaatctggta cttggaccaa atc                                              23

<210> SEQ ID NO 252
<211> LENGTH: 23
<212> TYPE: DNA
<213> ORGANISM: Homo sapiens;

<400> SEQUENCE: 252
gatttggtcc aagtaccaga ttc                                              23

<210> SEQ ID NO 253
<211> LENGTH: 23
<212> TYPE: DNA
<213> ORGANISM: Homo sapiens;

<400> SEQUENCE: 253
agaagtgctg aaaaatatat tta                                              23

<210> SEQ ID NO 254
<211> LENGTH: 23
<212> TYPE: DNA
<213> ORGANISM: Homo sapiens;

<400> SEQUENCE: 254
taaatatatt tttcagcact tct                                              23

<210> SEQ ID NO 255
<211> LENGTH: 23
<212> TYPE: DNA
<213> ORGANISM: Homo sapiens;

<400> SEQUENCE: 255
agaagtgctg agaaatatat tta                                              23

<210> SEQ ID NO 256
<211> LENGTH: 23

```
<212> TYPE: DNA
<213> ORGANISM: Homo sapiens;

<400> SEQUENCE: 256
taaatatatt tctcagcact tct                                              23

<210> SEQ ID NO 257
<211> LENGTH: 23
<212> TYPE: DNA
<213> ORGANISM: Homo sapiens;

<400> SEQUENCE: 257
acctggtgat ggatcccttacta                                               23

<210> SEQ ID NO 258
<211> LENGTH: 23
<212> TYPE: DNA
<213> ORGANISM: Homo sapiens;

<400> SEQUENCE: 258
tagtaaggga tccatcacca ggt                                              23

<210> SEQ ID NO 259
<211> LENGTH: 23
<212> TYPE: DNA
<213> ORGANISM: Homo sapiens;

<400> SEQUENCE: 259
acctggtgat gaatcccttacta                                               23

<210> SEQ ID NO 260
<211> LENGTH: 23
<212> TYPE: DNA
<213> ORGANISM: Homo sapiens;

<400> SEQUENCE: 260
tagtaaggga ttcatcacca ggt                                              23

<210> SEQ ID NO 261
<211> LENGTH: 23
<212> TYPE: DNA
<213> ORGANISM: Homo sapiens;

<400> SEQUENCE: 261
aagaagaaac cggggtgggt ggt                                              23

<210> SEQ ID NO 262
<211> LENGTH: 23
<212> TYPE: DNA
<213> ORGANISM: Homo sapiens;

<400> SEQUENCE: 262
accacccacc ccggtttctt ctt                                              23

<210> SEQ ID NO 263
<211> LENGTH: 23
<212> TYPE: DNA
<213> ORGANISM: Homo sapiens;

<400> SEQUENCE: 263
aagaagaaac cagggtgggt ggt                                              23

<210> SEQ ID NO 264
<211> LENGTH: 23
```

<212> TYPE: DNA
<213> ORGANISM: Homo sapiens;

<400> SEQUENCE: 264
accacccacc ctggtttctt ctt                                                 23

<210> SEQ ID NO 265
<211> LENGTH: 23
<212> TYPE: DNA
<213> ORGANISM: Homo sapiens;

<400> SEQUENCE: 265 ttcccccag cgtggcagga tct                                                  23

<210> SEQ ID NO 266
<211> LENGTH: 23
<212> TYPE: DNA
<213> ORGANISM: Homo sapiens;

<400> SEQUENCE: 266 ttcccccag catggcagga tct                                                  23

<210> SEQ ID NO 267
<211> LENGTH: 23
<212> TYPE: DNA
<213> ORGANISM: Homo sapiens;

<400> SEQUENCE: 267
agatcctgcc acgctggggg gaa                                                 23

<210> SEQ ID NO 268
<211> LENGTH: 23
<212> TYPE: DNA
<213> ORGANISM: Homo sapiens;

<400> SEQUENCE: 268
agatcctgcc atgctggggg gaa                                                 23

<210> SEQ ID NO 269
<211> LENGTH: 23
<212> TYPE: DNA
<213> ORGANISM: Homo sapiens;

<400> SEQUENCE: 269
tcaagaactg atttgtctgt gtg                                                 23

<210> SEQ ID NO 270
<211> LENGTH: 23
<212> TYPE: DNA
<213> ORGANISM: Homo sapiens;

<400> SEQUENCE: 270
tcaagaactg agttgtctgt gtg                                                 23

<210> SEQ ID NO 271
<211> LENGTH: 23
<212> TYPE: DNA
<213> ORGANISM: Homo sapiens;

<400> SEQUENCE: 271
cacacagaca aatcagttct tga                                                 23

<210> SEQ ID NO 272
<211> LENGTH: 23

<212> TYPE: DNA
<213> ORGANISM: Homo sapiens;

<400> SEQUENCE: 272
cacacagaca actcagttct tga                                              23

<210> SEQ ID NO 273
<211> LENGTH: 23
<212> TYPE: DNA
<213> ORGANISM: Homo sapiens;

<400> SEQUENCE: 273 ttcccccag catggcagga tct                                               23

<210> SEQ ID NO 274
<211> LENGTH: 23
<212> TYPE: DNA
<213> ORGANISM: Homo sapiens;

<400> SEQUENCE: 274 ttcccccag cgtggcagga tct                                               23

<210> SEQ ID NO 275
<211> LENGTH: 23
<212> TYPE: DNA
<213> ORGANISM: Homo sapiens;

<400> SEQUENCE: 275
agatcctgcc atgctggggg gaa                                              23

<210> SEQ ID NO 276
<211> LENGTH: 23
<212> TYPE: DNA
<213> ORGANISM: Homo sapiens;

<400> SEQUENCE: 276
agatcctgcc acgctggggg gaa                                              23

<210> SEQ ID NO 277
<211> LENGTH: 23
<212> TYPE: DNA
<213> ORGANISM: Homo sapiens;

<400> SEQUENCE: 277
ttcagaggtg tagggagggc tta                                              23

<210> SEQ ID NO 278
<211> LENGTH: 23
<212> TYPE: DNA
<213> ORGANISM: Homo sapiens;

<400> SEQUENCE: 278
ttcagaggtg tggggagggc tta                                              23

<210> SEQ ID NO 279
<211> LENGTH: 23
<212> TYPE: DNA
<213> ORGANISM: Homo sapiens;

<400> SEQUENCE: 279
taagccctcc ctacacctct gaa                                              23

<210> SEQ ID NO 280
<211> LENGTH: 23

```
<212> TYPE: DNA
<213> ORGANISM: Homo sapiens;

<400> SEQUENCE: 280
taagccctcc ccacacctct gaa                                    23

<210> SEQ ID NO 281
<211> LENGTH: 23
<212> TYPE: DNA
<213> ORGANISM: Homo sapiens;

<400> SEQUENCE: 281
tggcacccaa tggaagccat gcg                                    23

<210> SEQ ID NO 282
<211> LENGTH: 23
<212> TYPE: DNA
<213> ORGANISM: Homo sapiens;

<400> SEQUENCE: 282
tggcacccaa tagaagccat gcg                                    23

<210> SEQ ID NO 283
<211> LENGTH: 23
<212> TYPE: DNA
<213> ORGANISM: Homo sapiens;

<400> SEQUENCE: 283
cgcatggctt ccattgggtg cca                                    23

<210> SEQ ID NO 284
<211> LENGTH: 23
<212> TYPE: DNA
<213> ORGANISM: Homo sapiens;

<400> SEQUENCE: 284
cgcatggctt ctattgggtg cca                                    23

<210> SEQ ID NO 285
<211> LENGTH: 23
<212> TYPE: DNA
<213> ORGANISM: Homo sapiens;

<400> SEQUENCE: 285
gaccagtgaa gaaagtgtct ttg                                    23

<210> SEQ ID NO 286
<211> LENGTH: 23
<212> TYPE: DNA
<213> ORGANISM: Homo sapiens;

<400> SEQUENCE: 286
gaccagtgaa gcaagtgtct ttg                                    23

<210> SEQ ID NO 287
<211> LENGTH: 23
<212> TYPE: DNA
<213> ORGANISM: Homo sapiens;

<400> SEQUENCE: 287
caaagacact ttcttcactg gtc                                    23

<210> SEQ ID NO 288
<211> LENGTH: 23
```

<212> TYPE: DNA
<213> ORGANISM: Homo sapiens;

<400> SEQUENCE: 288
caaagacact tgcttcactg gtc                                              23

<210> SEQ ID NO 289
<211> LENGTH: 23
<212> TYPE: DNA
<213> ORGANISM: Homo sapiens;

<400> SEQUENCE: 289
ggcagacagc tgtcactttc cag                                              23

<210> SEQ ID NO 290
<211> LENGTH: 23
<212> TYPE: DNA
<213> ORGANISM: Homo sapiens;

<400> SEQUENCE: 290
ggcagacagc tatcactttc cag                                              23

<210> SEQ ID NO 291
<211> LENGTH: 23
<212> TYPE: DNA
<213> ORGANISM: Homo sapiens;

<400> SEQUENCE: 291
ctggaaagtg acagctgtct gcc                                              23

<210> SEQ ID NO 292
<211> LENGTH: 23
<212> TYPE: DNA
<213> ORGANISM: Homo sapiens;

<400> SEQUENCE: 292
ctggaaagtg atagctgtct gcc                                              23

<210> SEQ ID NO 293
<211> LENGTH: 23
<212> TYPE: DNA
<213> ORGANISM: Homo sapiens;

<400> SEQUENCE: 293
tgaaaacatt gcgaaataca aag                                              23

<210> SEQ ID NO 294
<211> LENGTH: 23
<212> TYPE: DNA
<213> ORGANISM: Homo sapiens;

<400> SEQUENCE: 294
tgaaaacatt gtgaaataca aag                                              23

<210> SEQ ID NO 295
<211> LENGTH: 21
<212> TYPE: DNA
<213> ORGANISM: Homo sapiens;

<400> SEQUENCE: 295
tttgtatttc gcaatgtttt c                                                21

<210> SEQ ID NO 296
<211> LENGTH: 21

```
<212> TYPE: DNA
<213> ORGANISM: Homo sapiens;

<400> SEQUENCE: 296
tttgtatttc acaatgtttt c                                        21

<210> SEQ ID NO 297
<211> LENGTH: 25
<212> TYPE: DNA
<213> ORGANISM: Homo sapiens;

<400> SEQUENCE: 297
ccttgcaacc ctggcaaagg taatg                                    25

<210> SEQ ID NO 298
<211> LENGTH: 25
<212> TYPE: DNA
<213> ORGANISM: Homo sapiens;

<400> SEQUENCE: 298
ccttgcaacc ctcgcaaagg taatg                                    25

<210> SEQ ID NO 299
<211> LENGTH: 25
<212> TYPE: DNA
<213> ORGANISM: Homo sapiens;

<400> SEQUENCE: 299
cattaccttt gccagggttg caagg                                    25

<210> SEQ ID NO 300
<211> LENGTH: 25
<212> TYPE: DNA
<213> ORGANISM: Homo sapiens;

<400> SEQUENCE: 300
cattaccttt gcgagggttg caagg                                    25

<210> SEQ ID NO 301
<211> LENGTH: 25
<212> TYPE: DNA
<213> ORGANISM: Homo sapiens;

<400> SEQUENCE: 301
tgcagggggc ttgttgggag taaaa                                    25

<210> SEQ ID NO 302
<211> LENGTH: 25
<212> TYPE: DNA
<213> ORGANISM: Homo sapiens;

<400> SEQUENCE: 302
tgcagggggc tttttgggag taaaa                                    25

<210> SEQ ID NO 303
<211> LENGTH: 21
<212> TYPE: DNA
<213> ORGANISM: Homo sapiens;

<400> SEQUENCE: 303
ttactcccaa caagccccct g                                        21

<210> SEQ ID NO 304
<211> LENGTH: 21
```

```
<212> TYPE: DNA
<213> ORGANISM: Homo sapiens;

<400> SEQUENCE: 304
ttactcccaa aaagcccct g                                              21

<210> SEQ ID NO 305
<211> LENGTH: 23
<212> TYPE: DNA
<213> ORGANISM: Homo sapiens;

<400> SEQUENCE: 305
aagagaatcc cagagcagcc tgt                                           23

<210> SEQ ID NO 306
<211> LENGTH: 23
<212> TYPE: DNA
<213> ORGANISM: Homo sapiens;

<400> SEQUENCE: 306
aagagaatcc ccgagcagcc tgt                                           23

<210> SEQ ID NO 307
<211> LENGTH: 23
<212> TYPE: DNA
<213> ORGANISM: Homo sapiens;

<400> SEQUENCE: 307
acaggctgct ctgggattct ctt                                           23

<210> SEQ ID NO 308
<211> LENGTH: 23
<212> TYPE: DNA
<213> ORGANISM: Homo sapiens;

<400> SEQUENCE: 308
acaggctgct cggggattct ctt                                           23

<210> SEQ ID NO 309
<211> LENGTH: 23
<212> TYPE: DNA
<213> ORGANISM: Homo sapiens;

<400> SEQUENCE: 309
taaactaatt gcctcacatt gtc                                           23

<210> SEQ ID NO 310
<211> LENGTH: 23
<212> TYPE: DNA
<213> ORGANISM: Homo sapiens;

<400> SEQUENCE: 310
taaactaatt gtctcacatt gtc                                           23

<210> SEQ ID NO 311
<211> LENGTH: 23
<212> TYPE: DNA
<213> ORGANISM: Homo sapiens;

<400> SEQUENCE: 311
gacaatgtga ggcaattagt tta                                           23

<210> SEQ ID NO 312
<211> LENGTH: 23
```

```
<212> TYPE: DNA
<213> ORGANISM: Homo sapiens;

<400> SEQUENCE: 312
gacaatgtga gacaattagt tta                                         23

<210> SEQ ID NO 313
<211> LENGTH: 23
<212> TYPE: DNA
<213> ORGANISM: Homo sapiens;

<400> SEQUENCE: 313
gtcctgctga gccgcgagct gtt                                         23

<210> SEQ ID NO 314
<211> LENGTH: 23
<212> TYPE: DNA
<213> ORGANISM: Homo sapiens;

<400> SEQUENCE: 314
gtcctgctga gtcgcgagct gtt                                         23

<210> SEQ ID NO 315
<211> LENGTH: 21
<212> TYPE: DNA
<213> ORGANISM: Homo sapiens;

<400> SEQUENCE: 315
acagctcgcg gctcagcagg a                                           21

<210> SEQ ID NO 316
<211> LENGTH: 21
<212> TYPE: DNA
<213> ORGANISM: Homo sapiens;

<400> SEQUENCE: 316
acagctcgcg actcagcagg a                                           21

<210> SEQ ID NO 317
<211> LENGTH: 23
<212> TYPE: DNA
<213> ORGANISM: Homo sapiens;

<400> SEQUENCE: 317
aggtcacccg caaggtgacc gtg                                         23

<210> SEQ ID NO 318
<211> LENGTH: 23
<212> TYPE: DNA
<213> ORGANISM: Homo sapiens;

<400> SEQUENCE: 318
cacggtcacc ttgcgggtga cct                                         23

<210> SEQ ID NO 319
<211> LENGTH: 23
<212> TYPE: DNA
<213> ORGANISM: Homo sapiens;

<400> SEQUENCE: 319
aggtcacccg cgaggtgacc gtg                                         23

<210> SEQ ID NO 320
<211> LENGTH: 23
```

<210> SEQ ID NO 320
<211> LENGTH: 23
<212> TYPE: DNA
<213> ORGANISM: Homo sapiens;

<400> SEQUENCE: 320
cacggtcacc tcgcgggtga cct                                              23

<210> SEQ ID NO 321
<211> LENGTH: 23
<212> TYPE: DNA
<213> ORGANISM: Homo sapiens;

<400> SEQUENCE: 321
tgggcgtgat gacaccaagg gag                                              23

<210> SEQ ID NO 322
<211> LENGTH: 23
<212> TYPE: DNA
<213> ORGANISM: Homo sapiens;

<400> SEQUENCE: 322
ctcccttggt gtcatcacgc cca                                              23

<210> SEQ ID NO 323
<211> LENGTH: 23
<212> TYPE: DNA
<213> ORGANISM: Homo sapiens;

<400> SEQUENCE: 323
tgggcgtgat ggcaccaagg gag                                              23

<210> SEQ ID NO 324
<211> LENGTH: 23
<212> TYPE: DNA
<213> ORGANISM: Homo sapiens;

<400> SEQUENCE: 324
ctcccttggt gccatcacgc cca                                              23

<210> SEQ ID NO 325
<211> LENGTH: 23
<212> TYPE: DNA
<213> ORGANISM: Homo sapiens;

<400> SEQUENCE: 325
gagaacattg tcccccagtg ctg                                              23

<210> SEQ ID NO 326
<211> LENGTH: 23
<212> TYPE: DNA
<213> ORGANISM: Homo sapiens;

<400> SEQUENCE: 326
cagcactggg ggacaatgtt ctc                                              23

<210> SEQ ID NO 327
<211> LENGTH: 23
<212> TYPE: DNA
<213> ORGANISM: Homo sapiens;

<400> SEQUENCE: 327
gagaacattg ttccccagtg ctg                                              23

<210> SEQ ID NO 328
<211> LENGTH: 23

```
<212> TYPE: DNA
<213> ORGANISM: Homo sapiens;

<400> SEQUENCE: 328
cagcactggg gaacaatgtt ctc                                              23

<210> SEQ ID NO 329
<211> LENGTH: 23
<212> TYPE: DNA
<213> ORGANISM: Homo sapiens;

<400> SEQUENCE: 329
cttcaggcta ttaaagaagc att                                              23

<210> SEQ ID NO 330
<211> LENGTH: 23
<212> TYPE: DNA
<213> ORGANISM: Homo sapiens;

<400> SEQUENCE: 330
cttcaggcta tcaaagaagc att                                              23

<210> SEQ ID NO 331
<211> LENGTH: 23
<212> TYPE: DNA
<213> ORGANISM: Homo sapiens;

<400> SEQUENCE: 331
aatgcttctt taatagcctg aag                                              23

<210> SEQ ID NO 332
<211> LENGTH: 23
<212> TYPE: DNA
<213> ORGANISM: Homo sapiens;

<400> SEQUENCE: 332
aatgcttctt tgatagcctg aag                                              23

<210> SEQ ID NO 333
<211> LENGTH: 23
<212> TYPE: DNA
<213> ORGANISM: Homo sapiens;

<400> SEQUENCE: 333
gaagtttcag tatctcctgt gtg                                              23

<210> SEQ ID NO 334
<211> LENGTH: 23
<212> TYPE: DNA
<213> ORGANISM: Homo sapiens;

<400> SEQUENCE: 334
gaagtttcag tttctcctgt gtg                                              23

<210> SEQ ID NO 335
<211> LENGTH: 23
<212> TYPE: DNA
<213> ORGANISM: Homo sapiens;

<400> SEQUENCE: 335
cacacaggag atactgaaac ttc                                              23

<210> SEQ ID NO 336
<211> LENGTH: 23
```

```
<212> TYPE: DNA
<213> ORGANISM: Homo sapiens;

<400> SEQUENCE: 336
cacacaggag aaactgaaac ttc                                      23

<210> SEQ ID NO 337
<211> LENGTH: 23
<212> TYPE: DNA
<213> ORGANISM: Homo sapiens;

<400> SEQUENCE: 337
gaagaacgac ataaaagttg ggg                                      23

<210> SEQ ID NO 338
<211> LENGTH: 23
<212> TYPE: DNA
<213> ORGANISM: Homo sapiens;

<400> SEQUENCE: 338
gaagaacgac agaaaagttg ggg                                      23

<210> SEQ ID NO 339
<211> LENGTH: 23
<212> TYPE: DNA
<213> ORGANISM: Homo sapiens;

<400> SEQUENCE: 339
ccccaacttt tatgtcgttc ttc                                      23

<210> SEQ ID NO 340
<211> LENGTH: 23
<212> TYPE: DNA
<213> ORGANISM: Homo sapiens;

<400> SEQUENCE: 340
ccccaacttt tctgtcgttc ttc                                      23

<210> SEQ ID NO 341
<211> LENGTH: 23
<212> TYPE: DNA
<213> ORGANISM: Homo sapiens;

<400> SEQUENCE: 341
atgcaatata cgttgtcttg aga                                      23

<210> SEQ ID NO 342
<211> LENGTH: 23
<212> TYPE: DNA
<213> ORGANISM: Homo sapiens;

<400> SEQUENCE: 342
atgcaatata cattgtcttg aga                                      23

<210> SEQ ID NO 343
<211> LENGTH: 23
<212> TYPE: DNA
<213> ORGANISM: Homo sapiens;

<400> SEQUENCE: 343
tctcaagaca acgtatattg cat                                      23

<210> SEQ ID NO 344
<211> LENGTH: 23
```

```
<212> TYPE: DNA
<213> ORGANISM: Homo sapiens;

<400> SEQUENCE: 344
tctcaagaca atgtatattg cat                                          23

<210> SEQ ID NO 345
<211> LENGTH: 23
<212> TYPE: DNA
<213> ORGANISM: Homo sapiens;

<400> SEQUENCE: 345
gacagcgacg ccgcgagtcc gag                                          23

<210> SEQ ID NO 346
<211> LENGTH: 23
<212> TYPE: DNA
<213> ORGANISM: Homo sapiens;

<400> SEQUENCE: 346
ctcggactcg cggcgtcgct gtc                                          23

<210> SEQ ID NO 347
<211> LENGTH: 23
<212> TYPE: DNA
<213> ORGANISM: Homo sapiens;

<400> SEQUENCE: 347
gacagcgacg ccgcgagtcc gag                                          23

<210> SEQ ID NO 348
<211> LENGTH: 23
<212> TYPE: DNA
<213> ORGANISM: Homo sapiens;

<400> SEQUENCE: 348
ctcggactcg cggcgtcgct gtc                                          23

<210> SEQ ID NO 349
<211> LENGTH: 23
<212> TYPE: DNA
<213> ORGANISM: Homo sapiens;

<400> SEQUENCE: 349
gtcctggcgg cgcctcgtgt gct                                          23

<210> SEQ ID NO 350
<211> LENGTH: 23
<212> TYPE: DNA
<213> ORGANISM: Homo sapiens;

<400> SEQUENCE: 350
gtcctggcgg cacctcgtgt gct                                          23

<210> SEQ ID NO 351
<211> LENGTH: 23
<212> TYPE: DNA
<213> ORGANISM: Homo sapiens;

<400> SEQUENCE: 351
agcacacgag gcgccgccag gac                                          23

<210> SEQ ID NO 352
<211> LENGTH: 23
```

```
<212> TYPE: DNA
<213> ORGANISM: Homo sapiens;

<400> SEQUENCE: 352
agcacacgag gtgccgccag gac                                              23

<210> SEQ ID NO 353
<211> LENGTH: 23
<212> TYPE: DNA
<213> ORGANISM: Homo sapiens;

<400> SEQUENCE: 353 gggtatttt acatccctcc agt                                               23

<210> SEQ ID NO 354
<211> LENGTH: 23
<212> TYPE: DNA
<213> ORGANISM: Homo sapiens;

<400> SEQUENCE: 354 gggtatttt atatccctcc agt                                               23

<210> SEQ ID NO 355
<211> LENGTH: 21
<212> TYPE: DNA
<213> ORGANISM: Homo sapiens;

<400> SEQUENCE: 355 ggtatttta catccctcca g                                                 21

<210> SEQ ID NO 356
<211> LENGTH: 21
<212> TYPE: DNA
<213> ORGANISM: Homo sapiens;

<400> SEQUENCE: 356 ggtatttta tatccctcca g                                                 21

<210> SEQ ID NO 357
<211> LENGTH: 23
<212> TYPE: DNA
<213> ORGANISM: Homo sapiens;

<400> SEQUENCE: 357
cttcaattgt tcgaggttca agc                                              23

<210> SEQ ID NO 358
<211> LENGTH: 23
<212> TYPE: DNA
<213> ORGANISM: Homo sapiens;

<400> SEQUENCE: 358
cttcaattgt ttgaggttca agc                                              23

<210> SEQ ID NO 359
<211> LENGTH: 23
<212> TYPE: DNA
<213> ORGANISM: Homo sapiens;

<400> SEQUENCE: 359
gcttgaacct cgaacaattg aag                                              23

<210> SEQ ID NO 360
<211> LENGTH: 23
```

<212> TYPE: DNA
<213> ORGANISM: Homo sapiens;

<400> SEQUENCE: 360
gcttgaacct caaacaattg aag                                    23

<210> SEQ ID NO 361
<211> LENGTH: 40
<212> TYPE: DNA
<213> ORGANISM: Homo sapiens;

<400> SEQUENCE: 361
gctagatgaa gagcaagcgc caagagtgcc cagagagtcc                  40

<210> SEQ ID NO 362
<211> LENGTH: 41
<212> TYPE: DNA
<213> ORGANISM: Homo sapiens;

<400> SEQUENCE: 362
tacaaccgac agatgtatgt ttctccctaa ggcattttgg t                41

<210> SEQ ID NO 363
<211> LENGTH: 40
<212> TYPE: DNA
<213> ORGANISM: Homo sapiens;

<400> SEQUENCE: 363
gctagatgaa gagcaagcgc tctccactgt gctgatgagg                  40

<210> SEQ ID NO 364
<211> LENGTH: 40
<212> TYPE: DNA
<213> ORGANISM: Homo sapiens;

<400> SEQUENCE: 364
tacaaccgac agatgtatgt tttttcttgc gtgctgacac                  40

<210> SEQ ID NO 365
<211> LENGTH: 40
<212> TYPE: DNA
<213> ORGANISM: Homo sapiens;

<400> SEQUENCE: 365
gctagatgaa gagcaagcgc accctcacca acctctcctc                  40

<210> SEQ ID NO 366
<211> LENGTH: 40
<212> TYPE: DNA
<213> ORGANISM: Homo sapiens;

<400> SEQUENCE: 366
tacaaccgac agatgtatgt acacggaata cgtgggacag                  40

<210> SEQ ID NO 367
<211> LENGTH: 40
<212> TYPE: DNA
<213> ORGANISM: Homo sapiens;

<400> SEQUENCE: 367
gctagatgaa gagcaagcgc cccatgtgtc ttgtccacag                  40

<210> SEQ ID NO 368
<211> LENGTH: 40

```
<212> TYPE: DNA
<213> ORGANISM: Homo sapiens;

<400> SEQUENCE: 368
tacaaccgac agatgtatgt tcgtcagggt cacctctacc                              40

<210> SEQ ID NO 369
<211> LENGTH: 40
<212> TYPE: DNA
<213> ORGANISM: Homo sapiens;

<400> SEQUENCE: 369
gctagatgaa gagcaagcgc cccatgtgtc ttgtccacag                              40

<210> SEQ ID NO 370
<211> LENGTH: 40
<212> TYPE: DNA
<213> ORGANISM: Homo sapiens;

<400> SEQUENCE: 370
tacaaccgac agatgtatgt ccccacagct atgacactca                              40

<210> SEQ ID NO 371
<211> LENGTH: 39
<212> TYPE: DNA
<213> ORGANISM: Homo sapiens;

<400> SEQUENCE: 371
gctagatgaa gagcaagcgc tccagtgggt gtttgttga                               39

<210> SEQ ID NO 372
<211> LENGTH: 40
<212> TYPE: DNA
<213> ORGANISM: Homo sapiens;

<400> SEQUENCE: 372
tacaaccgac agatgtatgt ggatgagacg gcactctagg                              40

<210> SEQ ID NO 373
<211> LENGTH: 39
<212> TYPE: DNA
<213> ORGANISM: Homo sapiens;

<400> SEQUENCE: 373
gctagatgaa gagcaagcgc catcttccct tttgcacct                               39

<210> SEQ ID NO 374
<211> LENGTH: 39
<212> TYPE: DNA
<213> ORGANISM: Homo sapiens;

<400> SEQUENCE: 374
tacaaccgac agatgtatgt gatcccgagg aggactgaa                               39

<210> SEQ ID NO 375
<211> LENGTH: 40
<212> TYPE: DNA
<213> ORGANISM: Homo sapiens;

<400> SEQUENCE: 375
gctagatgaa gagcaagcgc atgctaaggg cctggatgat                              40

<210> SEQ ID NO 376
<211> LENGTH: 40
```

```
<212> TYPE: DNA
<213> ORGANISM: Homo sapiens;

<400> SEQUENCE: 376
tacaaccgac agatgtatgt caggaccctc cctgttacaa                           40

<210> SEQ ID NO 377
<211> LENGTH: 40
<212> TYPE: DNA
<213> ORGANISM: Homo sapiens;

<400> SEQUENCE: 377
gctagatgaa gagcaagcgc ggccaaaaca accatctgag                           40

<210> SEQ ID NO 378
<211> LENGTH: 40
<212> TYPE: DNA
<213> ORGANISM: Homo sapiens;

<400> SEQUENCE: 378
tacaaccgac agatgtatgt tccctcatgg ttgggttaaa                           40

<210> SEQ ID NO 379
<211> LENGTH: 40
<212> TYPE: DNA
<213> ORGANISM: Homo sapiens;

<400> SEQUENCE: 379
gctagatgaa gagcaagcgc ttttcaggct gtgaaccttg                           40

<210> SEQ ID NO 380
<211> LENGTH: 40
<212> TYPE: DNA
<213> ORGANISM: Homo sapiens;

<400> SEQUENCE: 380
tacaaccgac agatgtatgt gagatcctcc ccgctaccag                           40

<210> SEQ ID NO 381
<211> LENGTH: 40
<212> TYPE: DNA
<213> ORGANISM: Homo sapiens;

<400> SEQUENCE: 381
gctagatgaa gagcaagcgc ggattttgga aaccagcaga                           40

<210> SEQ ID NO 382
<211> LENGTH: 40
<212> TYPE: DNA
<213> ORGANISM: Homo sapiens;

<400> SEQUENCE: 382
tacaaccgac agatgtatgt ctgtctgtct gtccgtcagc                           40

<210> SEQ ID NO 383
<211> LENGTH: 40
<212> TYPE: DNA
<213> ORGANISM: Homo sapiens;

<400> SEQUENCE: 383
gctagatgaa gagcaagcgc agggtttcgg gaaccagatc                           40

<210> SEQ ID NO 384
<211> LENGTH: 40
```

<212> TYPE: DNA
<213> ORGANISM: Homo sapiens;

<400> SEQUENCE: 384
tacaaccgac agatgtatgt ctcggtgatt tagcagcaag        40

<210> SEQ ID NO 385
<211> LENGTH: 40
<212> TYPE: DNA
<213> ORGANISM: Homo sapiens;

<400> SEQUENCE: 385
gctagatgaa gagcaagcgc tccctctccc caagcttact        40

<210> SEQ ID NO 386
<211> LENGTH: 40
<212> TYPE: DNA
<213> ORGANISM: Homo sapiens;

<400> SEQUENCE: 386
tacaaccgac agatgtatgt ttcaggactt ccccttcctc        40

<210> SEQ ID NO 387
<211> LENGTH: 40
<212> TYPE: DNA
<213> ORGANISM: Homo sapiens;

<400> SEQUENCE: 387
gctagatgaa gagcaagcgc gtgctgaagt gtgaccagga        40

<210> SEQ ID NO 388
<211> LENGTH: 40
<212> TYPE: DNA
<213> ORGANISM: Homo sapiens;

<400> SEQUENCE: 388
tacaaccgac agatgtatgt gggcaatgga agtcgaaata        40

<210> SEQ ID NO 389
<211> LENGTH: 40
<212> TYPE: DNA
<213> ORGANISM: Homo sapiens;

<400> SEQUENCE: 389
gctagatgaa gagcaagcgc caacctgagc cagaaacctg        40

<210> SEQ ID NO 390
<211> LENGTH: 40
<212> TYPE: DNA
<213> ORGANISM: Homo sapiens;

<400> SEQUENCE: 390
tacaaccgac agatgtatgt ccacatttct ctggggacac        40

<210> SEQ ID NO 391
<211> LENGTH: 40
<212> TYPE: DNA
<213> ORGANISM: Homo sapiens;

<400> SEQUENCE: 391
gctagatgaa gagcaagcgc acaagttctg ggggacacag        40

<210> SEQ ID NO 392
<211> LENGTH: 40

```
<212> TYPE: DNA
<213> ORGANISM: Homo sapiens;

<400> SEQUENCE: 392
tacaaccgac agatgtatgt attgcaccta gggtttgtgc                    40

<210> SEQ ID NO 393
<211> LENGTH: 40
<212> TYPE: DNA
<213> ORGANISM: Homo sapiens;

<400> SEQUENCE: 393
gctagatgaa gagcaagcgc ctctagaggg cctgtgcaat                    40

<210> SEQ ID NO 394
<211> LENGTH: 40
<212> TYPE: DNA
<213> ORGANISM: Homo sapiens;

<400> SEQUENCE: 394
tacaaccgac agatgtatgt tcaatgtggg aaactgtcca                    40

<210> SEQ ID NO 395
<211> LENGTH: 40
<212> TYPE: DNA
<213> ORGANISM: Homo sapiens;

<400> SEQUENCE: 395
gctagatgaa gagcaagcgc gtgcctgtgt tctctgtgga                    40

<210> SEQ ID NO 396
<211> LENGTH: 40
<212> TYPE: DNA
<213> ORGANISM: Homo sapiens;

<400> SEQUENCE: 396
tacaaccgac agatgtatgt ccaagagcag tgtccatcct                    40

<210> SEQ ID NO 397
<211> LENGTH: 40
<212> TYPE: DNA
<213> ORGANISM: Homo sapiens;

<400> SEQUENCE: 397
gctagatgaa gagcaagcgc ctctagaggg cctgtgcaat                    40

<210> SEQ ID NO 398
<211> LENGTH: 40
<212> TYPE: DNA
<213> ORGANISM: Homo sapiens;

<400> SEQUENCE: 398
tacaaccgac agatgtatgt tcaatgtggg aaactgtcca                    40

<210> SEQ ID NO 399
<211> LENGTH: 40
<212> TYPE: DNA
<213> ORGANISM: Homo sapiens;

<400> SEQUENCE: 399
gctagatgaa gagcaagcgc cctcactgcc cttagctctg                    40

<210> SEQ ID NO 400
<211> LENGTH: 40
```

<212> TYPE: DNA
<213> ORGANISM: Homo sapiens;

<400> SEQUENCE: 400
tacaaccgac agatgtatgt cccgcaagaa acctcaaata    40

<210> SEQ ID NO 401
<211> LENGTH: 40
<212> TYPE: DNA
<213> ORGANISM: Homo sapiens;

<400> SEQUENCE: 401
gctagatgaa gagcaagcgc tgaggcttat gctgggagtt    40

<210> SEQ ID NO 402
<211> LENGTH: 40
<212> TYPE: DNA
<213> ORGANISM: Homo sapiens;

<400> SEQUENCE: 402
tacaaccgac agatgtatgt aaatggagca tgtccgagtc    40

<210> SEQ ID NO 403
<211> LENGTH: 41
<212> TYPE: DNA
<213> ORGANISM: Homo sapiens;

<400> SEQUENCE: 403
gctagatgaa gagcaagcgc cccctttgat tccctgaaat a    41

<210> SEQ ID NO 404
<211> LENGTH: 40
<212> TYPE: DNA
<213> ORGANISM: Homo sapiens;

<400> SEQUENCE: 404
tacaaccgac agatgtatgt gccccatgca tagttacctg    40

<210> SEQ ID NO 405
<211> LENGTH: 40
<212> TYPE: DNA
<213> ORGANISM: Homo sapiens;

<400> SEQUENCE: 405
gctagatgaa gagcaagcgc aggctctgca cagatggatt    40

<210> SEQ ID NO 406
<211> LENGTH: 40
<212> TYPE: DNA
<213> ORGANISM: Homo sapiens;

<400> SEQUENCE: 406
tacaaccgac agatgtatgt atgccctgcc cttttttaact    40

<210> SEQ ID NO 407
<211> LENGTH: 40
<212> TYPE: DNA
<213> ORGANISM: Homo sapiens;

<400> SEQUENCE: 407
gctagatgaa gagcaagcgc ctgaacaccg ctcccataaa    40

<210> SEQ ID NO 408
<211> LENGTH: 40

```
<212> TYPE: DNA
<213> ORGANISM: Homo sapiens;

<400> SEQUENCE: 408
tacaaccgac agatgtatgt cctcctccat cttcatgctc                         40

<210> SEQ ID NO 409
<211> LENGTH: 40
<212> TYPE: DNA
<213> ORGANISM: Homo sapiens;

<400> SEQUENCE: 409
gctagatgaa gagcaagcgc gcaccaggtg ttcattctga                         40

<210> SEQ ID NO 410
<211> LENGTH: 40
<212> TYPE: DNA
<213> ORGANISM: Homo sapiens;

<400> SEQUENCE: 410
tacaaccgac agatgtatgt ccgccatcac cttatcatct                         40

<210> SEQ ID NO 411
<211> LENGTH: 40
<212> TYPE: DNA
<213> ORGANISM: Homo sapiens;

<400> SEQUENCE: 411
gctagatgaa gagcaagcgc cccaaggcct gtgtttaaga                         40

<210> SEQ ID NO 412
<211> LENGTH: 40
<212> TYPE: DNA
<213> ORGANISM: Homo sapiens;

<400> SEQUENCE: 412
tacaaccgac agatgtatgt gcctccagtc cagtcttctg                         40

<210> SEQ ID NO 413
<211> LENGTH: 40
<212> TYPE: DNA
<213> ORGANISM: Homo sapiens;

<400> SEQUENCE: 413
gctagatgaa gagcaagcgc aggagggtgg acctagcact                         40

<210> SEQ ID NO 414
<211> LENGTH: 40
<212> TYPE: DNA
<213> ORGANISM: Homo sapiens;

<400> SEQUENCE: 414
tacaaccgac agatgtatgt caagtgatct tcacgcctca                         40

<210> SEQ ID NO 415
<211> LENGTH: 40
<212> TYPE: DNA
<213> ORGANISM: Homo sapiens;

<400> SEQUENCE: 415
gctagatgaa gagcaagcgc ggatagcaac tgctccaagg                         40

<210> SEQ ID NO 416
<211> LENGTH: 40
```

```
<212> TYPE: DNA
<213> ORGANISM: Homo sapiens;

<400> SEQUENCE: 416
tacaaccgac agatgtatgt tcacacatca gcttcccaaa                    40

<210> SEQ ID NO 417
<211> LENGTH: 40
<212> TYPE: DNA
<213> ORGANISM: Homo sapiens;

<400> SEQUENCE: 417
gctagatgaa gagcaagcgc ggcctgcttg ctgttcttac                    40

<210> SEQ ID NO 418
<211> LENGTH: 40
<212> TYPE: DNA
<213> ORGANISM: Homo sapiens;

<400> SEQUENCE: 418
tacaaccgac agatgtatgt tgcttcttct ccctcccttt                    40

<210> SEQ ID NO 419
<211> LENGTH: 40
<212> TYPE: DNA
<213> ORGANISM: Homo sapiens;

<400> SEQUENCE: 419
gctagatgaa gagcaagcgc cttgctgggc atgtctcata                    40

<210> SEQ ID NO 420
<211> LENGTH: 40
<212> TYPE: DNA
<213> ORGANISM: Homo sapiens;

<400> SEQUENCE: 420
tacaaccgac agatgtatgt gggggtcctg agagttccta                    40

<210> SEQ ID NO 421
<211> LENGTH: 40
<212> TYPE: DNA
<213> ORGANISM: Homo sapiens;

<400> SEQUENCE: 421
gctagatgaa gagcaagcgc tcactgccac cactctgttc                    40

<210> SEQ ID NO 422
<211> LENGTH: 40
<212> TYPE: DNA
<213> ORGANISM: Homo sapiens;

<400> SEQUENCE: 422
tacaaccgac agatgtatgt gcctcaacct ctcaaagtgc                    40

<210> SEQ ID NO 423
<211> LENGTH: 40
<212> TYPE: DNA
<213> ORGANISM: Homo sapiens;

<400> SEQUENCE: 423
gctagatgaa gagcaagcgc ctgccctggt aggttttctg                    40

<210> SEQ ID NO 424
<211> LENGTH: 39
```

```
<212> TYPE: DNA
<213> ORGANISM: Homo sapiens;

<400> SEQUENCE: 424
tacaaccgac agatgtatgt gaagacccag gtccagatg                              39

<210> SEQ ID NO 425
<211> LENGTH: 40
<212> TYPE: DNA
<213> ORGANISM: Homo sapiens;

<400> SEQUENCE: 425
gctagatgaa gagcaagcgc tctcagctca ctgcaagctc                             40

<210> SEQ ID NO 426
<211> LENGTH: 40
<212> TYPE: DNA
<213> ORGANISM: Homo sapiens;

<400> SEQUENCE: 426
tacaaccgac agatgtatgt acagtggctc atgcctgtaa                             40

<210> SEQ ID NO 427
<211> LENGTH: 40
<212> TYPE: DNA
<213> ORGANISM: Homo sapiens;

<400> SEQUENCE: 427
gctagatgaa gagcaagcgc aaagatgtgc gctgataggg                             40

<210> SEQ ID NO 428
<211> LENGTH: 40
<212> TYPE: DNA
<213> ORGANISM: Homo sapiens;

<400> SEQUENCE: 428
tacaaccgac agatgtatgt ttcccccatc tctcttctca                             40

<210> SEQ ID NO 429
<211> LENGTH: 40
<212> TYPE: DNA
<213> ORGANISM: Homo sapiens;

<400> SEQUENCE: 429
gctagatgaa gagcaagcgc aaagatgtgc gctgataggg                             40

<210> SEQ ID NO 430
<211> LENGTH: 40
<212> TYPE: DNA
<213> ORGANISM: Homo sapiens;

<400> SEQUENCE: 430
tacaaccgac agatgtatgt ttcccccatc tctcttctca                             40

<210> SEQ ID NO 431
<211> LENGTH: 40
<212> TYPE: DNA
<213> ORGANISM: Homo sapiens;

<400> SEQUENCE: 431
gctagatgaa gagcaagcgc acctggtccc caaaagaaat                             40

<210> SEQ ID NO 432
<211> LENGTH: 40
```

```
<212> TYPE: DNA
<213> ORGANISM: Homo sapiens;

<400> SEQUENCE: 432
tacaaccgac agatgtatgt aaagttgggg acacacaagc                          40

<210> SEQ ID NO 433
<211> LENGTH: 40
<212> TYPE: DNA
<213> ORGANISM: Homo sapiens;

<400> SEQUENCE: 433
gctagatgaa gagcaagcgc tgtccagggc tatggaagtc                          40

<210> SEQ ID NO 434
<211> LENGTH: 40
<212> TYPE: DNA
<213> ORGANISM: Homo sapiens;

<400> SEQUENCE: 434
tacaaccgac agatgtatgt tttcattctg acccggagac                          40

<210> SEQ ID NO 435
<211> LENGTH: 40
<212> TYPE: DNA
<213> ORGANISM: Homo sapiens;

<400> SEQUENCE: 435
gctagatgaa gagcaagcgc ctctcctatc ctgcctgctg                          40

<210> SEQ ID NO 436
<211> LENGTH: 40
<212> TYPE: DNA
<213> ORGANISM: Homo sapiens;

<400> SEQUENCE: 436
tacaaccgac agatgtatgt ggctggggta agtgtactgc                          40

<210> SEQ ID NO 437
<211> LENGTH: 46
<212> TYPE: DNA
<213> ORGANISM: Homo sapiens;

<400> SEQUENCE: 437
ctgctgctgc cgctggtgag accggtctca ccagcggcag cagcag                   46

<210> SEQ ID NO 438
<211> LENGTH: 46
<212> TYPE: DNA
<213> ORGANISM: Homo sapiens;

<400> SEQUENCE: 438
ctgctgctgc cactggtgag accggtctca ccagtggcag cagcag                   46

<210> SEQ ID NO 439
<211> LENGTH: 40
<212> TYPE: DNA
<213> ORGANISM: Homo sapiens;

<400> SEQUENCE: 439
gctagatgaa gagcaagcgc ggagtgagag gccatagctg                          40

<210> SEQ ID NO 440
<211> LENGTH: 40
```

```
<212> TYPE: DNA
<213> ORGANISM: Homo sapiens;

<400> SEQUENCE: 440
tacaaccgac agatgtatgt gcagtggctg aggttaggac                              40

<210> SEQ ID NO 441
<211> LENGTH: 40
<212> TYPE: DNA
<213> ORGANISM: Homo sapiens;

<400> SEQUENCE: 441
gctagatgaa gagcaagcgc atggtttgca ggaaacaagg                              40

<210> SEQ ID NO 442
<211> LENGTH: 40
<212> TYPE: DNA
<213> ORGANISM: Homo sapiens;

<400> SEQUENCE: 442
tacaaccgac agatgtatgt aaagcgggag atgaagtcct                              40

<210> SEQ ID NO 443
<211> LENGTH: 40
<212> TYPE: DNA
<213> ORGANISM: Homo sapiens;

<400> SEQUENCE: 443
gctagatgaa gagcaagcgc ggcagcataa gcaggacttc                              40

<210> SEQ ID NO 444
<211> LENGTH: 40
<212> TYPE: DNA
<213> ORGANISM: Homo sapiens;

<400> SEQUENCE: 444
tacaaccgac agatgtatgt gttgctcgag gacaagttcc                              40

<210> SEQ ID NO 445
<211> LENGTH: 40
<212> TYPE: DNA
<213> ORGANISM: Homo sapiens;

<400> SEQUENCE: 445
gctagatgaa gagcaagcgc tgctcccagg ctgtttattt                              40

<210> SEQ ID NO 446
<211> LENGTH: 40
<212> TYPE: DNA
<213> ORGANISM: Homo sapiens;

<400> SEQUENCE: 446
tacaaccgac agatgtatgt tgttttcagc tgcttgatgg                              40

<210> SEQ ID NO 447
<211> LENGTH: 40
<212> TYPE: DNA
<213> ORGANISM: Homo sapiens;

<400> SEQUENCE: 447
gctagatgaa gagcaagcgc gaatgaaatg ccccagagaa                              40

<210> SEQ ID NO 448
<211> LENGTH: 40
```

<212> TYPE: DNA
<213> ORGANISM: Homo sapiens;

<400> SEQUENCE: 448
tacaaccgac agatgtatgt actgtggggt tcaacctctg          40

<210> SEQ ID NO 449
<211> LENGTH: 40
<212> TYPE: DNA
<213> ORGANISM: Homo sapiens;

<400> SEQUENCE: 449
gctagatgaa gagcaagcgc tgttcttagc caccccactc          40

<210> SEQ ID NO 450
<211> LENGTH: 40
<212> TYPE: DNA
<213> ORGANISM: Homo sapiens;

<400> SEQUENCE: 450
tacaaccgac agatgtatgt gtgatcgtac aggtgcatcg          40

<210> SEQ ID NO 451
<211> LENGTH: 40
<212> TYPE: DNA
<213> ORGANISM: Homo sapiens;

<400> SEQUENCE: 451
gctagatgaa gagcaagcgc ctgcaaacag tgggctaaca          40

<210> SEQ ID NO 452
<211> LENGTH: 40
<212> TYPE: DNA
<213> ORGANISM: Homo sapiens;

<400> SEQUENCE: 452
tacaaccgac agatgtatgt cccacaatca ttccagtgaa          40

<210> SEQ ID NO 453
<211> LENGTH: 40
<212> TYPE: DNA
<213> ORGANISM: Homo sapiens;

<400> SEQUENCE: 453
gctagatgaa gagcaagcgc tccccctagt tgtgtcttgc          40

<210> SEQ ID NO 454
<211> LENGTH: 40
<212> TYPE: DNA
<213> ORGANISM: Homo sapiens;

<400> SEQUENCE: 454
tacaaccgac agatgtatgt tcatgggaaa atcccacatt          40

<210> SEQ ID NO 455
<211> LENGTH: 40
<212> TYPE: DNA
<213> ORGANISM: Homo sapiens;

<400> SEQUENCE: 455
gctagatgaa gagcaagcgc gacagtggct tctccaggtg          40

<210> SEQ ID NO 456
<211> LENGTH: 40

```
<212> TYPE: DNA
<213> ORGANISM: Homo sapiens;

<400> SEQUENCE: 456
tacaaccgac agatgtatgt tcccaaaaca caatccagaa                             40

<210> SEQ ID NO 457
<211> LENGTH: 40
<212> TYPE: DNA
<213> ORGANISM: Homo sapiens;

<400> SEQUENCE: 457
gctagatgaa gagcaagcgc caagagtgcc cagagagtcc                             40

<210> SEQ ID NO 458
<211> LENGTH: 41
<212> TYPE: DNA
<213> ORGANISM: Homo sapiens;

<400> SEQUENCE: 458
tacaaccgac agatgtatgt ttctccctaa ggcattttgg t                           41

<210> SEQ ID NO 459
<211> LENGTH: 40
<212> TYPE: DNA
<213> ORGANISM: Homo sapiens;

<400> SEQUENCE: 459
gctagatgaa gagcaagcgc gcctctcctg actgtcatcc                             40

<210> SEQ ID NO 460
<211> LENGTH: 40
<212> TYPE: DNA
<213> ORGANISM: Homo sapiens;

<400> SEQUENCE: 460
tacaaccgac agatgtatgt tcacaaagcg gaagaatgtg                             40

<210> SEQ ID NO 461
<211> LENGTH: 40
<212> TYPE: DNA
<213> ORGANISM: Homo sapiens;

<400> SEQUENCE: 461
gctagatgaa gagcaagcgc gggtttggtt ttggtttcct                             40

<210> SEQ ID NO 462
<211> LENGTH: 40
<212> TYPE: DNA
<213> ORGANISM: Homo sapiens;

<400> SEQUENCE: 462
tacaaccgac agatgtatgt cccgagagag agatcgacag                             40

<210> SEQ ID NO 463
<211> LENGTH: 40
<212> TYPE: DNA
<213> ORGANISM: Homo sapiens;

<400> SEQUENCE: 463
gctagatgaa gagcaagcgc tgtctccctc tgctcacctt                             40

<210> SEQ ID NO 464
<211> LENGTH: 40
```

<212> TYPE: DNA
<213> ORGANISM: Homo sapiens;

<400> SEQUENCE: 464
tacaaccgac agatgtatgt aggaggaggt gtagggtggt            40

<210> SEQ ID NO 465
<211> LENGTH: 40
<212> TYPE: DNA
<213> ORGANISM: Homo sapiens;

<400> SEQUENCE: 465
gctagatgaa gagcaagcgc aggtgaggca gcaggagaat            40

<210> SEQ ID NO 466
<211> LENGTH: 40
<212> TYPE: DNA
<213> ORGANISM: Homo sapiens;

<400> SEQUENCE: 466
tacaaccgac agatgtatgt atgaggtgag cagcaggttt            40

<210> SEQ ID NO 467
<211> LENGTH: 40
<212> TYPE: DNA
<213> ORGANISM: Homo sapiens;

<400> SEQUENCE: 467
gctagatgaa gagcaagcgc ttccccaggt agagcaacac            40

<210> SEQ ID NO 468
<211> LENGTH: 40
<212> TYPE: DNA
<213> ORGANISM: Homo sapiens;

<400> SEQUENCE: 468
tacaaccgac agatgtatgt gatggggtgg aagaagttga            40

<210> SEQ ID NO 469
<211> LENGTH: 40
<212> TYPE: DNA
<213> ORGANISM: Homo sapiens;

<400> SEQUENCE: 469
gctagatgaa gagcaagcgc acctggtccc caaaagaaat            40

<210> SEQ ID NO 470
<211> LENGTH: 40
<212> TYPE: DNA
<213> ORGANISM: Homo sapiens;

<400> SEQUENCE: 470
tacaaccgac agatgtatgt aaagttgggg acacacaagc            40

<210> SEQ ID NO 471
<211> LENGTH: 39
<212> TYPE: DNA
<213> ORGANISM: Homo sapiens;

<400> SEQUENCE: 471
gctagatgaa gagcaagcgc cgaggccctc ctacctttt            39

<210> SEQ ID NO 472
<211> LENGTH: 40

```
<212> TYPE: DNA
<213> ORGANISM: Homo sapiens;

<400> SEQUENCE: 472
tacaaccgac agatgtatgt tcgatagtct tgcaggtgga                              40

<210> SEQ ID NO 473
<211> LENGTH: 40
<212> TYPE: DNA
<213> ORGANISM: Homo sapiens;

<400> SEQUENCE: 473
gctagatgaa gagcaagcgc ttccccaggt agagcaacac                              40

<210> SEQ ID NO 474
<211> LENGTH: 40
<212> TYPE: DNA
<213> ORGANISM: Homo sapiens;

<400> SEQUENCE: 474
tacaaccgac agatgtatgt gatggggtgg aagaagttga                              40

<210> SEQ ID NO 475
<211> LENGTH: 40
<212> TYPE: DNA
<213> ORGANISM: Homo sapiens;

<400> SEQUENCE: 475
gctagatgaa gagcaagcgc ccaggtccac acattcctct                              40

<210> SEQ ID NO 476
<211> LENGTH: 40
<212> TYPE: DNA
<213> ORGANISM: Homo sapiens;

<400> SEQUENCE: 476
tacaaccgac agatgtatgt ttaccatttg cgatcacctg                              40

<210> SEQ ID NO 477
<211> LENGTH: 40
<212> TYPE: DNA
<213> ORGANISM: Homo sapiens;

<400> SEQUENCE: 477
gctagatgaa gagcaagcgc ccaggtccac acattcctct                              40

<210> SEQ ID NO 478
<211> LENGTH: 40
<212> TYPE: DNA
<213> ORGANISM: Homo sapiens;

<400> SEQUENCE: 478
tacaaccgac agatgtatgt ttaccatttg cgatcacctg                              40

<210> SEQ ID NO 479
<211> LENGTH: 40
<212> TYPE: DNA
<213> ORGANISM: Homo sapiens;

<400> SEQUENCE: 479
gctagatgaa gagcaagcgc ggggtggaac ctctttgatt                              40

<210> SEQ ID NO 480
<211> LENGTH: 40
```

```
<212> TYPE: DNA
<213> ORGANISM: Homo sapiens;

<400> SEQUENCE: 480
tacaaccgac agatgtatgt gcttaatgag cgtggtgtga                              40

<210> SEQ ID NO 481
<211> LENGTH: 40
<212> TYPE: DNA
<213> ORGANISM: Homo sapiens;

<400> SEQUENCE: 481
gctagatgaa gagcaagcgc tgggtaaggg acatctgctc                              40

<210> SEQ ID NO 482
<211> LENGTH: 40
<212> TYPE: DNA
<213> ORGANISM: Homo sapiens;

<400> SEQUENCE: 482
tacaaccgac agatgtatgt cagataggtg ccctcctgaa                              40

<210> SEQ ID NO 483
<211> LENGTH: 40
<212> TYPE: DNA
<213> ORGANISM: Homo sapiens;

<400> SEQUENCE: 483
gctagatgaa gagcaagcgc cctgccaaag aagaaacacc                              40

<210> SEQ ID NO 484
<211> LENGTH: 40
<212> TYPE: DNA
<213> ORGANISM: Homo sapiens;

<400> SEQUENCE: 484
tacaaccgac agatgtatgt gatgaagccc accaaacagt                              40

<210> SEQ ID NO 485
<211> LENGTH: 40
<212> TYPE: DNA
<213> ORGANISM: Homo sapiens;

<400> SEQUENCE: 485
gctagatgaa gagcaagcgc actgggctct gaccacaatc                              40

<210> SEQ ID NO 486
<211> LENGTH: 40
<212> TYPE: DNA
<213> ORGANISM: Homo sapiens;

<400> SEQUENCE: 486
tacaaccgac agatgtatgt ggctgatcct tcccagaaat                              40

<210> SEQ ID NO 487
<211> LENGTH: 39
<212> TYPE: DNA
<213> ORGANISM: Homo sapiens;

<400> SEQUENCE: 487
gctagatgaa gagcaagcgt ggtgtctcca ggtcaatca                               39

<210> SEQ ID NO 488
<211> LENGTH: 40
```

```
<212> TYPE: DNA
<213> ORGANISM: Homo sapiens;

<400> SEQUENCE: 488
tacaaccgac agatgtatgt ggctgatcct tcccagaaat          40

<210> SEQ ID NO 489
<211> LENGTH: 39
<212> TYPE: DNA
<213> ORGANISM: Homo sapiens;

<400> SEQUENCE: 489
gctagatgaa gagcaagcgt gacggcagga attacattg           39

<210> SEQ ID NO 490
<211> LENGTH: 41
<212> TYPE: DNA
<213> ORGANISM: Homo sapiens;

<400> SEQUENCE: 490
tacaaccgac agatgtatgt tgtttcttct ttggcaggag a        41

<210> SEQ ID NO 491
<211> LENGTH: 39
<212> TYPE: DNA
<213> ORGANISM: Homo sapiens;

<400> SEQUENCE: 491
gctagatgaa gagcaagcgc catggagttg ggcttagag           39

<210> SEQ ID NO 492
<211> LENGTH: 40
<212> TYPE: DNA
<213> ORGANISM: Homo sapiens;

<400> SEQUENCE: 492
tacaaccgac agatgtatgt ccatgccagt gctgtatttg          40

<210> SEQ ID NO 493
<211> LENGTH: 40
<212> TYPE: DNA
<213> ORGANISM: Homo sapiens;

<400> SEQUENCE: 493
gctagatgaa gagcaagcgc gcacaattca acacctctgc          40

<210> SEQ ID NO 494
<211> LENGTH: 40
<212> TYPE: DNA
<213> ORGANISM: Homo sapiens;

<400> SEQUENCE: 494
tacaaccgac agatgtatgt ctgcaacctt ccactgtcct          40

<210> SEQ ID NO 495
<211> LENGTH: 40
<212> TYPE: DNA
<213> ORGANISM: Homo sapiens;

<400> SEQUENCE: 495
gctagatgaa gagcaagcgc gatctgcaga gccatcttcc          40

<210> SEQ ID NO 496
<211> LENGTH: 40
```

```
<212> TYPE: DNA
<213> ORGANISM: Homo sapiens;

<400> SEQUENCE: 496
tacaaccgac agatgtatgt tgaggtcctt cagctccagt                          40

<210> SEQ ID NO 497
<211> LENGTH: 40
<212> TYPE: DNA
<213> ORGANISM: Homo sapiens;

<400> SEQUENCE: 497
gctagatgaa gagcaagcgc gcagaagagc ccaactcctt                          40

<210> SEQ ID NO 498
<211> LENGTH: 40
<212> TYPE: DNA
<213> ORGANISM: Homo sapiens;

<400> SEQUENCE: 498
tacaaccgac agatgtatgt tgcatgtgtg gttgtgattg                          40

<210> SEQ ID NO 499
<211> LENGTH: 40
<212> TYPE: DNA
<213> ORGANISM: Homo sapiens;

<400> SEQUENCE: 499
gctagatgaa gagcaagcgc aaggttcccc caacagactt                          40

<210> SEQ ID NO 500
<211> LENGTH: 40
<212> TYPE: DNA
<213> ORGANISM: Homo sapiens;

<400> SEQUENCE: 500
tacaaccgac agatgtatgt caagctaagc caacatgcaa                          40

<210> SEQ ID NO 501
<211> LENGTH: 38
<212> TYPE: DNA
<213> ORGANISM: Homo sapiens;

<400> SEQUENCE: 501
gctagatgaa gagcaagcgc gctcacctgc cagactgc                            38

<210> SEQ ID NO 502
<211> LENGTH: 40
<212> TYPE: DNA
<213> ORGANISM: Homo sapiens;

<400> SEQUENCE: 502
gctagatgaa gagcaagcgc gccaggacga tgagagacat                          40

<210> SEQ ID NO 503
<211> LENGTH: 40
<212> TYPE: DNA
<213> ORGANISM: Homo sapiens;

<400> SEQUENCE: 503
gctagatgaa gagcaagcgc gcctctcctg actgtcatcc                          40

<210> SEQ ID NO 504
<211> LENGTH: 40
```

<212> TYPE: DNA
<213> ORGANISM: Homo sapiens;

<400> SEQUENCE: 504
tacaaccgac agatgtatgt tcacaaagcg gaagaatgtg        40

<210> SEQ ID NO 505
<211> LENGTH: 40
<212> TYPE: DNA
<213> ORGANISM: Homo sapiens;

<400> SEQUENCE: 505
gctagatgaa gagcaagcgc ccagccaaat gcattctctt        40

<210> SEQ ID NO 506
<211> LENGTH: 40
<212> TYPE: DNA
<213> ORGANISM: Homo sapiens;

<400> SEQUENCE: 506
tacaaccgac agatgtatgt cacagggaag gtgaagggta        40

<210> SEQ ID NO 507
<211> LENGTH: 40
<212> TYPE: DNA
<213> ORGANISM: Homo sapiens;

<400> SEQUENCE: 507
gctagatgaa gagcaagcgc cttgagccca ggagtttgag        40

<210> SEQ ID NO 508
<211> LENGTH: 40
<212> TYPE: DNA
<213> ORGANISM: Homo sapiens;

<400> SEQUENCE: 508
tacaaccgac agatgtatgt atcagaggct gcaaaccagt        40

<210> SEQ ID NO 509
<211> LENGTH: 40
<212> TYPE: DNA
<213> ORGANISM: Homo sapiens;

<400> SEQUENCE: 509
gctagatgaa gagcaagcgc catacagcac cttcgggtct        40

<210> SEQ ID NO 510
<211> LENGTH: 40
<212> TYPE: DNA
<213> ORGANISM: Homo sapiens;

<400> SEQUENCE: 510
tacaaccgac agatgtatgt gggcagactt tggaactcag        40

<210> SEQ ID NO 511
<211> LENGTH: 41
<212> TYPE: DNA
<213> ORGANISM: Homo sapiens;

<400> SEQUENCE: 511
gctagatgaa gagcaagcgc ccaaaagcca cactcaaaga c        41

<210> SEQ ID NO 512
<211> LENGTH: 41

```
<212> TYPE: DNA
<213> ORGANISM: Homo sapiens;

<400> SEQUENCE: 512
tacaaccgac agatgtatgt cttgagtgat ggtgatgttc a            41

<210> SEQ ID NO 513
<211> LENGTH: 40
<212> TYPE: DNA
<213> ORGANISM: Homo sapiens;

<400> SEQUENCE: 513
gctagatgaa gagcaagcgc aggcagagag ggaaggagag              40

<210> SEQ ID NO 514
<211> LENGTH: 40
<212> TYPE: DNA
<213> ORGANISM: Homo sapiens;

<400> SEQUENCE: 514
tacaaccgac agatgtatgt aaacagcgag ggagaaactg              40

<210> SEQ ID NO 515
<211> LENGTH: 40
<212> TYPE: DNA
<213> ORGANISM: Homo sapiens;

<400> SEQUENCE: 515
gctagatgaa gagcaagcgc tcattttccc tcggtttcag              40

<210> SEQ ID NO 516
<211> LENGTH: 40
<212> TYPE: DNA
<213> ORGANISM: Homo sapiens;

<400> SEQUENCE: 516
tacaaccgac agatgtatgt agaacagagg gggaagcagt              40

<210> SEQ ID NO 517
<211> LENGTH: 39
<212> TYPE: DNA
<213> ORGANISM: Homo sapiens;

<400> SEQUENCE: 517
gctagatgaa gagcaagcgc gcggcctgga gtcttagtt               39

<210> SEQ ID NO 518
<211> LENGTH: 40
<212> TYPE: DNA
<213> ORGANISM: Homo sapiens;

<400> SEQUENCE: 518
tacaaccgac agatgtatgt gatcatatgg ggcctgaaca              40

<210> SEQ ID NO 519
<211> LENGTH: 40
<212> TYPE: DNA
<213> ORGANISM: Homo sapiens;

<400> SEQUENCE: 519
gctagatgaa gagcaagcgc gaatgaaatg ccccagagaa              40

<210> SEQ ID NO 520
<211> LENGTH: 40
```

```
<212> TYPE: DNA
<213> ORGANISM: Homo sapiens;

<400> SEQUENCE: 520
tacaaccgac agatgtatgt actgtggggt tcaacctctg                              40

<210> SEQ ID NO 521
<211> LENGTH: 39
<212> TYPE: DNA
<213> ORGANISM: Homo sapiens;

<400> SEQUENCE: 521
gctagatgaa gagcaagcgt ggcagcgtct tactcagaa                              39

<210> SEQ ID NO 522
<211> LENGTH: 40
<212> TYPE: DNA
<213> ORGANISM: Homo sapiens;

<400> SEQUENCE: 522
tacaaccgac agatgtatgt agaacagccc aacacgtacc                             40

<210> SEQ ID NO 523
<211> LENGTH: 39
<212> TYPE: DNA
<213> ORGANISM: Homo sapiens;

<400> SEQUENCE: 523
gctagatgaa gagcaagcga cccaaactag gcctcacct                              39

<210> SEQ ID NO 524
<211> LENGTH: 40
<212> TYPE: DNA
<213> ORGANISM: Homo sapiens;

<400> SEQUENCE: 524
tacaaccgac agatgtatgt acaggtggca tcttggaaac                             40

<210> SEQ ID NO 525
<211> LENGTH: 39
<212> TYPE: DNA
<213> ORGANISM: Homo sapiens;

<400> SEQUENCE: 525
gctagatgaa gagcaagcgc cactgactgg gtgtgtgtc                              39

<210> SEQ ID NO 526
<211> LENGTH: 41
<212> TYPE: DNA
<213> ORGANISM: Homo sapiens;

<400> SEQUENCE: 526
tacaaccgac agatgtatgt cctcagtcca ctcttgcctt t                           41

<210> SEQ ID NO 527
<211> LENGTH: 39
<212> TYPE: DNA
<213> ORGANISM: Homo sapiens;

<400> SEQUENCE: 527
gctagatgaa gagcaagcgc ttccttccct gcctttgt                               39

<210> SEQ ID NO 528
<211> LENGTH: 41
```

```
<212> TYPE: DNA
<213> ORGANISM: Homo sapiens;

<400> SEQUENCE: 528
tacaaccgac agatgtatgt cccaacaact ttacctggat g                    41

<210> SEQ ID NO 529
<211> LENGTH: 43
<212> TYPE: DNA
<213> ORGANISM: Homo sapiens;

<400> SEQUENCE: 529
gctagatgaa gagcaagcgc catccattac attttcaggc ttt                  43

<210> SEQ ID NO 530
<211> LENGTH: 41
<212> TYPE: DNA
<213> ORGANISM: Homo sapiens;

<400> SEQUENCE: 530
tacaaccgac agatgtatgt ggttgatgct tttgaagaac g                    41

<210> SEQ ID NO 531
<211> LENGTH: 39
<212> TYPE: DNA
<213> ORGANISM: Homo sapiens;

<400> SEQUENCE: 531
gctagatgaa gagcaagcgt cctgacctca agtgatcca                       39

<210> SEQ ID NO 532
<211> LENGTH: 41
<212> TYPE: DNA
<213> ORGANISM: Homo sapiens;

<400> SEQUENCE: 532
tacaaccgac agatgtatgt cgttcttcaa aagcatcaac c                    41

<210> SEQ ID NO 533
<211> LENGTH: 39
<212> TYPE: DNA
<213> ORGANISM: Homo sapiens;

<400> SEQUENCE: 533
gctagatgaa gagcaagcgc gctacgtgga cgacacgct                       39

<210> SEQ ID NO 534
<211> LENGTH: 41
<212> TYPE: DNA
<213> ORGANISM: Homo sapiens;

<400> SEQUENCE: 534
tacaaccgac agatgtatgt cagtctgtgc cttggcgttg c                    41

<210> SEQ ID NO 535
<211> LENGTH: 40
<212> TYPE: DNA
<213> ORGANISM: Homo sapiens;

<400> SEQUENCE: 535
gctagatgaa gagcaagcgc aggcacagtg tcaccttcgt                      40

<210> SEQ ID NO 536
<211> LENGTH: 40
```

```
<212> TYPE: DNA
<213> ORGANISM: Homo sapiens;

<400> SEQUENCE: 536
tacaaccgac agatgtatgt gccgtagaag caaaggtagc                    40

<210> SEQ ID NO 537
<211> LENGTH: 39
<212> TYPE: DNA
<213> ORGANISM: Homo sapiens;

<400> SEQUENCE: 537
gctagatgaa gagcaagcgc ctgccaaaga agaaacacc                     39

<210> SEQ ID NO 538
<211> LENGTH: 43
<212> TYPE: DNA
<213> ORGANISM: Homo sapiens;

<400> SEQUENCE: 538
tacaaccgac agatgtatgt cgtgagggta gagaggatat ctg                43

<210> SEQ ID NO 539
<211> LENGTH: 39
<212> TYPE: DNA
<213> ORGANISM: Homo sapiens;

<400> SEQUENCE: 539
gctagatgaa gagcaagcgc ctgccaaaga agaaacacc                     39

<210> SEQ ID NO 540
<211> LENGTH: 43
<212> TYPE: DNA
<213> ORGANISM: Homo sapiens;

<400> SEQUENCE: 540
tacaaccgac agatgtatgt cgtgagggta gagaggatat ctg                43

<210> SEQ ID NO 541
<211> LENGTH: 50
<212> TYPE: DNA
<213> ORGANISM: Homo sapiens;

<400> SEQUENCE: 541
gtcgtcaaga tgctaccgtt caggagtcgt caagatgcta ccgttcagga         50

<210> SEQ ID NO 542
<211> LENGTH: 19
<212> TYPE: DNA
<213> ORGANISM: Homo sapiens;

<400> SEQUENCE: 542
cttgacgact cctgaacgg                                           19

<210> SEQ ID NO 543
<211> LENGTH: 19
<212> TYPE: DNA
<213> ORGANISM: Homo sapiens;

<400> SEQUENCE: 543
cttgacgaca cctgaacgg                                           19

<210> SEQ ID NO 544
<211> LENGTH: 20
```

-continued

```
<212> TYPE: DNA
<213> ORGANISM: Homo sapiens;

<400> SEQUENCE: 544
gctagatgaa gagcaagcgc                                               20

<210> SEQ ID NO 545
<211> LENGTH: 20
<212> TYPE: DNA
<213> ORGANISM: Homo sapiens;

<400> SEQUENCE: 545
tacaaccgac agatgtatgt                                               20
```